United States Patent [19]

Partis et al.

[11] Patent Number: 5,476,944
[45] Date of Patent: Dec. 19, 1995

[54] DERIVATIVES OF CYCLIC PHENOLIC THIOETHERS

[75] Inventors: Richard A. Partis, Evanston; Richard A. Mueller, Glencoe; Francis J. Koszyk, Prospect Heights; Richard M. Weier, Lake Bluff, all of Ill.

[73] Assignee: G. D. Searle & Co., Chicago, Ill.

[21] Appl. No.: 245,780

[22] Filed: May 19, 1994

Related U.S. Application Data

[63] Continuation-in-part of Ser. No. 211,074, Mar. 18, 1994, abandoned, which is a continuation-in-part of Ser. No. 794,759, Nov. 18, 1991, abandoned.

[51] Int. Cl.$^6$ ............... C07D 213/02; C07D 335/02; A61K 31/44; A61K 31/38

[52] U.S. Cl. ............... 514/357; 546/337; 558/239; 558/243; 558/248; 560/17; 560/61; 560/129; 560/174; 562/426; 562/465; 514/512; 514/513; 514/546; 514/576; 514/579; 514/618; 514/678; 514/617; 564/161; 564/162

[58] Field of Search ............... 540/479, 586; 544/158, 170, 391; 546/133, 146, 194, 245, 257, 336, 337; 549/65, 66, 417, 476; 558/32, 250, 252, 257, 239, 243, 248; 560/9, 17, 59, 61, 174, 129; 562/431, 426, 465; 564/162, 161; 568/74, 75; 514/183, 217, 237.5, 255, 305, 307, 317, 318, 357, 445, 460, 529, 530, 531, 532, 534, 576, 618, 512, 513, 546, 579, 678, 617, 161, 162

[56] References Cited

U.S. PATENT DOCUMENTS 5,147,893  9/1992  Mueller et al. ............... 514/530
5,250,567  10/1993  Mueller et al. ............... 514/473

FOREIGN PATENT DOCUMENTS 0131221  1/1985  European Pat. Off. ............... 514/381
0218782  4/1987  European Pat. Off. ............... 549/65
0235575  9/1987  European Pat. Off. ............... 514/381
0339688  11/1989  European Pat. Off. ............... 549/65

*Primary Examiner*—C. Warren Ivy
*Assistant Examiner*—Zinna N. Davis
*Attorney, Agent, or Firm*—Roberta L. Hastreiter; Roger A. Williams

[57] ABSTRACT

The present invention relates to derivatives of cyclic phenolic thioethers of the formula:

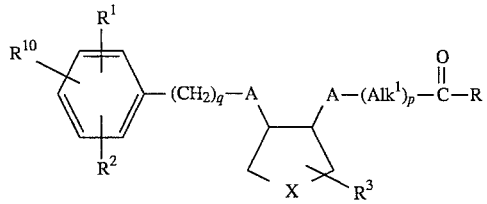

and the pharmaceutically acceptable salts thereof, which are inhibitors or stimulators of superoxide generation, and which may also inhibit cyclooxygenase and/or 5-lipoxygenase, to pharmaceutical compositions containing one or more of these compounds in combination with a pharmaceutically-acceptable carrier, and to medical methods of treatment employing these compounds.

23 Claims, No Drawings

DERIVATIVES OF CYCLIC PHENOLIC THIOETHERS

This application is a Continuation-in-Part of Ser. No. 08/211,074 filed Mar. 18, 1994, now abandoned, which is a Continuation-in-Part of Ser. No. 07/794,759 filed Nov. 18, 1991, now abandoned.

BACKGROUND OF THE INVENTION

1. Field of the Invention

This Application is a §371 of PCT/US92/09560, filed on Nov. 17, 1992.

The present invention relates to cyclic phenolic thioethers. More particularly, the present invention relates to the novel compounds of Formula I, which are inhibitors or stimulators of superoxide generation, and which may also inhibit cyclooxygenase and/or 5-lipoxygenase, to pharmaceutical compositions containing one or more of these compounds in combination with a pharmaceutically-acceptable carrier, and to medical methods of treatment employing these compounds.

The compounds of the present invention which stimulate superoxide generation may be useful as adjunctive therapeutic agents in the treatment of infections. Other compounds of the present invention which inhibit superoxide generation may be useful in the therapeutic or prophylactic treatment of disease conditions which are mediated wholly or partly by superoxide generation, such as adult respiratory distress syndrome, superoxide mediated inflammatory or allergic conditions, and other medical conditions which are caused by or aggravated by superoxide.

The compounds of Formula I which inhibit cyclooxygenase or 5-lipoxygenase are useful, for example, as anti-inflammatory and/or anti-allergy agents and in the treatment of hypersensitivity reactions, psoriasis, asthma, and related disorders and conditions in which physiologically active agents formed in the arachidonic acid metabolic pathway are involved. Compounds of the present invention may be useful in treating inflammatory and allergic conditions such as arthritis, asthma, and psoriasis.

2. Background Information

Recently, oxygen radicals have been implicated in the pathogenesis of many diseases. This implication is reflected by the many conferences devoted to this topic, books on the subject of free radicals and disease, and the appearance of two new specialized journals: *Free Radical Research Communications*, and *Free Radical Biology and Medicine*.

Much is known about the physicochemical properties of the various oxygen radicals, but knowledge of their overall importance in the initiation and amplification of human disease is limited. Some clinical conditions in which oxygen radicals are thought to be involved are discussed in Cross, C. E., et al., "Oxygen Radicals and Human Disease," *ANN. INT. MED.*, 107:526–545 (1987) (see Table 1, p. 527) and Ward, P. A., et al., "Oxygen Radicals, Inflammation, and Tissue Injury," *FREE RADICAL BIOLOGY & MEDICINE*, 5:403–408 (1988), each of which is incorporated herein by reference. Among the clinical conditions in which oxygen radicals are thought to be involved are, for example, inflammatory-immune injury, autoimmune diseases, ischemia-reflow states, aging disorders, cancer, cigarette-smoke effects, emphysema, acute respiratory distress syndrome (ARDS), atherosclerosis, rheumatoid arthritis, senile dementia, cataractogenesis, retinopathy of prematurity, radiation injury and contact dermatitis.

Oxygen radicals are capable of reversibly or irreversibly damaging compounds of all biochemical classes, including nucleic acids, protein and free amino acids, lipids and lipoproteins, carbohydrates, and connective tissue macromolecules. These species may have an impact on such cell activities as membrane function, metabolism, and gene expression. Oxygen radicals are formed in tissues by many processes (see Cross, et al., p. 528, Table 2). These are believed to be both endogenous, such as mitochondrial, microsomal and chloroplast electron transport chains; oxidant enzymes such as xanthine oxidase, indoleamine dioxygenase, tryptophan dioxygenase, galactose oxidase, cyclooxygenase, lipoxygenase, and monoamine oxidase; phagocytic cells, such as neutrophils, monocytes and macrophages, eosinophils, and endothelial cells; and antioxidation reactions; and exogenous, such as redoxcycling substances, drug oxidations, cigarette smoke, ionizing radiation, sunlight, heat shock and substances that oxidize glutathione. They may be involved in the action of toxins such as paraquat, cigarette smoke, and quinone antitumor drugs.

Those compounds of the present invention which inhibit superoxide generation may be useful in the treatment of diseases mediated by superoxide generation.

There are also some conditions in which the generation of superoxide may be desirable. Those compounds of the present invention which stimulate superoxide generation may be useful in the adjunctive therapy of microbial infections. See Goodman and Gilman's, The Pharmacological Basis of Therapeutics (7th Edition, 1985) p. 660–673; P. A. Ward, et. al., "Oxygen Radicals, Inflammation and Tissue Injury," *FREE RADICAL BIOLOGY & MEDICINE*, 5:403–408 (1988); and C. E. Cross, et. al., "Oxygen Radicals and Human Disease,"; *ANN. INT. MED.*, 107: 526–545 (1987), each of which is incorporated herein by reference. Generation of reactive oxygen species is a critical event in successful host defense against invading organisms. Both neutrophils and macrophages rely on a variety of oxidants to damage bacterial constituents (see V. L. Shepherd, "The role of the respiratory burst of phagocytes in host defense," *SEMIN RESPIR. INFECT.* (United States) June 1986, 1(2) p. 99–106, which is incorporated herein by reference.

It is well recognized that arachidonic acid, an essential unsaturated fatty acid, is enzymatically oxygenated to various products, including, prostaglandins, thromboxanes, the 5-, 11-, 12- and 15-hydroxyeicosatetraenoic acids (HETEs, DIHETEs) and hydroperoxyeicosatetraenoic acids (HPETEs) and the leukotrienes, all of which have potent physiological effects.

Those compounds of the present invention which inhibit cyclooxygenase inhibit the synthesis of prostaglandins via the cyclooxygenase pathway of arachidonic acid metabolism. These prostaglandin synthetase inhibitors may exhibit anti-inflammatory, anti-pyretic and analgesic activity, and are useful in the treatment of inflammatory conditions such as arthritis.

The leukotrienes, which are produced via the 5-lipoxygenase pathway, are the major contributors to the onset of the symptoms of asthma, and mediators for immediate hypersensitivity reactions, inflammation and other allergic responses.

Leukotrienes are found in inflammatory exudates and are involved in the process of cellular invasion during inflammation. The term "leukotrienes" is used as a generic term to describe a class of substances, such as slow-reacting substance (SRS) which is an important mediator in asthma and other hypersensitivity reactions. Immunologically generated SRS is usually referred to as slow-reacting substance of anaphylaxis (SRS-A). SRS-A consists of leukotrienes (LT) known as $A_4$, $B_4$, $C_4$, $D_4$, and $E_4$. $LTC_4$ is at least 100 times more potent than histamine in causing long lasting bronchoconstricting effects. The leukotrienes also increase vascular permeability and cause decreased cardiac output and impaired ventricular contraction. $LTB_4$ may be an important mediator of inflammation in, for example, inflammatory bowel disease.

Chemotaxis is a reaction by which the direction of migration of cells is determined by substances in their environment. It is one of the major processes bringing leukocytes from the blood to an inflammatory site, whether the inflammation is caused by an infectious agent, allergic challenge, or other pro-inflammatory stimuli. $LTB_4$ is not only chemotactic for neutrophils and monocytes, but is also highly active in stimulating eosinophil locomotion. $LTB_4$ also stimulates calcium influx and aggregation of polymorphonuclear leukocytes and $LTB_4$ may, thus, play an important role in mediating both acute and chronic inflammation.

Rheumatoid spondylitis is characterized by an acute neutrophil flareup in the joint which is associated with elevated levels of $LTB_4$. $LTB_4$ is also present in gouty effusions; and exposure to urate crystals is known to stimulate $LTB_4$ production by neutrophils. Accordingly, those compounds of the present invention which inhibit 5-lipoxygenase through inhibition of neutrophil attraction and activation in arthritic joints should reduce the protease and oxidative burden believed responsible for joint destruction in arthritic diseases.

Prior to the recognition of the significance of the arachidonic acid metabolism pathway in allergic reactions and inflammation, the search for effective therapeutic agents was based primarily on those agents which treated the symptoms of allergy and inflammation. There has since been an effort to develop new drugs which selectively block the formation of the mediators of these conditions, and the present invention provides new chemical entities which are inhibitors of the arachidonic acid pathway and are useful in the treatment of asthma, rheumatoid arthritis, osteoarthritis, psoriasis, and other allergic, hypersensitivity, and inflammatory conditions. Further examples of inflammatory conditions or diseases with an inflammatory or immune system component are disclosed in, for example, the Merck Manual of Diagnosis and Therapy, 15th Edition (1987) which is incorporated herein by reference.

Various thioether compounds have been described previously. For example, U.S. Pat. No. 4,711,903 and its continuation-in-part, U.S. Pat. No. 4,755,524, disclose compounds of the formula:

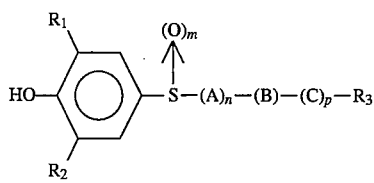

wherein: $R_1$ and $R_2$ are the same or different and independently represent tert-alkyl or phenyl; A represents methylene or methylene substituted by alkyl, dialkyl or hydroxy, provided that when A includes hydroxymethylene, the hydroxymethylene group is not adjacent to a heteroatom; B represents sulfur, sulfoxide, sulfone, oxygen, —NH— or nitrogen substituted by alkyl, phenyl, benzyl, substituted phenyl or substituted benzyl; C represents methylene or methylene substituted by alkyl; $R_3$ represents $CO_2H$, $CO_2$-alkyl or a tetrazole group; m is 0 or 1, n is 2, 3 or 4 and p is 1, 2 or 3; and the pharmaceutically acceptable salts thereof. The compounds are specific inhibitors of 5-lipoxygenase, and are useful in the treatment of local and systematic inflammation, allergy and hypersensitivity reactions and other disorders in which agents formed in the 5-lipoxygenase metabolic pathway are involved.

U.S. Pat. No. 4,621,098 and its equivalent, European Patent Application Publication No. 0131221, disclose compounds of the formula:

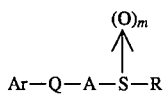

in which Ar is phenyl or phenyl substituted by one to three of varied substituents, for example, alkyl, alkoxy, hydroxy, etc.; Q is oxygen, sulfur or an NH group; A is straight or branched chain, optionally substituted, alkylene, and R is hydrogen or straight or branched alkyl, optionally substituted by alkoxy, hydroxyl, carboxyl, alkoxycarbonyl, etc.; and n is 0, 1 or 2. The disclosed compounds are indicated to have anti-inflammatory and anti-allergic properties through inhibition of undefined anaphylactic and anaphylactoid reactions, although no test data are provided. The preferred compounds are stated to be those in which Q represents oxygen and n is 0, without mention of any preference among the numerous possible substituents for R or substituted phenyl as Ar. In contrast to the invention disclosed in the foregoing publication, the compounds of the present invention all have cycloalkyl at the position corresponding to A as well as having di(tertiary)-alkyl or diphenyl groups as substituents on the phenol moiety corresponding to the substituted Ar group in the above publication which, as described therein, may or may not comprise a phenol.

U.S. Pat. Nos. 4,029,812, 4,076,841 and 4,078,084 disclose compounds of the formula:

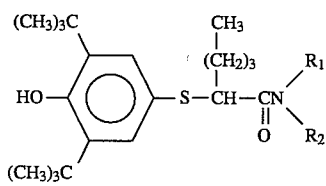

comprising 2-(3,5-di-tert-butyl-4-hydroxy-phenyl)thio carboxamides. The compounds are indicated to be useful in lowering serum cholesterol and triglyceride levels.

A series of thioethers, useful as, for example, polyfunctional antioxidants for polymers, and biologically active substances, obtained by the nucleophilic addition of thiols, including 3,5-di-tert-butyl-4-hydroxythio-phenol, and hydrogen sulfide to acrylate derivatives have been described. See Medvedev et al., Khimiya; Khimicheskaya Tekhnologiya, Volume 20, (1977), pp. 568–574. The compounds resulting from the foregoing process have the general formulas $RS(CH_2)_nX$ and $S(CH_2CH_2X)_2$ in which R is 3,5-di-tert-butyl-4-hydroxyphenyl and X represents, for example, —C≡N, $NH_2$, $CH(OH)CH_2Cl$, OH, COCl and various carboxy, carboxylate and amide functions. Compounds of formula I according to the present invention, or 5-lipoxygenase activity for structurally related compounds, are not disclosed. U.S. Pat. No. 4,153,803 discloses cholesterol-lowering phenoxyalkanoic acid esters of the formula:

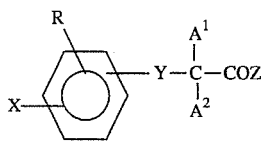

wherein, when Y is sulfur, X is hydrogen, benzyl, benzyloxy or benzylthio or substituted derivatives thereof; R is hydrogen, halogen, hydroxy, alkyl or alkoxy, $A^1$ and $A^2$ are hydrogen or alkyl and Z is amine or azacyclohydrocarbonyloxy.

JP 49116035 discloses a process for making compounds of the formula:

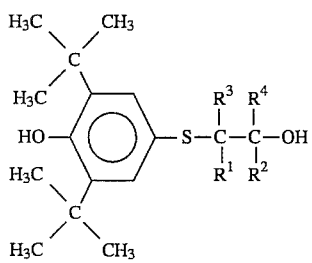

wherein $R^1$, $R^2$, $R^3$ and $R^4$ are hydrogen, alkyl or aryl groups, and $R^1$ and $R^2$ can be combined to form a cycloalkyl group. The compounds are said to be useful as drug intermediates, agricultural chemicals, antioxidants and industrial chemicals. Specifically disclosed is a compound of the formula:

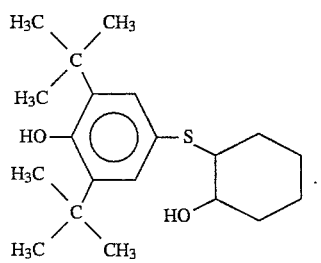

CA 107:197783q discloses dialkylphenol derivatives of the formula:

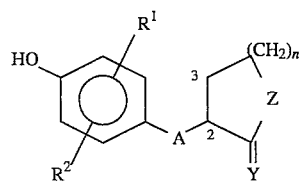

wherein $R^1$, $R^2$=alkyl; A=alkylene, S, SO; Y=alkoxyimino, O; Z=alkylene, O; n=1, 2; 2–3 saturated or unsaturated. The compounds are said to be useful as modifiers for biosynthesis of prostaglandins and leukotrienes and hypolipemics (no data).

These compounds differ structurally from the compounds claimed in the present application which have a carboxylic acid or ester moiety attached to the cycloalkyl ring through A—$(CH_2)_p$ or through A—$(CH_2)_p$— C(O)—$(CH_2)_r$ and which do not have an alkoxyimino or =O attached to the cycloalkyl ring.

EP0293900 discloses 5-lipoxygenase inhibiting compounds of the formula:

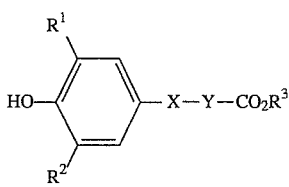

where $R^3$ and Y together are:

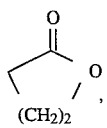

and n is 2 or 3.

These compounds differ structurally from the claimed compounds. They have a lactone structure (i.e., a dihydrofuranone or dihydro-pyranone) attached to the phenylthio, and lack a carboxylic acid or ester moiety attached to the heterocyclic ring through A—$(CH_2)_p$ or through A—$(CH_2)_p$—C(O)—$(CH_2)_r$.

Katsumi, et al., *CHEM. PHARM. BULL.* 34(4):1619–1627(1986) discloses 3,5-di-tert-butyl-4-hydroxystyrenes. Some of the compounds disclosed had anti-inflammatory activity and some inhibited 5-lipoxygenase. Only one compound (Compound 3, Table I) had S attached to the 3,5-di-tert-butyl-4-hydroxyphenol. It has the following structure:

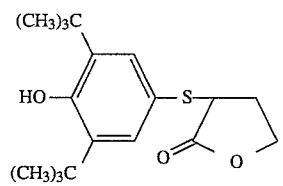

This compound differs structurally from the claimed compounds. It has a butyrolactone (i.e., a dihydro-2(3H)-furanone) attached to the thio and lacks a carboxylic acid or ester moiety attached to the heterocyclic ring through A—$(CH_2)_p$ or through A—$(CH_2)_p$— C(O)—$(CH_2)_r$. At the bottom of page 1621, the authors indicate that insertion of the thio group resulted in a loss of anti-inflammatory activity.

U.S. Pat. No. 4,801,611 discloses 5-lipoxygenase inhibitors of the formula:

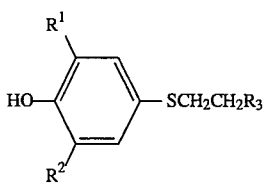

where $R_1$ and $R_2$ are tert-alkyl and $R_3$ can be:

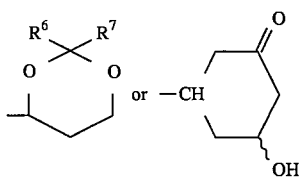

where $R_6$ and $R_7$ are $C_{1-4}$ alkyl.

These compounds differ structurally from the compounds of the present invention. Compound (c) has a dialkyl-1,3-dioxanyl group attached to the phenylthio through an alkylene bridge whereas compound (d) has a 4-hydroxy-2-pyranone attached to the phenylthio through an alkylene bridge. Neither compound has a carboxylic acid or ester moiety attached to the cycloalkyl ring through A—$(CH_2)_p$ or through A—$(CH_2)_p$—$C(O)$—$(CH_2)_r$, as do the compounds of the present invention, and both compound have an alkylene bridge inserted between the phenylthio and the heterocyclic ring.

Each of the documents described hereinabove discloses compounds which are structurally different from the compounds of the present invention. Thus, the compounds of the present invention are structurally distinct from that which has been described in the art.

Prostaglandins play a major role in the inflammation process and the inhibition of prostaglandin production, especially production of $PGG_2$, $PGH_2$ and $PGE_2$, has been a common target of anti-inflammatory drug discovery. However, common non-steroidal anti-inflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDS have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, *PROC. NATL. ACAD. SCI. USA*, 89, 7384 (1992), which is incorporated herein by reference, and named cyclooxygenase II (COX II) or prostaglandin G. H. synthase II. The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *PROC. NATL. ACAD. SCI. USA,* 89, 8917 (1992), which is incorporated herein by reference). The 6-methoxy-2-napthylacetic acid metabolite of nabumetone has been found by E. Meade et al to selectively inhibit the COX II enzyme (*J. BIOL. CHEM.,* 268, 6610 (1993), which is incorporated herein by reference). In addition, Futaki et al (*GEN. PHARMAC.,* 24, 105 (1993), which is incorporated herein by reference,) has reported that N-(2-cyclohexyloxy-4-nitrophenyl)methanesulfonamide is anti-inflammatory and lacks gastric side effects.

Compounds of the present invention inhibit cyclooxygenase II and/or cyclooxygenase I, and relieve the effects of inflammation. These compounds, in addition, produce a reduced amount of side effects.

Compounds of the present invention would be useful for the treatment of inflammation in an animal, and for treatment of other inflammation-associated disorders, such as an analgesic in the treatment of pain and headaches, or as an antipyretic for the treatment of fever. For example, compounds of the present invention would be useful to treat arthritis, including but not limited to rheumatoid arthritis, spondyloarthopathies, gouty arthritis, systemic lupus erythematosus, osteoarthritis and juvenile arthritis. Such compounds would be useful in the treatment of asthma, bronchitis, menstrual cramps, tendinitis, bursitis, and skin related conditions such as psoriasis, eczema, burns and dermatitis. Compounds of the present invention also would be useful to treat gastrointestinal conditions such as inflammatory bowel syndrome, Crohn's disease, gastritis, irritable bowel syndrome and ulcerative colitis. Compounds of the present invention would be useful in treating inflammation in such diseases as vascular diseases, migraine headaches, periarteritis nodosa, thyroiditis, aplastic anemia, Hodgkin's disease, sclerodoma, rheumatic fever, type I diabetes myasthenia gravis, sarcoidosis, nephrotic syndrome, Behcet'3 s syndrome, polymyositis, hypersensitivity, conjunctivitis, gingivitis, swelling occurring after injury, myocardial ischemia, and the like. Compounds of the present invention are useful as anti-inflammatory agents, such as for the treatment of arthritis, with the additional benefit of having significantly less harmful side effects.

The present invention also comprises a method of treating inflammation or inflammation-associated disorders in a subject, the method comprising administering to the subject having such inflammation or disorder a therapeutically-effective amount of a compound of Formula I.

SUMMARY OF THE INVENTION

It is, therefore, a primary object of the present invention to provide novel cyclic phenolic thioethers, pharmaceutical compositions containing them and methods of using them, as well as intermediates for producing them.

The novel cyclic phenolic thioethers of the present invention are compounds having a structure of the formula:

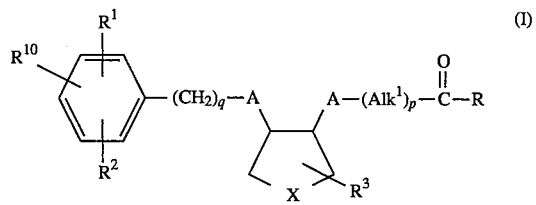

and the pharmaceutically acceptable salts thereof, wherein $R^1$, $R^2$ and $R^{10}$ are the same or different and independently represent alkyl, alkoxy, hydroxy, phenyl, halogen, trifluoromethyl, cyano, nitro, alkylthio or hydrogen, with the proviso that when $R^1$ and $R^2$ are 3,5-di-tert-butyl, $R^{10}$ is not 4-hydroxy; q is 0 or 1; $R^3$ represents hydrogen, alkyl, alkoxy, or hydroxy; X represents O, S or $(CH_2)_m$ wherein m is an integer from 0 to 4; A represents O or $S(O)_n$ wherein n is 0, 1, or 2, with the two As being the same or different; $Alk^1$ is straight or branched chain alkyl having 1 to 6 carbon atoms; p is an integer of from 0 to 2, but cannot be O when R is OH; and R represents:

(a) alkyl, with the proviso that, when A is oxygen, p is 0, q is 0, and $R^1$, $R^2$ and $R^{10}$ are all hydrogen, or are 2,4,6-trimethyl, or $R^1$ and $R^2$ are 2,4-dinitro and $R^{10}$ is hydrogen, or $R^1$ and $R^2$ are H and $R^{10}$ is 4-chloro or 4-nitro or 4-methyl, then R is not methyl;

(b) OH;

(c) $OR^4$ wherein $R^4$ is alkyl of 1 to 6 carbon atoms;

(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or $Alk-NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted; or (e) $(CH_2)_tCOOR^7$ wherein t is an integer from 1 to 4 and $R^7$ is hydrogen or alkyl of 1 to 4 carbon atoms.

Included in the present invention are compounds having a structure of the formula:

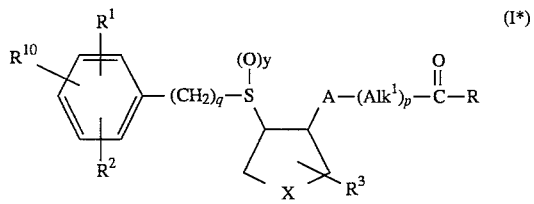

(I*)

and the pharmaceutically acceptable salts thereof, wherein $R^1$, $R^2$ and $R^{10}$ are the same or different and independently represent alkyl, alkoxy, hydroxy, phenyl, halogen, trifluoromethyl, cyano, nitro, alkylthio or hydrogen, with the proviso that when $R^1$ and $R^2$ are 3,5-di-tert-butyl, $R^{10}$ is not 4-hydroxy; q is 0 or 1; $R^3$ represents hydrogen, alkyl, alkoxy, or hydroxy; X represents O, S or $(CH_2)_m$ wherein m is an integer from 0 to 4; A represents O or $S(O)_n$ wherein n is 0, 1, or 2; $Alk^1$ is straight or branched chain alkyl having 1 to 6 carbon atoms; p is an integer of from 0 to 2, but cannot be O when R is OH; y is 0, 1 or 2; and R represents:

(a) alkyl;

(b) OH;

(c) $OR^4$ wherein $R^4$ is alkyl of 1 to 6 carbon atoms;

(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or $Alk-NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted; or (e) $(CH_2)_tCOOR^7$ wherein t is an integer from 1 to 4 and $R^7$ is hydrogen or alkyl of 1 to 4 carbon atoms.

The present invention also provides pharmaceutical compositions which are pharmaceutically acceptable and which comprise a therapeutically-effective amount of a compound of Formula I in combination with a pharmaceutically-acceptable carrier, and methods for treatment in animals, comprising administering a therapeutically-effective amount of a compound of Formula I to the animal.

It is a further object of the present invention to provide methods for stimulating or inhibiting superoxide generation and to provide methods for treating conditions mediated by products of the arachidonic acid metabolic pathway and for promoting anti-inflammatory and/or anti-allergic effects in mammals in need thereof by the administration of preselected dosages of compounds of the present invention or pharmaceutically acceptable salts thereof in appropriate non-toxic pharmaceutical dosage forms or compositions. Some compounds of the present invention may inhibit 5-lipoxygenase and/or cyclooxygenase(s). Those compounds which inhibit both 5-lipoxygenase and cyclooxygenase(s) have an advantage when administered to patients who are sensitive or allergic to cyclooxygenase inhibitors since the 5-lipoxygenase inhibiting activity may have a mitigating effect on the patient's sensitivity to cyclooxygenase inhibitors. This mitigating effect may also make compounds which inhibit both 5-lipoxygenase and cyclooxygenase(s) useful for co-administration with cyclooxygenase inhibitors.

Another object of the present invention is to provide dosage unit forms adapted for, e.g., oral, topical, and/or parenteral administration and useful in the stimulation or inhibition of superoxide generation and in the treatment, management and mitigation of inflammation, allergies, psoriasis and hypersensitivity reactions and related disorders and conditions in which physiologically active agents formed in the arachidonic acid metabolic pathway are involved.

Those compounds of the present invention which inhibit superoxide generation may be useful in the therapeutic or prophylactic treatment of disease conditions which are mediated wholly or partly by superoxide generation, such as adult respiratory distress syndrome, superoxide mediated inflammatory or allergic conditions, and other medical conditions which are caused by or aggravated by superoxide.

Those compounds of Formula I which are stimulators of superoxide generation in neutrophils may be useful in the therapeutic or prophylactic treatment of disease conditions in which superoxide generation is an important factor.

Although it has been speculated that 5-lipoxygenase may be involved in superoxide generation, the ability of some compounds, which inhibit 5-lipoxygenase, to stimulate superoxide generation in neutrophils, while others inhibit superoxide generation, indicates that superoxide generation is not governed by 5-lipoxygenase. Thus, the activity of the compounds of Formula I in stimulating or inhibiting superoxide generation is not related to the ability of these compounds to inhibit 5-lipoxygenase. Compounds which do not inhibit 5-lipoxygenase may still act as inhibitors or stimulators of superoxide generation. In general, those compounds of Formula I which are carboxylic acids inhibit superoxide generation and those compounds which are esters or heterocycle alkyl amides stimulate superoxide generation. Compounds of Formula I which are readily hydrolyzable to the carboxylic acid upon oral administration may also act as prodrugs which would be converted to superoxide inhibitors by stomach acid, blood, liver, or other organs. In addition, some compounds of Formula I may inhibit 5-lipoxygenase and/or cyclooxygenase.

The present invention provides a method by which neutrophil activation and the generation of superoxide anions are accomplished utilizing compounds of Formula I having the ability to stimulate superoxide generation. Accordingly these compounds of Formula I are useful in the design and testing of anti-inflammatory properties of other pharmacologically active agents.

The ability to produce superoxide, which may itself be microbicidal, or which is then converted to toxic oxidants, such as $H_2O_2$, OH radical, and singlet oxygen, is important to the phagocytic killing mechanisms which enable neutrophils and macrophages to kill bacteria, parasites and tumor cells through phagocytosis.

Therefore, compounds of Formula I which stimulate superoxide generation may be useful in the adjunctive therapy of microbial infections. The compounds may also be useful in treating conditions such as Chediak-Higashi Syndrome, in which the patient's macrophages and polymorphs are only weakly active causing the patients to suffer from recurring infections involving organisms with normally low pathogenicity. Compounds of Formula I which stimulate superoxide generation may also be useful in the adjunctive therapy of patients whose immune systems have been weakened or impaired by disease or by chemotherapy or radiation therapy and who are more subject to microbial infections.

DETAILED DESCRIPTION OF THE PREFERRED EMBODIMENTS (1) Description of Invention In one aspect, the present invention provides compounds comprising a structure of Formula I, as described above, and pharmaceutically-acceptable salts thereof.

Specific compounds within the scope of the invention include, but are not limited to, the compounds discussed in the examples presented below, as well as their pharmaceutically-acceptable salts.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of the present invention may contain a basic functional group, such as amino, alkylamino or dialkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. PHARM. SCI.,* 66, 1–19 (1977), which, as well as all other documents referred to herein, is incorporated herein by reference.)

In other cases, the compounds of the invention may contain one or more acidic functional groups, such as carboxyl and the like, and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., ""Pharmaceutical Salts," supra.)

In another aspect, the present invention provides pharmaceutically-acceptable compositions which comprise a therapeutically-effective amount of one or more of the compounds of Formula I, as described herein, formulated together with one or more pharmaceutically-acceptable carriers. The pharmaceutical compositions of the invention may be specially formulated for oral administration in solid or liquid form, or in the form of an aerosol for inhalation, for parenteral injection, or for rectal or vaginal administration.

In yet a further aspect, the present invention provides a method of inhibiting superoxide generation in an animal comprising administering to an animal in need of such treatment an amount of a compound of Formula I, or a pharmaceutically acceptable salt thereof, which is effective to inhibit superoxide generation.

In still another aspect, the present invention provides a method of stimulating superoxide generation in an animal which comprises administering to an animal in need of such treatment an amount of a compound of Formula I, or a pharmaceutically acceptable salt thereof, which is effective to stimulate superoxide generation.

The preferred embodiments of this invention are the compounds described in Examples 72, 76, 77, 80, 81, 84, 85, 88, 89, 92, 93, 97, 99 and 101. The most preferred embodiment of the invention is the compound described in Example 84 below.

These and other similar objects, advantages and features are accomplished according to the products, compositions and methods of the invention comprising compounds of the formula:

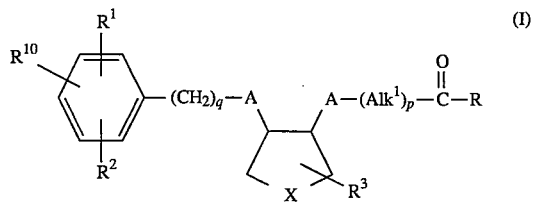

and the pharmaceutically acceptable salts thereof, wherein $R^1$, $R^2$ and $R^{10}$ are the same or different and independently represent alkyl, alkoxy, hydroxy, phenyl, halogen, trifluoromethyl, cyano, nitro, alkylthio or hydrogen, with the proviso that when $R^1$ and $R^2$ are 3,5-di-tert-butyl, $R^{10}$ is not 4-hydroxy; q is 0 or 1; $R^3$ represents hydrogen, alkyl, alkoxy, or hydroxy; X represents O, S or $(CH_2)_m$ wherein m is an integer from 0 to 4; A represents O or S(O). wherein n is 0, 1, or 2, with the two As being the same or different; $Alk^1$ is straight or branched chain alkyl having 1 to 6 carbon atoms; p is an integer of from 0 to 2, but p is not O when R is OH; and R represents:

(a) alkyl, with the proviso that, when A is oxygen, p is 0, q is 0, and $R^1$, $R^2$ and $R^{10}$ are all hydrogen, or are 2,4,6-trimethyl, or $R^1$ and $R^2$ are 2,4-dinitro and $R^{10}$ is hydrogen, or $R^1$ and $R^2$ are H and $R^{10}$ is 4-chloro or 4-nitro or 4-methyl, then R is not methyl;
(b) OH;
(c) $OR^4$ wherein $R^4$ is alkyl of 1 to 6 carbon atoms;
(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or Alk-$NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted; or
(e) $(CH_2)_tCOOR^7$ wherein t is an integer from 1 to 4 and $R^7$ is hydrogen or alkyl of 1 to 4 carbon atoms.

Included in the present invention are compounds of the formula:

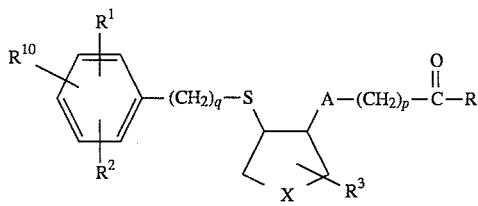

(Ia)

and the pharmaceutically acceptable salts thereof wherein $R^1$, $R^2$ and $R^{10}$ are the same or different and independently represent alkyl, alkoxy, hydroxy, phenyl, halogen, trifluoromethyl, cyano or hydrogen; q is 0 or 1; $R^3$ represents hydrogen, alkyl, alkoxy, or hydroxy; X represents O, S or $(CH_2)_m$ wherein m is 0 to 4; A represents O or $S(O)_n$ wherein n is 0, 1, or 2; p is an integer of from 0 to 2, but cannot be 0 when R is OH; and R represents:

(a) alkyl, with the proviso that, when A is oxygen, p is 0, q is 0, and $R^1$, $R^2$ and $R^{10}$ are all hydrogen, or are 2,4,6-trimethyl, or $R^1$ and $R^2$ are 2,4-dinitro and $R^{10}$ is hydrogen, or $R^1$ and $R^2$ are H and $R^{10}$ is 4-chloro or 4-nitro or 4-methyl, then R is not methyl;
(b) OH;
(c) $OR^4$ wherein $R^4$ is alkyl of 1 to 6 carbon atoms;
(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or Alk-$NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted; or
(e) $(CH_2)_tCOOR^7$ wherein t is an integer from 1 to 4 and $R^7$ is hydrogen or alkyl of 1 to 4 carbon atoms.

Included in the present invention are compounds of the formula:

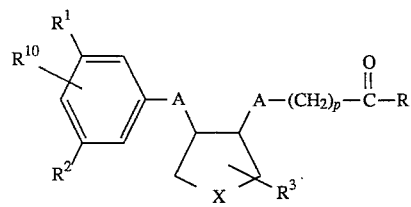

(Ib)

and the pharmaceutically acceptable salts thereof wherein $R^1$, $R^2$ and $R^{10}$ are the same or different and independently represent tert-alkyl of 4 to 10 carbon atoms, phenyl, halogen or hydrogen; $R^3$ represents hydrogen or alkyl of 1 to 4 carbon atoms; X represents O, S or $(CH_2)_m$ wherein m is 1 or 2; A represents O or $S(O)_n$ wherein n is 0, 1, or 2, with the two As being the same or different; p is an integer of from 0 to 4, but cannot be 0 when R is OH; and R represents:

(a) alkyl of 1 to 4 carbon atoms, with the proviso that, when A is oxygen, p is 0, q is 0, and $R^1$, $R^2$ and $R^{10}$ are all hydrogen, or are 2,4,6-trimethyl, or $R^1$ and $R^2$ are 2,4-dinitro and $R^{10}$ is hydrogen, or $R^1$ and $R^2$ are H and $R^{10}$ is 4-chloro or 4-nitro or 4-methyl, then R is not methyl;
(b) OH;
(c) $OR^4$ wherein $R^4$ is alkyl of 1 to 4 carbon atoms;
(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or Alk-$NR^8R^9$ wherein Alk is straight or branched chain alkyl of 1 to 6 carbon atoms and $R^8$ and $R^9$ each independently are hydrogen or alkyl of 1 to 4 carbon atoms; or $NR^5R^6$ together form a heterocyclic ring which may optionally be substituted; or
(e) $(CH_2)_tCOOR^7$ wherein t is an integer from 1 to 4 and $R^7$ is hydrogen or alkyl of 1 to 4 carbon atoms.

Included in the present invention are compounds of the formula:

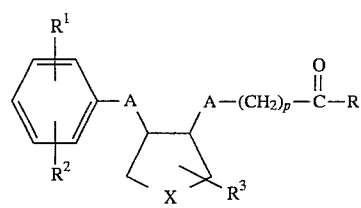

(II)

and the pharmaceutically acceptable salts thereof wherein $R^1$ and $R^2$ are the same or different and independently represent tert-butyl, phenyl, halogen or hydrogen; $R^3$ represents hydrogen or alkyl of 1 to 4 carbon atoms; X represents O or $(CH_2)_m$ wherein m is 1 or 2; A represents O or S, with the two As being the same or different; p is 0 or 1, but cannot be 0 when R is OH; and R represents:

(a) OH;
(b) $OR^4$ wherein $R^4$ is alkyl of 1 to 4 carbon atoms; or
(c) $NR^5R^6$ wherein $R^5$ is hydrogen or alkyl of 1 to 4 carbon atoms and $R^6$ is hydrogen, alkyl of 1 to 4 carbon atoms, hydroxyalkyl, alkoxyalkyl wherein the alkyl moieties each have 1 to 6 carbon atoms, heterocyclealkyl wherein the alkyl moiety has 1 to 4 carbon atoms, or Alk-$NR^8R^9$ wherein Alk is straight or branched chain alkyl of 1 to 6 carbon atoms and $R^8$ and $R^9$ are each independently hydrogen or alkyl of 1 to 4 carbon atoms; or $NR^5R^6$ together form a heterocyclic ring which may optionally be substituted.

Included in the present invention are compounds of the formula:

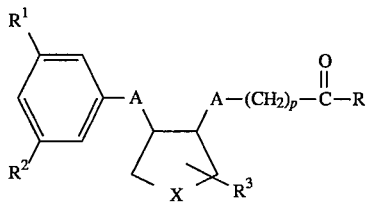
(IIa)

and the pharmaceutically acceptable salts thereof wherein $R^1$ and $R^2$ are the same or different and independently represent tert-butyl, phenyl, or hydrogen; $R^3$ represents hydrogen or alkyl of 1 to 4 carbon atoms; X represents O or $(CH_2)_m$ wherein m is 1 or 2; A represents O or S, with the two As being the same or different; p is an integer of from 0 to 4, but cannot be O when R is OH; and R represents:

(a) OH;

(b) $OR^4$ wherein $R^4$ is alkyl of 1 to 4 carbon atoms; or (c) $NR^5R^6$ wherein $R^5$ is hydrogen or alkyl of 1 to 4 carbon atoms and $R^6$ is hydrogen, alkyl of 1 to 4 carbon atoms, hydroxyalkyl, alkoxyalkyl wherein the alkyl moieties each have 1 to 6 carbon atoms, heterocyclealkyl wherein the alkyl moiety has 1 to 4 carbon atoms, or Alk-$NR^8R^9$ wherein Alk is straight or branched chain alkyl of 1 to 6 carbon atoms and $R^8$ and $R^9$ are each independently hydrogen or alkyl of 1 to 4 carbon atoms; or $NR^5R^6$ together form a heterocyclic ring which may optionally be substituted.

Included in the present invention are compounds of the formula:
and the pharmaceutically acceptable salts thereof wherein $R^1$ and $R^2$ are the same or different and independently represent tert-butyl, phenyl, or hydrogen; $R^3$ represents hydrogen or alkyl of 1 to 4 carbon atoms; X represents O or $(CH_2)_m$ wherein m is 1 or 2; A represents O or S, with the two As being the same or different; p is an integer of from 0 to 4, but cannot be O when R is OH; and R represents:

(a) OH;

(b) $OR^4$ wherein $R^4$ is alkyl of 1 to 4 carbon atoms; or (c) $NR^5R^6$ wherein $R^5$ is hydrogen or alkyl of 1 to 4 carbon atoms and $R^6$ is hydrogen, alkyl of 1 to 4 carbon atoms, hydroxyalkyl, alkoxyalkyl wherein the alkyl moieties each have 1 to 6 carbon atoms, heterocyclealkyl wherein the alkyl moiety has 1 to 4 carbon atoms, or Alk-$NR^8R^9$ wherein Alk is straight or branched chain alkyl of 1 to 6 carbon atoms and $R^8$ and $R^9$ are each independently hydrogen or alkyl of 1 to 4 carbon atoms; or $NR^5R^6$ together form a heterocyclic ring which may optionally be substituted.

Also included in the present invention are novel intermediates of the Formula III:

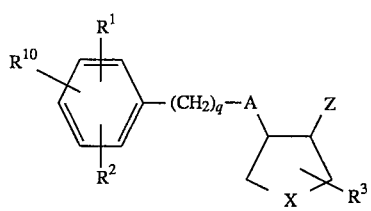
(III)

wherein $R^1$, $R^2$, $R^3$, $R^{10}$, q, A and X are defined as in Formula I, and Z represents hydroxy, halogen, sulfonate ester, or perfluoroacyl ester.

The compounds of Formula III are useful as intermediates for making compounds of Formula I.

In addition the present invention includes intermediate compounds of the Formula XV:

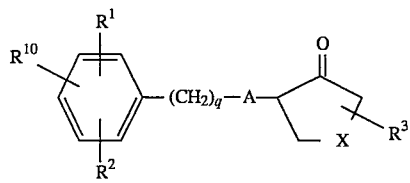
(XV)

wherein $R^1$, $R^2$, $R^3$, $R^{10}$, q, A and X are defined as above. These compounds are useful as intermediates for making compounds of Formula I and for inhibiting 5-lipoxygenase.

The present invention includes compounds of the formula IVa:

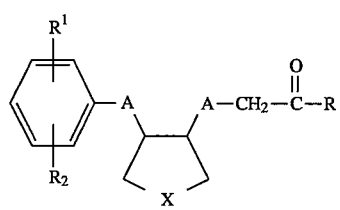
(IVa)

wherein $R^1$ and $R^2$ are the same or different and independently represent tert-butyl, phenyl or hydrogen; X is $(CH_2)_m$ wherein m is 1 or 2, A is S or O, with the two As being the same or different; and R is:

(a) OH;

(b) $OR^4$ wherein $R^4$ is alkyl of 1 to 4 carbon atoms; or (c) $NR^5R^6$ wherein $R^5$ is hydrogen or alkyl of 1 to 4 carbon atoms and $R^6$ is alkyl of 1 to 4 carbon atoms; hydroxyalkyl, alkoxyalkyl; heterocyclealkyl wherein the alkyl moiety has 1 to 4 carbon atoms; phenyl; substituted phenyl having one or more substituents selected from the group consisting of alkyl, hydroxy, alkoxy, halogen, alkylamino, dialkylamino, phenyl, and alkyl carbonyl; or Alk-$NR^8R^9$ wherein Alk is straight or branched chain alkyl of 1 to 4 carbon atoms and $R^8$ and $R^9$ are each independently hydrogen or alkyl of 1 to 4 carbon atoms;

and the pharmaceutically acceptable salts thereof.

Included in the present invention are compounds of formula IVa wherein $R^1$ and $R^2$ are both tert-butyl; and R is:

(a) OH;

(b) $OR^4$ wherein $R^4$ is alkyl of 1 to 2 carbon atoms; or (c) $NR^5R^6$ wherein $R^5$ alkyl of 1 to 4 carbon atoms and $R^6$ is hydroxyalkyl, alkoxyalkyl, heterocyclealkyl wherein the alkyl moiety has 1 to 4 carbon atoms, phenyl, substituted phenyl, or Alk-$NR^8R^9$ wherein Alk is alkyl of 1 to 4 carbon atoms and $R^8$ and $R^9$ are alkyl of 1 to 4 carbon atoms;

and the pharmaceutically acceptable salts thereof.

Compounds of the present invention can possess one or more asymmetric atoms and are thus capable of existing in the form of optical isomers as well as in the form of racemic or nonracemic mixtures thereof. The optical isomers can be obtained by resolution of the racemic mixtures by conventional processes. Included in the family of compounds of the present invention are all isomeric forms thereof, including diastereoisomers, geometric isomers, equatorial or axial isomers, conformers, tautomers, and their pharmaceutically acceptable salts.

(2) Definitions

For purposes of clarity, the terms and phrases used throughout this specification and the appended claims are defined in the manner set forth directly below.

Some of the chemical structures which are presented in this specification and the appended claims have been drawn using the convention which employs lines to represent alkyl radicals, which is known by those of skill in the art.

The abbreviation "Ac" or the term "acetyl" as used herein means

The term "alkoxy" as used herein means an alkyl radical, as defined herein, having an oxygen atom attached thereto. Representative alkoxy groups include methoxy, ethoxy, propoxy, tert-butoxy and the like.

The term "alkoxyalkyl" as used herein refers to an alkoxy group, as defined above, which is a substituent on an alkyl group, as defined below.

The term "alkyl" as used herein defines straight or branched chain monovalent hydrocarbon radicals having between about 1 to about 10 carbon atoms, within which includes from about 1 to about 6 carbon atoms, and further within which includes from about 1 to about 3 carbon atoms. Representative alkyl radicals include, for example, methyl, ethyl, propyl, isopropyl, butyl, t-butyl, sec-butyl, isobutyl, pentyl, 1-methylbutyl, isopentyl, neopentyl, hexyl, octyl, nonyl, decyl, t-pentyl, etc.

The term "alkylthio" as used herein means an alkyl group, as defined above, having a sulfur atom attached thereto.

The term "amino" as used herein means an $-NH_2$ group.

The term "animal" as used herein includes mammals and nonmammals, and further includes humans and nonhuman mammals.

The term "carbonyl" as used herein means a

group.

The term "carboxy" as used herein means a

group.

The term "composition" as used herein means a product which results from the combining of more than one element or ingredient.

The term "cycloalkyl" refers to cycloalkyl rings of 3 to 10 carbon atoms within which includes from 3 to 7 carbon atoms, and further within which includes 3, 4, 5 or 6 carbon atoms. Representative cycloalkyls include, but are not limited to, cyclopropyl, cyclobutyl, cyclopentyl, cyclohexyl, cycloheptyl, cyclooctyl, adamantane, norbornane and the like, which may optionally be substituted by 1 or more substituents selected from alkyl, hydroxy, alkoxy, and halogen.

The abbreviation "DMF" as used herein means dimethylformamide.

The abbreviation "DSC" as used herein means Differential Scanning Colorimetry.

The term "halogen" refers to chlorine, bromine, fluorine, and iodine.

The term "heteroatom" as used herein means an atom of any element other than carbon or hydrogen.

The terms "heterocycle" and "heterocyclic ring" as used herein refer to aromatic or nonaromatic single or benzofused heterocyclic rings which contain one, two, three or four heteroatoms selected from nitrogen, oxygen and sulfur, and include but are not limited to pyridine, piperazine, piperidine, pyrrolidine, pipecoline, dioxolane, furyl, thiopene, tetrahydrofuryl, morpholine, azabicycloalkyl, e.g., 3-azabicyclo[3,2,2]nonane, azatricycloalkyl, 1,2,3,4-tetrahydroisoquinoline, 5,6,11,12-tetrahydrodibenz[b,f] azocine, iminostilbene, and the like which may optionally be substituted with one or more substituents selected from alkyl, phenyl, substituted phenyl, phenylalkyl, heterocycle, cycloalkyl, halogen, hydroxy, nitro, trifluoromethyl and lower alkoxy.

The term "heterocyclealkyl" as used herein means heterocycle, as defined herein, having an alkyl group, as defined herein, attached thereto, which may optionally be substituted with one or more substituents selected from alkyl, phenyl, substituted phenyl, phenylalkyl, heterocycle, cycloalkyl, halogen, hydroxy, nitro, trifluoromethyl and lower alkoxy.

The abbreviation "HPLC" as used herein means High Pressure Liquid Chromatography.

The term "hydroxy" as used herein means the group $-OH$.

The term "hydroxyalkyl" as used herein means a hydroxy group, as defined above, which is a substituent on an alkyl group, as defined above, the hydroxyalkyl group being chemically stable.

The abbreviation "NMR" as used herein means Nuclear Magnetic Resonance.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laureate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The expression "pharmaceutically acceptable salts" is intended to include those salts capable of being formed with the compounds of the present invention, e.g., when R represents OH, $NR^5R^6$ when $R^6$ is $Alk-NR^8R^9$ or heterocyclealkyl without materially altering the covalent chemical structure thereof. Such salts include inorganic and organic base or acid addition salts, such as sodium, potassium, calcium, ammonium, alkylammonium, quaternary ammonium, triethanolamine, lysine, hydrochloride, hydrobromide, phosphate, citrate, etc. well known to those skilled in the art. The foregoing salts are prepared in the conventional manner by neutralization of the compounds of formula I with the desired base or acid.

The terms "substituted phenyl" and "substituted phenylalkyl" as used herein refer to phenyl or phenylalkyl moieties in which the phenyl ring is substituted by one or more substituents selected from alkyl, hydroxy, alkoxy, halogen, amino, alkylamino, dialkylamino, cycloalkyl, phenyl, substituted phenyl, trifluoromethyl, nitro, alkylthio, and alkyl carbonyl.

The abbreviation "t-Bu" as used herein means tert-butyl.

The term "tert-alkyl" as used herein in reference to $R^1$ and $R^2$ refers to branched chain alkyl moieties of from about 4 to about 10 carbon atoms having a tertiary carbon atom attached to the phenyl ring substituted by $R^1$ and $R^2$. Examples of such groups are tert-butyl, i. e., 1,1-dimethylethyl, 1,1-dimethylpropyl, 1-methyl-1-(ethyl) pentyl, 1,1-diethylpropyl, 1-ethyl-1-(propyl) butyl and the like.

The phrase "therapeutically-effective amount" as used herein means an amount of a compound, material, or composition which is an effective dose for eliminating or ameliorating pain in an animal, or for producing some other desired therapeutic effect, at a reasonable benefit/risk ratio applicable to any medical treatment.

The phrases "title compound," "title product" and "title material" as used herein mean that compound, product or material whose chemical name is given, and/or whose structure is shown, in the particular example, or subpart thereof, referred to. If no particular example, or subpart thereof, is referred to, it means that compound, product or material whose chemical name is given, and/or whose structure is shown, in the particular example, or subpart thereof, in which it appears.

(3) Dosage and Mode of Administration

The compounds of the present invention can be administered to a patient in such oral dosage forms as tablets, capsules, pills, powders, granules, elixirs, or syrups as well as aerosols for inhalation. Likewise, administration may be effected intravascularly, subcutaneously, topically, or intramuscularly using dosage forms known to those of ordinary skill in the pharmaceutical arts. In general, the preferred form of administration is oral. An effective but non-toxic amount of the compound is employed in treatment. The dosage regimen utilizing the present compounds is selected in accordance with a variety of factors including the type, age, weight, sex, and medical condition of the patient, the severity of the condition to be ameliorated, and the route of administration. A physician of ordinary skill can readily determine and prescribe the effective amount of the drug required to prevent, treat or arrest the progress of the condition. For those conditions in which it is desirable to inhibit superoxide generation, or for those conditions in which it is desirable to stimulate superoxide generation, the effective amount for administration is ordinarily that amount which is required to assure that the mammalian neutrophils involved in the generation of superoxide will be exposed to a sufficient concentration of drug to either inhibit superoxide generation or stimulate superoxide generation, as the case may be.

Dosages of the compounds of the present invention, will range generally between 0.1 mg/kg/day to about 100 mg/kg/day, and preferably between about 0.5 mg/kg of body weight per day to about 50 mg/kg of body weight per day, when administered to patients suffering from inflammation or allergic or hypersensitivity reactions. In general, a unit dose form of the compounds of the invention will contain from about 1.75 to about 750 mg of compound. The compound may be administered in divided dosages, e.g. two or more times daily. The compounds may also be administered transdermally or topically to treat proliferative skin conditions such as psoriasis. The daily dosage may be administered in a single dose or in equal divided doses three or four times daily.

Unit dosage forms such as tablets and capsules can contain any suitable, predetermined, therapeutically effective amount of one or more active agent and a pharmaceutically acceptable carrier or diluent. Generally speaking, solid oral unit dosage forms and other unit dosage forms of the compounds of this invention which inhibit cyclooxygenase and/or 5-lipoxygenase will contain from 1.75 to 750 mg per tablet of drug as the effective 5-lipoxygenase and/or cyclooxygenase inhibiting amount of the compound.

In the case of acute allergic or hypersensitivity reactions, it is generally preferable to administer the initial dosage via the parenteral route and continue parenteral administration until the patient is stabilized, and can be maintained, if necessary, on oral dosing.

In the case of psoriasis and other skin conditions, it may be preferred to apply a topical preparation of a compound of this invention to the affected area three or four times daily.

In treating asthma and arthritis with a compound of this invention, the compounds may be administered either on a chronic basis, or as symptoms appear. However, in the case of arthritis and other inflammatory conditions which can lead to deterioration of joints and malformations, it is generally preferable to administer the active agent on a chronic basis.

When the compounds of this invention are co-administered with one or more cyclooxygenase inhibitors, they may conveniently be administered in a unit dosage form or may be administered separately. When the patient is allergic or hypersensitive to the cyclooxygenase inhibitor, it is preferred to initiate therapy with a compound of this invention prior to administration of the cyclooxygenase inhibitor.

A typical tablet of this invention can have the following compositions:

| Ingredient | Mg/tablet |
| --- | --- |
| Active ingredient | 100 |
| Starch, U.S.P. | 57 |
| Lactose, U.S.P. | 73 |
| Talc, U.S.P. | 9 |
| Stearic acid | 12 |

In the pharmaceutical compositions and methods of the present invention, at least one of the active compounds of the invention, or a pharmaceutically acceptable salt thereof, will typically be administered in admixture with suitable pharmaceutical diluents, excipients, or carriers (collectively referred to herein as "carrier" materials) suitably selected with respect to the intended form of administration, that is, oral tablets, capsules, elixirs, syrups, and the like, and consistent with conventional pharmaceutical practices. For instance, for oral administration in the form of tablets or capsules, the active drug component may be combined with any oral non-toxic pharmaceutically acceptable inert carrier such as lactose, starch, sucrose, cellulose, magnesium stearate, dicalcium phosphate, calcium sulfate, mannitol and the like; for oral administration in liquid form, the active drug component may be combined with any oral non-toxic pharmaceutically acceptable inert carrier such as ethanol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes. Lubricants for use in these dosage forms include boric acid, sodium benzoate, sodium acetate, sodium chloride, and the like. Disintegrators include, without limitation, starch, methylcellulose, agar, bentonite, guar gum, and the like.

(4) Methods of Preparation

In general, the compounds of the present invention may be prepared by the methods illustrated in the following general reaction schemes, or by modifications thereof, from readily available starting materials by any of the following alternate processes in a conventional manner. Unless otherwise specified, the various substituents of the compounds are defined in the same manner as they are defined hereinabove in Formulas I, Ia, Ib, II, IIa, IIb, III, IVa and XV.

If a particular enantiomer of a compound of the present invention is desired, it may be prepared by chiral synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The following reaction schemes describe methods which can be employed for preparing the compounds of formula I, including starting materials, intermediates, and reaction conditions.

As shown in part (1) of Scheme A, a mercaptan (V) or alcohol or a phenol or a thiophenol can be reacted with an oxabicyclo compound (VI) to give the intermediate (III), which may then be reacted with a monohaloacid or protected monohaloacid in a base or, alternatively, with a thiol acid in an acid to obtain a product acid of type (VII). Epoxides of type (VI) are readily prepared by oxidation of a double bond with peroxides such as m-chloro-perbenzoic acid, peracetic acid, pertrifluoroacetic acids, hydrogen peroxide, t-butyl hydroperoxide and the like. Base induced cyclization of halohydrins, obtained by treatment of double bonds with mineral acids, also produces epoxides. In addition, epoxides can be used as starting materials for the preparation of halohydrins, which can also be used to produce compounds of type III, following reaction with, for example, a mercaptan. Most bases can be used for the preparation of III, for example, hydroxides, tert-amines, heterocyclic amines, dimethylaminopyridines, hydrides, lithium alkyls, lithium amides and the like, since the thiolate anion is an exceptional nucleophile. Non-nucleophilic bases are preferred for the conversion of III into VII in the presence of an electrophilic reagent, such as a substituted halo alkyl group.

Epoxides of Formula VI can be converted into thioepoxides (the sulfur analog) by, for example, the method described by E. E. Van Tamelin, *ORGANIC SYNTHESIS COLLECTED VOLUME* 4, p. 232 (1963), which is incorporated herein by reference. Thioepoxides can be used in place of epoxides allowing the order of addition of substituents to be varied, especially in the case where the right-hand A of formula VII is sulfur.

Compound III may also be converted into VII via conversion into a halo compound (Scheme C), an activated ester (Scheme C) or on an acid catalysis (Scheme A). In the first case, treatment of the hydroxy compound with hydrochloric, hydrobromic, hydriodic or hydrofluoric acid, preferably at reflux temperatures, converts it into the corresponding halo compound. Displacement of the halogen ($SN_2$) with a mercaptan under basic conditions (as shown in Scheme B) provides compound XIII.

The alcohols III or XI may be converted into activated esters, such as those of toluene sulfonic acid (tosylates), methane sulfonic acid (mesylates), trifluoromethane sulfonic acid triflates) and trifluoroacetic acid. Displacement of the activated ester ($SN_2$) with a mercaptan under basic conditions (see above) provides compound VII. Both this method and that outlined above utilizing a halo intermediate have the advantage that the stereochemistry at the carbon bearing the functional group may be inverted, thus allowing control (selection) of the stereochemistry of the product.

Treatment of alcohols III (A=S) or XI with a mercaptan in the presence of an acid (Scheme A, B, C) should provide the corresponding sulfide, e.g., VII or XIII. Mineral acids, organic acids and Lewis acids are suitable for this reaction. Non-nucleophilic acids are preferred and include, for example, trifluoroacetic acid, toluene sulfonic acid, perfluorobutyric acid, triflic acid, phosphoric acid, sulfuric acid, boron trifloride, aluminum chloride and the like.

Conversion of a carboxylic acid such as VII, XI or XII into an ester or an amide is accomplished by standard means. The carboxylic acid may be treated with the appropriate alcohol with or without added solvent in the presence of an acid (see above) to provide the product ester. A salt of the carboxylic acid may be prepared by treatment with a base (see above) and the salt then treated with an electrophilic group with displacement of, for example, a halide, tosylate and the like. An alternative method of preparation is conversion of the carboxylic acid into an activated carbonyl function such as an acid halide, mixed anhydride or activated ester followed by treatment with an appropriate alcohol or amine. Acid halides can be made by mixing, for example, thionyl chloride, thionyl bromide, phosphorus trichloride, phosphorus pentabromide, oxalyl chloride and the like with the acid. Mixed anhydrides with, e.g., isobutyl chloroformate, are prepared in the standard manner with the acid being treated with isobutyl chloroformate in the presence of a base or from a preformed carboxylate salt. The same type of salt, either prepared in the reaction or preformed, can be treated with for example, N-chlorosuccinimide, to form the succinimide activated ester. Treatment of either of these intermediates with the appropriate amine, alcohol, mercaptan or electrophile will provide the compounds of this invention.

The conversion of the alcohols/mercaptans III, XI, XVI, XVII and the like into compounds of, for example, X, is accomplished in the same manner as the synthesis of the other esters outlined above. In this case, the appropriate alcohol/mercaptan is represented as outlined above and the acylating agent can be an acid halide or anhydride.

Scheme C illustrates yet another method for the preparation of the intermediates and compounds of this invention. An alpha-halo ketone, substituted or unsubstituted, is treated with a oxygen or sulfur nucleophile generated as described above. The valuable intermediate, XV, is reduced directly with, for example, a hydride reducing agent such as sodium borohydride, lithium aluminum hydride, sodium cyano borohydride and the like or borane, to provide the alcohols III and XI. The use of these intermediates for the preparation of compounds VII, VIII, IX and X is discussed above. Conversion of ketone XV into a thioketone is readily accomplished using reagents such as phosphorus pentasulfide or 2,4-bis(4-methoxyphenyl)-1,3-dithia-2,4-diphosphetane-2, 4-disulfide (Lawesson's Reagent). Reduction of the thioketone as discussed above for the ketones provides the mercaptan analogs of III and XI and it is used similarly.

The sulfone and sulfoxide compounds of the present invention are readily prepared by oxidation of the sulfides with, for example, m-chloroperoxybenzoic acid or sodium metaperiodate.

Racemic Compound VII produced by the above Schemes A, B, and C may be resolved to their single enantiomers by the procedures illustrated in Scheme D. Schemes A and C provide for the synthesis of racemic cis and racemic trans alcohols III. Treatment of either the racemic cis or racemic trans alcohol with an acetylating agent, such as vinyl acetate or isopropenyl acetate, in the presence of an appropriate enzyme, such as AMANO Lipase PS30, results in the selective acetylation of one of the constituent enantiomeric alcohols, leading to a crude product consisting of essentially enantiomerically pure acetate and essentially enantiomerically pure alcohol (enantiomer A). Appropriate enzymes include, but are not limited to, lipases, cholinesterases and proteases. The reaction may be monitored to complete acetylation of one of the enantiomers using HPLC. The enantiomerically pure alcohol (Enantiomer A) may be separated from enantiomerically pure acetate by column chromatography. Saponification of the acetate using aqueous base provides the other enantiomerically pure alcohol (Enantiomer B). Conversion of these alcohols to enantiomerically pure acids VII is effected by treatment with a haloalkyl carboxylic acid or its salt, such as sodium chloroacetate, in the presence of a base as shown in Scheme A.

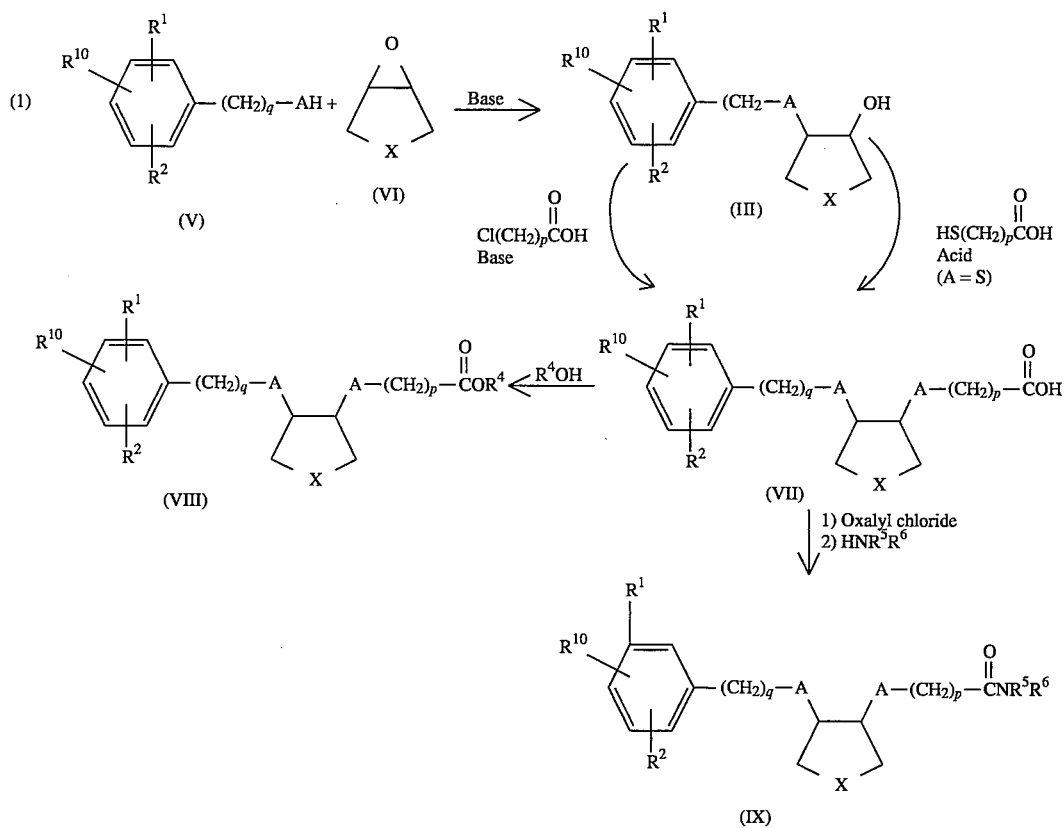

SCHEME A

SCHEME A
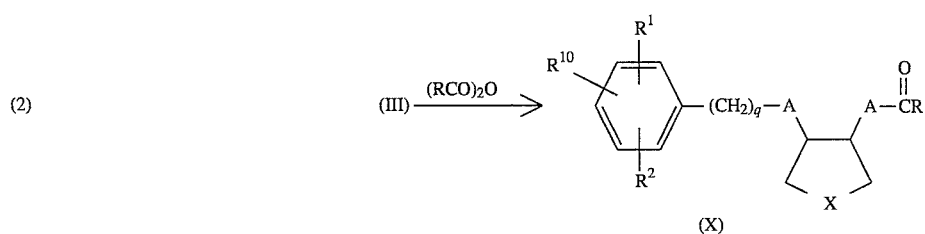
R = alkyl or $(CH_2)_t COOR^7$
A = O or S
SCHEME B
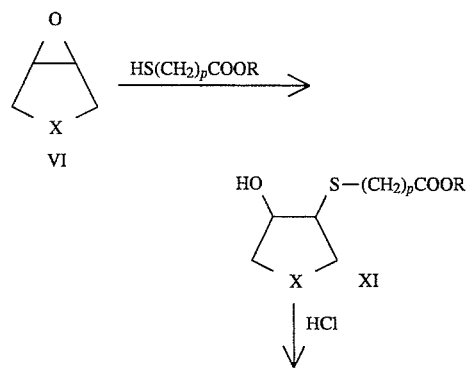
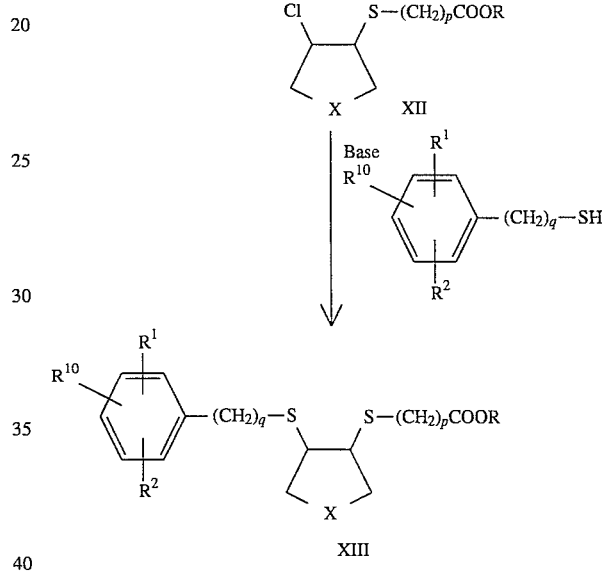
SCHEME C
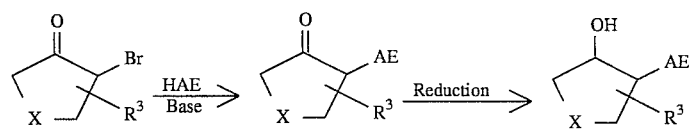
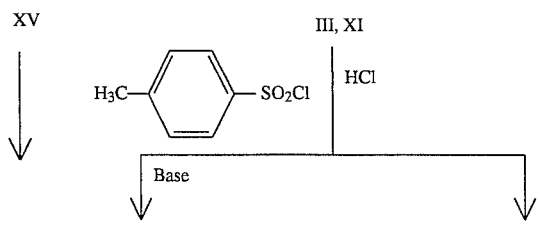

-continued
SCHEME C
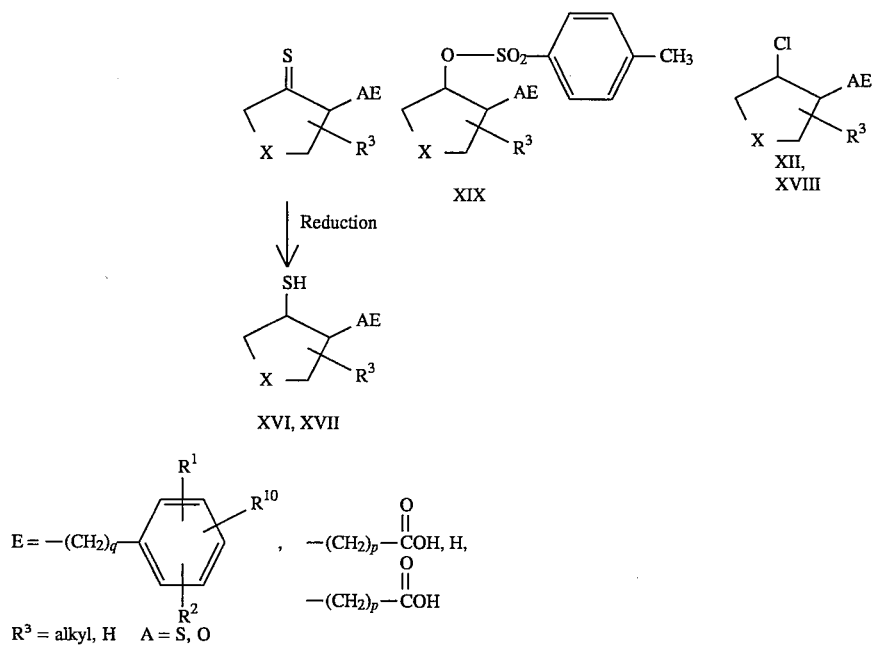
SCHEME D
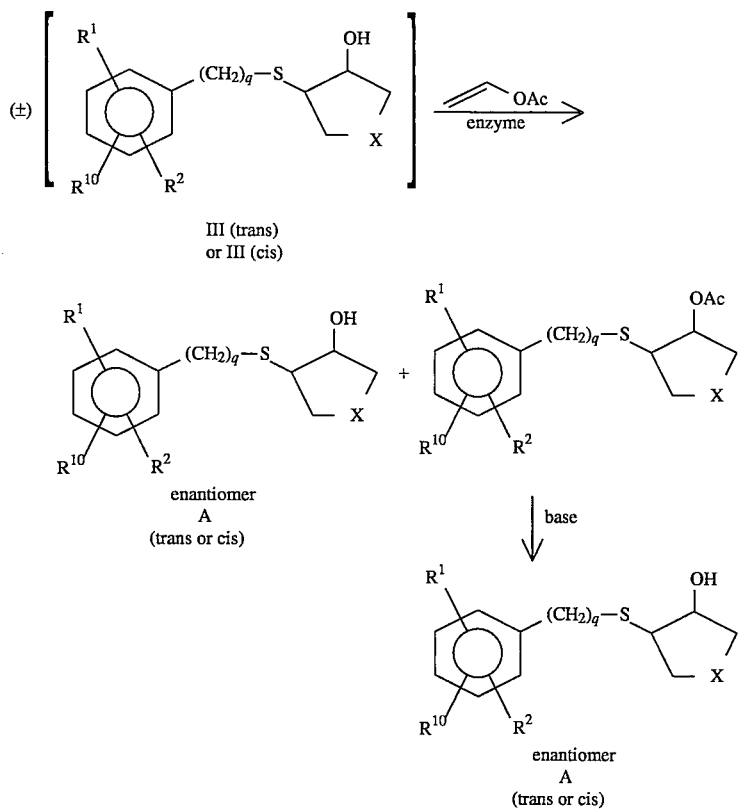

The conditions for carrying out the individual steps in each of the general reaction schemes presented above are conventional, well-known, and capable of wide variation.

Other methods known in the art can also be used to synthesize the compounds of the present invention.

(5) Biological Evaluations

The compounds of the present invention are evaluated with respect to superoxide modulating activity according to the following assay procedure:

Human neutrophil superoxide generation:

Superoxide generation by formyl-methionyl-leucyl-phenylalanine (FMLP)-stimulated neutrophils was quantitated by the reduction of cytochrome C (Badwey, J. A., Curnutte, J. T. and Karnovsky, M. L., cis-Polyunsaturated fatty acids induce high levels of superoxide production by human neutrophils. *J. BIOL. CHEM.* 256: 12640–12643, 1981, which is incorporated herein by reference.) To 5 million neutrophils in 2.85 ml of Krebs-Ringer phosphate buffer, pH 7.2, 50 ul of inhibitor (in 10% DMSO/buffer), and 50 ul ferricytochrome C (5 mM, stock) were added and preincubated for 3 minutes at 37° C. Absorption measurements at 550 nm were recorded at start of preincubation. Fifty ul FMLP (6 uM, stock) was added to initiate reaction. A plateau was reached within 3 minutes and this reading minus the initial reading (before addition of FMLP) was used to calculate nanomoles of superoxide generated based on a molar extinction coefficient of $2.1 \times 10^4 \ cm^{-1}mole^{-1}$.

Isolation of human neutrophils:

Human neutrophils were isolated from freshly drawn blood of healthy donors. Two ml of 5% dextran (MW 200,000–300,000) in saline was added to 10 ml aliquots of blood, mixed and placed upright for 45 minutes at 37° C. Approximately 8–10 ml of the plasma-white cell suspension from the dextran sedimentation was layered on 3 ml of Ficol-paque in a 15 ml tube and centrifuged at 400 g for 30 minutes. The supernate, containing plasma and platelets, was discarded by aspiration, and the pellet, containing predominantly neutrophils, was resuspended in 1 ml of saline. The suspension was transferred to a clean tube, and pooled with other aliquots of blood treated similarly. The pooled suspension was centrifuged at 350 g for 5 minutes and the supernate was discarded. The pellet was resuspended in 5 ml of 0.05% NaCl with a plastic Pasteur pipette for 25 seconds to lyse contaminating red cells, then 5 ml of 1.75% NaCl was added to regain isotonicity. The red cell lysing procedure was repeated, the cells suspended in appropriate buffer (depending on assay) and counted.

The compounds of the present invention evaluated with respect to cyclooxygenase inhibition according to the following assay procedure.

Inhibition of Sheep Seminal Vesicle Microsome Cyclooxygenase:

This assay was based on oxygen consumption during conversion of arachidonic acid to prostaglandin $G_2$ catalyzed by cyclooxygenase *BIOCHEM.* 11:3276–3285 (1972), which is incorporated herein by reference. Lyophilized ovine microsome (approximately 1 mg) suspended in 2.9 ml Tris-HCl buffer, pH 8.2, containing 0.7 mM phenol were used as source of arachidonate cyclooxygenase. The inhibitor, 50 μl in DMSO, was added and the mixture was preincubated for 5 minutes at 37° C. Fifty μl of arachidonic acid (final concentration 50 μM) was added to start the reaction. The slopes of the initial rates of oxygen uptake, in the presence and absence of inhibitor, were compared to determine reaction inhibition. Percent inhibition was computed using the following formula:

$$\% \ \text{Inhib.} = \frac{I.S.^* \ (\text{control}) - I.S. \ (\text{inhib.})}{I.S. \ (\text{Control})} \times 100$$

*I.S. = initial slope.

The compounds of the invention are evaluated with respect to 5-lipoxygenase inhibition according to the following assay procedure.

Inhibition of 5-lipoxygenase, in vitro:

The 100,000×g supernatant fraction of Rat Basophilic Leukemia Cell Homogenate (RBL-1) serves as a 5-lipoxygenase enzyme source. The enzyme is incubated with [$1-^4C$]-arachidonic acid and Ca++ in the presence and absence of test compound. The product of 5-lipoxygenase, 5-hydroxyeicosatetraenoic acid (5-HETE), is separated by thin-layer chromatography and measured by radioactivity. A compound inhibiting 5-HETE synthesis by 30% or more is considered active at that concentration. Initial screening doses are $1\times10^{-4}M$. When the compound inhibits more than 50% of 5-HETE synthesis at $10^{-4}M$, that compound is tested at multiple dose levels to determine the $IC_{50}$ value (inhibitory concentration to inhibit 50%).

For comparison the compound of Formula XX, a known 5-lipoxygenase inhibitor described in U.S. Pat. No. 4,755,524 was used:

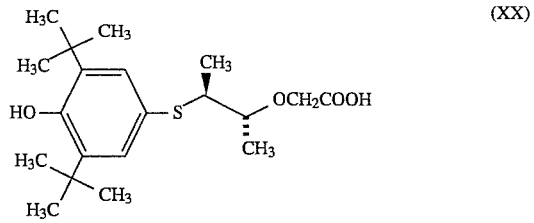

(XX)

(±)[2S*-[[3,5-bis(1,1-dimethylethyl)-4-hydroxyphenyl]thio]-1R*-methylpropoxy]acetic acid.

The compounds of the invention are evaluated with respect to COX-I and COX-II activity in vitro using an enzyme based assay according to the following assay procedure.

Commercially available nonsteroidal anti-inflammatory drugs are believed to work through the inhibition of COX-I and COX-II activity in vivo to block local proinflammatory prostaglandin production, often at the site of tissue injury.

(a) Preparation of Recombinant COX Baculoviruses

A 2.0 kb fragment containing the coding region for either human or murine COX-I (Caymen Chemical, Ann Arbor, Mich.), or human or murine COX-II (Caymen Chemical, Ann Arbor, Mich.), was cloned into a BamH1 site of the baculovirus transfer vector pVL1393 (Invitrogen, Palo Alto, Calif.) to generate a baculovirus transfer vector. Recombinant baculoviruses were isolated by transfecting 4 μg of baculovirus transfer vector DNA into SF9 cells (2×10e8) (Invitrogen, Palo Alto, Calif.) along with 200 ng of linearized bacium by the phosphate method. See M. D. Summers et al., "A Manual of Methods for Baculovirus Vectors and Insect Cell Culture Procedure," *TEXAS AGRICULTURE EXPERIMENTAL STATION BULLETIN*, No. 1555 (1987), which is incorporated herein by reference. Recombinant viruses were purified by three rounds of plaque purification, and high titer (10e7–10e8 pfu/ml) stocks of virus were prepared. For large scale production, SF9 insect cells (Invitrogen, Palo Alto, Calif.) were infected in 10 liter fermentors (0.5×10⁶/ml) with the recombinant baculovirus stock, such that the multiplicity of infection was 0.1. After 72 hours, the cells were centrifuged and the cell pellet was homogenized in Tris/Sucrose (50 mM: 25%, pH 8.0) containing 1%

CHAPS. The homogenate was centrifuged at 10,000×G for 30 minutes, and the resultant supernatant was stored at −80° C. before being assayed for COX activity.

b. Assay for COX-I and COX-II activity:

COX activity was assayed as $PGE_2$ formed/μg protein/time using an ELISA (Caymen Chemical, Ann Arbor, Mich.) to detect the prostaglandin $E_2$ released. CHAPS-solubilized insect cell membranes containing the appropriate COX enzyme were incubated in a potassium phosphate buffer (50 mM, pH 8.0) containing phenol (0.5 mM), and heme (1 μM) with the addition of arachidonic acid (10 μM). Compounds of the present invention were pre-incubated with the enzyme for 10–20 minutes prior to the addition of the COX-I and COX-II enzyme substrate arachidonic acid (10 μM). Any reaction between the arachidonic acid and the enzyme was stopped after ten minutes at 37° C./room temperature by transferring 40 μl of reaction mix into 160 μM ELISA buffer and 25 μM indomethacin. The $PGE_2$ formed was measured by standard ELISA technology (Cayman Chemical, Ann Arbor, Mich.).

The results of this assay are presented in Table 1 hereinbelow. The results for this assay, as well as for the next assay (COX-II Cell Fibroblast Assay) are expressed in terms of COX-I or II activity as an $IC_{50}$ value (50% inhibitory concentration), as defined as the amount of prostaglandin $E_2$ ($PGE_2$) formed per protein per time in response to the enzyme substrate arachidonic acid.

The compounds of the invention are evaluated with respect to the inhibition of cellular COX-II in vitro according to the following Cellular COX-II Assay (Cell Fibroblast Assay).

Cellular COX-II Assay (Cell Fibroblast Assay)

Inhibition of cellular COX-II by test compounds is determined using stimulated human fetal dermal fibroblasts (HFDF, derived from primary cell cultures). Fibroblasts are cultured in microtiter wells at $1.5 \times 10^4$ cells/well in Dulbecco's Modified Eagle's Media (DMEM)(Gibco/BRL, Gaithersburg, Md. Sigma Chemical Co., St. Louis, Mo.) containing 4500 mg glucose/L, 100 units penicillin G/ml and 0.1 mg streptomycin/ml, 4 mM L-glutamine, 25 mM Hepes and 10% Fetal Bovine Serum (Gibco/BRL, Gaithersburg, Md. Bioproducts For Science, Inc., Indianapolis, Ind.). Following a 3-day incubation at 37° C., the culture media is removed by aspiration using low vacuum, and the cells are stimulated overnight with medium containing human recombinant IL-1 (interleukin-1) beta (1 ng/ml)(Cistron, Pine Brook, N.J.). The next day, the fibroblasts are washed with Phosphate Buffered Saline, and 185 μl of DMEM is added to each well. The cells are placed in a 37° C. incubator for 15 minutes. Compounds are then added to the cells using seven half-log dilutions in duplicate determinations. Cells are incubated with test compounds at 37° C. for 30 minutes. The COX-II substrate arachidonic acid (20 μM; Nu-Chek-Prep Inc., Elysian, Minn.) is then added to the cell cultures and the plates are incubated for 10 minutes at 37° C. Supernatants are collected and Prostaglandin $E_2$ ($PGE_2$) production is measured by an enzyme-linked immunosorbent assay (ELISA; antibodies produced by Cayman Chemical Company, Ann Arbor, Mich.). Compounds which exhibit activity in this assay inhibit $PGE_2$ production.

The following is a description of how the activities of the compounds of the present invention may be determined.

A run of this assay consists of one (or more) plates, each containing, along with the standard (in row A), (1) two wells of unstimulated material (in col. 12), (2) five wells of stimulated material (in col. 12), (3) seven wells (one per concentration) for indomethacin (in col. 11), and (4) two wells at each of seven concentrations for five test compounds, one of which is a repeat of indomethacin. The response (ng/ml Eicosanoid) is estimated from the Standard curve and is highest at low concentrations and decreases as the concentration increases. If the response is plotted on the y-axis and the log of the concentration is plotted on the x-axis, the dose-response pattern for these assays is typically a symmetrical, sigmoidal shaped curve. If a full range of concentrations is used, the complete sigmoidal curve may be seen, starting with an upper asymptote, falling at some degree of steepness, and then leveling off at a lower asymptote. The $IC_{50}$ is defined as the concentration corresponding to a response midway between the upper and lower plateaus. A theoretic "dose-response" model is used to estimate the $IC_{50}$.

The procedure described below was used to define the minimum and maximum responses for the compounds on a plate.

The procedure uses information for indomethacin and the rest of the plate in defining the minimum and maximum response. The justification for doing this is as follows. Enough runs have been done with indomethacin to determine and use a range of concentrations such that the response to the lowest concentrations is on the upper plateau of the sigmoidal curve and the response to the highest concentrations is on the lower plateau of the sigmoidal curve. For the other compounds, if a response is measured which is less than the response for the unstimulated wells, then this response may be considered to be another estimate of a minimal response. Likewise, if a response is measured which is greater than the response for the stimulated wells, then this response may be considered to be another estimate of a maximal response. Based on this reasoning, the minimum is estimated as follows:

1) For each compound, including indomethacin (col. 11), identify the smallest dup average,
2) If the compound is indomethacin (col. 11), mark this response for use,
3) If the compound is not indomethacin and the response is less than the average of the unstimulated wells, mark this response for use,
4) Calculate the minimal response as the average of the unstimulated wells along with the dup averages marked for use in steps 2 and 3 above.

Likewise, the maximum is estimated as follows:

1) For each compound, including indomethacin (col. 11), identify the largest dup average,
2) If this largest dup average does not correspond to the lowest concentration, compute the mean of the dup averages for this concentration and all lower concentrations,
3) If the compound is indomethacin (col. 11), mark this response (or mean) for use,
4) If the compound is not indomethacin and the response (or mean) is greater than the average of the stimulated wells, mark this response for use,
5) Calculate the maximal response as the average of the stimulated wells along with the responses (or means) marked for use in steps 3 and 4 above.

Then, the model used to estimate the $IC_{50}$ is the four parameter logistic with two parameters fixed, the minimum and maximum. This mode is described in A. De Lean et al. "Simultaneous analysis of families of sigmoidal curves: application to bioassay, radioligand assay, and physiological dose-response curves", *AM. J. PHYSIOL.* 235(2): E97–E102, (1998), which is incorporated herein by reference. The formula for the four-parameter logistic model may be expressed as:

$$Y=((a-d)/(1+(X/c)**b)+d,$$

where Y is the response, X is the concentration, a is the lower asymptote, d is the upper asymptote, c is the $IC_{50}$ (in the same units as X), b is the slope and ** means exponent. For this assay, a is fixed at the minimum value and d is fixed at the maximum value as calculated above.

A nonlinear modeling procedure is used to estimate the two other parameters, the slope and $IC_{50}$. Nonlinear modeling requires the specification of starting values for each parameter to be estimated, and then, unlike linear modeling, an iterative procedure is required to improve on these initial estimates until no further improvement in the fit of the model to the observed data can be achieved (or the maximum number of iterations has been reached). The criteria for a good fit is least squares, i.e., the best fit is one for which the sum of the distance squared between each observed data point and the model at that same concentration is minimized (is least).

Two follow-up measures are provided to insure that the final solution is adequate. First, a plot of the observed data with the estimated model curve superimposed is created. Second, the value of the RMSEs (root mean squared errors) generated for each model fit by this assay is printed. A simplified description of the RMSE is that it is the average distance of the observed data from the model, in terms of counts per minute. (The RMSE is actually the square root of the sum of the distance squared between each observed data point and the model as determined by the final solution divided by the number of concentration levels minus 2.) Smaller values of RMSE indicate closer fits of the model to the observed data. Unusually large values of RMSE should be investigated.

For further details concerning this Cellular COX-II Assay (Cell Fibroblast Assay), see A. Raz et al., "Temporal and Pharmacological Division of Fibroblast Cyclooxygenase Expression into Transcriptional and Translational Phases," *PROC. NATL. ACAD. SCI., U.S.A.*, 86:1657–1661 (1989), which is incorporated herein by reference.

The results with respect to certain compounds of the present invention for the above-described assays are set forth in Table 1 below.

TABLE 1

| Compound Example Number | 5-Lipoxygenase Inhibition $IC_{50}$ (μM) | FMLP Induced Superoxide Generation | Cyclooxygenase Inhibition $IC_{50}$ (μM) | Human Enzyme Assay $IC_{50}$ (μM) COX-II | Human Enzyme Assay $IC_{50}$ (μM) COX-I | Cell Fibroblast Assay $IC_{50}$ (μM) |
|---|---|---|---|---|---|---|
| 4 | — | Stimulation 1 μM, 67% > control 10 μM, 133% > control 100/μM, 167% > control | — | — | — | — |
| 5 | 100 | Inhibition $IC_{50}$ = 1.1 μM | 3.1 | — | — | — |
| 7 | Stimulated 45% at $10^{-4}$M Stimulated 27% at $10^{-5}$M | Inhibition $IC_{50}$ = 50 μM | Inactive at 100 μM | — | — | — |
| 11 | Stimulated 2.5% at $10^{-4}$M Stimulated 3.2% at $10^{-5}$M | Inhibition $IC_{50}$ = 4.8 μM | 2.9 | — | — | — |
| 15 | Inhibited 21.3% at $10^{-4}$M Inhibited 14.9% at $10^{-5}$M | Inhibition $IC_{50}$ = 2.8 μM | 64.0 | — | — | — |
| 16 | 100 | Stimulation 10 μM, 33% > control 25 μM, 83% > control 50 μM, 100% > control | — | — | — | — |
| 17 | >100 | Inhibition $IC_{50}$ = 3.4 μM | 3.8 | — | — | — |
| 72 | >100 | | | 4.11 | >100 | 0.37 |
| 76 | | | | >100 | >100 | 5.595 |
| 77 | | | | 5.16 | >100 | 0.17 |
| 80 | | | | 0.937 | 28.467 | 0.602 |
| 81 | | | | 1.43 | 94.6 | 0.438 |
| 84 | | | | 3.7 | >100 | 0.42 |
| 85 | | | | 2.5 | >100 | 0.163 |
| 89 | | | | 3.405 | >100 | 0.576 |
| 92 | | | | 3.883 | >100 | 0.246 |

TABLE 1-continued

| Compound Example Number | 5-Lipoxygenase Inhibition IC$_{50}$ (µM) | FMLP Induced Superoxide Generation | Cyclooxygenase Inhibition IC$_{50}$ (µM) | Human Enzyme Assay IC$_{50}$ (µM) COX-II | Human Enzyme Assay IC$_{50}$ (µM) COX-I | Cell Fibroblast Assay IC$_{50}$ (µM) |
|---|---|---|---|---|---|---|
| 93 | | | | 7.655 | >100 | 0.334 |
| 97 | | | | 1.995 | 92.05 | 0.227 |
| 99 | | | | 0.54 | >100 | 0.449 |
| 101 | | | | >100 | >100 | 0.84 |
| Formula XX | 4.9 | Inhibition ID$_{50}$ = 11 µM | — | — | — | — |

— = not tested

The compound of Formula XX inhibited both superoxide generation and 5-lipoxygenase, whereas the compound of Example 16 inhibited 5-lipoxygenase and stimulated superoxide generation. This data indicates that superoxide generation is not dependent on 5-lipoxygenase, and that the ability of a compound to inhibit 5-lipoxygenase is not related to its ability to simulate superoxide generation.

The compound of Example 7, which has no substituents on the phenyl ring (i.e., $R^1$ and $R^2$=H), did not inhibit either 5-lipoxygenase or cyclooxygenase, but did inhibit superoxide generation.

Complement C5a induced superoxide generation may also be stimulated or inhibited by compounds of the present invention.

Chronic adjuvant-induced polyarthritis test:

Rats [50–70 gm] were weighed, ear tagged and intradermally inoculated in the tail base with 2.0 mg of heat killed M. butyricum suspended in 0.05 ml of white paraffin oil [n=12–15 per group]. Compounds were intragastrically administered beginning on the day of inoculation and continued for 18 days. Each daily dose was split [dose volume= 0.5 ml/100 gm] and given approximately 7 hours apart. Animals were weighed every 3 days, and the dose was adjusted accordingly. On day 19, animals were sacrificed by inhalation of $CO_2$, weighed, and total hind paw volume was measured by the displacement of water with a plethysmometer (Ugo Basile, Varese, Italy). A group of age-matched naive rats were included. These rats, designated "normal," were not inoculated with adjuvant or gavaged with vehicle.

Statistical Analysis:

For individual experiments, the paw volume/body weight ratios for each dose were compared to the ratio for the vehicle treated control group by a two-tailed Dunnett's t-test (p $\leq$ 0.05). The Dunnett's test was preceded by a Bartlett's test of variance homogeneity across the dose groups. If the Bartlett's test was significant, an appropriate variance stabilizing transformation was applied to the data, and the Dunnett's test was performed on the transformed data.

TABLE 2

Chronic Adjuvant-Induced Polyarthritis Minimum dose to result in a statistically significant reduction [p < 0.05] in the paw volume/body weight ratio

| Compound Example No. | Dose [mg/kg/day] | % Inhibition[1] |
|---|---|---|
| Ex. 5 | 25 | 64.4 |
| Ex. 17 | 25 | 50.8 |

[1] % Inhibition in the paw volume to body weight ratio.
% Inhibition = [1-[(compound treated − normal) + (vehicle treated − normal)]] × 100

While the invention has been described and illustrated with reference to certain preferred embodiments thereof, those skilled in the art will appreciate that various changes, modifications, and substitutions can be made therein without departing from the spirit of the invention. These modifications and variations are within the scope of the invention as described and claimed herein. For example, effective dosages other than the preferred ranges set forth hereinabove may be applicable as a consequence of variations in the responsiveness of the mammal treated, severity of condition treated, dosage related adverse effects, if any, observed and analogous considerations. Likewise, the specific pharmacological responses observed may vary depending upon the particular active compounds selected or whether different active compounds are used in combination or in the presence of suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which are presented hereinbelow.

(6) EXAMPLES

The following non-limiting examples further describe and illustrate details for the preparation of the compounds of the present invention. Those skilled in the art will readily understand and appreciate that known variations of the conditions and procedures in the following preparative methods can be utilized.

In these examples, all temperatures are degrees Celsius unless otherwise noted. Melting points were determined on a Thomas-Hoover melting point apparatus or by DSC and are uncorrected.

Unless indicated otherwise in a particular example, all of the starting materials, and all of the equipment, employed in the examples are commercially available. Sources for these materials include Sigma Chemical Co. (St. Louis, Mo.), Aldrich Chemical Co. (Milwaukee, Wis.), Lancaster Synthesis (Windham, N.H.), Bioproducts For Science, Inc. (Indianapolis, Ind.), Fisher Scientific (Pittsburgh, Pa.), Boehringer Mannheim Biochemicals (Indianapolis, Ind.), Fluka Chemical Corp. (Ronkonkoma, N.Y.), TCI, American Tokyo Kasei, Inc. (Atlanta, Ga.), Chemical Dynamics Corp. (South Plainfield, N.J.), Amano International Enzyme Company, Inc. (Troy, Va.), Nu-Chek-Prep, Inc. (Elysian, Minn.), Caymen Chemical (Ann Arbor, Mich.), Cistron (Pine Brook, N.J.), Gibco/BRL (Gaithersburg, Md.) and Invitrogen (Palo Alto, Calif.). Most of the starting materials were obtained from Aldrich Chemical Co. (Milwaukee, Wis.). The syntheses of those starting materials which are not commercially available are described in the examples presented below.

All patents and publications referred to in the examples, and throughout the specification, are hereby incorporated herein by reference, without admission that such is prior art.

EXAMPLE 1

O-[3,5-bis(1,1-dimethylethyl)phenyl]dimethylcarbamothioate (1)

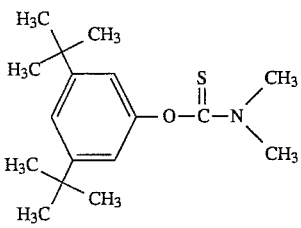

Potassium bis (trimethylsilyl) amide (15% by weight in toluene, 260 ml, 0.169 moles) was added by syringe to a solution of 3,5-di-tert-butylphenol (34.8 g, 0.169 moles) in tetrahydrofuran (500 ml). After 30 minutes, a solution of dimethylthiocarbamoyl chloride (24.7 g, 0.20 moles) in tetrahydrofuran (50 ml) was added over 10 minutes. The reaction mixture was stirred at room temperature for 30 minutes, and then at 50° C. for 1.5 hours. After cooling to room temperature, the reaction mixture was poured into cold (0° C.) water (100 ml) containing potassium hydroxide (30 g). The mixture was extracted twice with 1000 ml of ethyl ether. The combined ethyl ether extracts were dried over sodium sulfate, filtered and concentrated with a rotary evaporator to give the crude product as a yellow oil. The title product was purified by chromatography on silica gel and used directly in Example 2.

EXAMPLE 2

3,5-bis(1,1-dimethylethyl)benzenethiol (2)

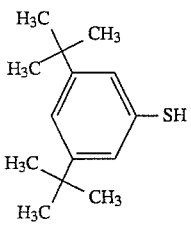

The title compound of Example 1 (42 g, 0.143 moles) was heated to 300° C. in a round bottom flask with a heating mantle for 2 hours. After cooling to room temperature, the material was dissolved in ethylene glycol (100 ml). A solution of potassium hydroxide (12.0 g, 0.214 moles) in water (20 ml) was added, and the reaction mixture was heated to 123° C. for 3.5 hours. After stirring at room temperature for 20 hours, the reaction mixture was cooled to 0° C. with an ice bath, and 10% hydrochloric acid was added slowly to adjust the pH to 2.0. The reaction mixture was extracted twice with 100 ml of ethyl acetate. The combined ethyl acetate extracts were washed with brine (100 ml), dried over sodium sulfate, filtered and concentrated to an oil. The title product was purified by silica gel chromatography and recrystallized from pentane, m.p. ca. 58° C. The structure assignment was supported by NMR, infrared spectroscopy and elemental analysis.

Analysis calculated for: $C_{14}H_{22}S$ (m.w.=222.4): Theory: C, 75.61; H, 9.71; S, 14.42. Found: C, 75.55; H, 10.07; S, 14.34.

EXAMPLE 3 trans-2-[[3,5-bis(1,1-dimethylethyl)phenyl]thio]cyclohexanol (3)

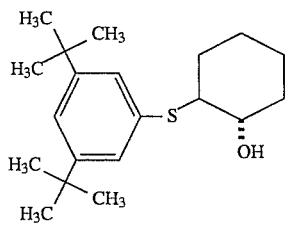

3,5-Bis(1,1-dimethylethyl)benzenethiol (Example 2) (5.0 g, 0.0225 moles) was added to freshly prepared sodium ethoxide (0.0230 moles) in absolute ethyl alcohol (50 ml). After stirring for 1 hour, cyclohexene oxide (2.2 g; 0.0225 moles) was added by syringe over 5 minutes, and the reaction mixture was stirred for 60 hours at room temperature. Water (100 ml) was added, and the reaction mixture was extracted twice with 75 ml of ethyl acetate. The combined ethyl acetate extracts were washed with brine (50 ml), dried over sodium sulfate, filtered and concentrated to give the title product as a yellow solid, which was recrystallized from cold pentane. The structure assignment was supported by NMR spectroscopy. The title compound was used in Example 4.

EXAMPLE 4

Methyl trans-[[2-[[3,5-bis(1,1-dimethylethyl)phenyl]thio]cyclohexyl]thio]acetate (4)

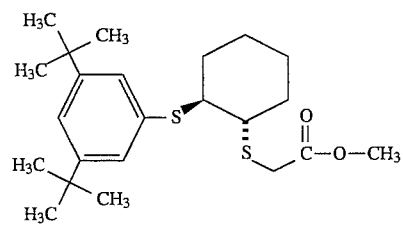

Methyl thioglycolate (2.65 g, 0.025 moles) was added by syringe to a solution of trans-2-[[3,5-bis(1,1-dimethylethyl)phenyl]thio]cyclohexanol (5.0 g., 0,025 moles) in methylene chloride (10 ml). After stirring the reaction mixture for 15 minutes, trifluoroacetic acid (10 ml) was added by syringe, and the reaction mixture was stirred for 20 hours at room temperature. The reaction mixture was poured into cold water (100 ml). After stirring for 30 minutes, the mixture was extracted with ethyl acetate. The aqueous layer was washed with ethyl acetate (50 ml). The combined ethyl acetate extracts were washed twice with 75 ml of water, dried over sodium sulfate, filtered and concentrated to give the crude product as an oil. The title compound was purified by silica gel chromatography and dried in a vacuum oven at 60° C. for 3 hours. The structure assignment was supported by NMR, infrared spectroscopy, and elemental analysis.

Analysis calculated for: $C_{23}H_{36}O_2S_2$ (m.w.=408.66): Theory: C, 67.60; H, 8.88; S, 15.69. Found: C, 67.62; H, 9.13; S, 15.58.

EXAMPLE 5 trans-[[2-[[3,5-bis(1,1-dimethylethyl)phenyl]thio]cyclohexyl]thio]acetic acid (5)

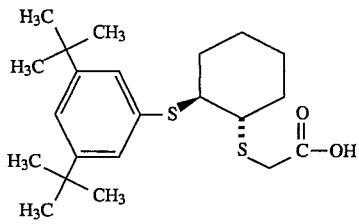

Water was added to a solution of the compound of Example 4 (9.2 g, 0.0255 moles) in methyl alcohol (100 ml) until the solution became cloudy. Lithium hydroxide hydrate (1.75 g, 0.0675 moles) was added, and the reaction mixture was stirred at room temperature. Periodically, water was added to make the solution cloudy. After 6 hours, the solution was made acidic with 10% hydrochloric acid and extracted with ethyl acetate. The ethyl acetate extract was dried over sodium sulfate, filtered, and concentrated to give the crude product as an oil. The product was purified by silica gel chromatography. The structure assignment was supported by NMR and elemental analysis.

Analysis calculated for: $C_{22}H_{34}S_2O_2$ (m.w.=394.63): Theory: C, 66.96; H, 8.68; S, 16.25. Found: C, 66.92; H, 8.80; S, 16.00.

EXAMPLE 6 trans-2-(phenylthio)cyclohexanol (6)

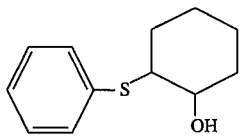

Thiophenol (2.14 g, 0.0194 mole) was added to freshly prepared sodium ethoxide (sodium, 0.45 g) in ethanol (30 ml). After several minutes, cyclohexene oxide was added, and the reaction mixture was stirred at room temperature for 24 hours. The reaction mixture was concentrated with a gentle flow of nitrogen gas. The residue was dissolved in diethyl ether (75 ml) and washed with in hydrochloric acid (19 ml). The diethyl ether was washed three times with 50 ml of 5% sodium carbonate, once with 0.5N hydrochloric acid (50 ml) and once with brine (25 ml), dried over anhydrous magnesium sulphate, filtered and concentrated with a rotary evaporator to give the product as an oil. The structure was supported by NMR and infrared spectroscopy.

EXAMPLE 7 trans-[[2-(phenylthio)cyclohexyl]thio]acetic acid (7)

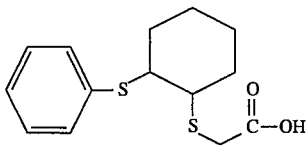

Mercaptoacetic acid (0.44 g, 0.0048 mole) was added to a cold solution of the compound of Example 6 (1.0 g, 0.0048 mole) in methylene chloride (5 ml) containing trifluoracetic acid (3.5 ml). The reaction mixture was stirred at room temperature for 20 hours. The reaction mixture was concentrated to an oil with a rotary evaporator. The residue was dissolved in diethyl ether (50 ml), washed three times with 20 ml of 5% sodium bicarbonate, followed by in hydrochloric acid (10 ml) and water (20 ml), dried over anhydrous magnesium sulfate, filtered and concentrated to a colorless oil with a rotary evaporator. The product was purified by silica gel chromatography. The structure was supported by NMR, infrared spectroscopy and elemental analysis.

Analysis calculated for: $C_{14}H_{18}S_2O_7$ (m.w.=282.44): Theory: C, 59.54; H, 6.42; S, 22.70. Found: C, 59.36; H, 6.57; S, 22.43.

EXAMPLE 8

O-[3-(1,1-dimethylethyl)phenyl]dimethylcarbamothioate (8)

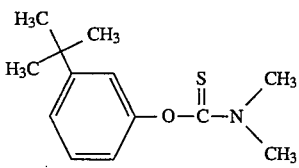

meta-t-Butyl phenol (30.0 g, 0.20 mole) was added to water (140 ml) containing potassium hydroxide (11.2 g, 0.20 mole) and stored at 0° C. for 20 hours. Dimethyl thiocarbamoyl chloride (32.8 g, 0.265 mole) was added as a solution in tetrahydrofuran (60 ml) to the cold solution with stirring. The ice bath was removed, and the turbid solution was stirred for 15 minutes. To this mixture was added 10% potassium hydroxide (75 ml). The reaction mixture was extracted three times with 125 ml of benzene. The combined benzene extracts were washed with brine (75 ml) and concentrated in a rotary evaporator to give the crude product as an oil. The product was purified by silica gel chromatography. The structure was supported by NMR.

EXAMPLE 9

3-(1,1dimethylethyl)benzenethiol (9)

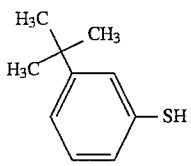

Starting with 0-[3-(1,1-dimethylethyl)phenyl]dimethyl-carbamothioate and following the procedure described in Example 2, the title compound was obtained.

EXAMPLE 10 trans-2-[[3-(1,1-dimethylethyl)phenyl]thio]cyclohexanol (10)

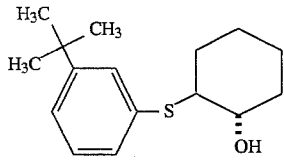

Using the method of Example 6, and substituting 3-(1,1-dimethylethyl)benzenethiol for thiophenol, the title compound was obtained.

EXAMPLE 11 trans-[[2-[[3-(1,1-dimethylethyl)phenyl]thio]cyclohexyl]thio]acetic acid (11)

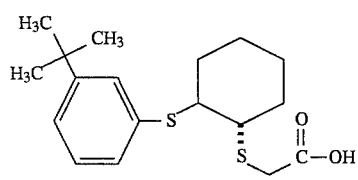

Trifluoroacetic acid (10 ml) was added to a solution of the title compound of Example 10 (3.6 g, 0.0136 mole) in methylene chloride (5 ml) with stirring. After several minutes, methyl thioglycolate (1.59 g, 0.015 mole) was added, and the reaction mixture was stirred for 30 minutes. The reaction mixture was poured into methanol (50 ml) containing lithium hydroxide hydrate (12.6 g, 0.30 mole). Water (125 ml) was slowly added to the mixture, and then the mixture was extracted with diethyl ether (100 ml). The aqueous phase was acidified with concentrated hydrochloric acid and extracted twice with 100 ml of diethyl ether. The combined diethyl ether extracts were washed with water (30 ml), 5% sodium bicarbonate (50 ml) and brine (50 ml), dried over anhydrous magnesium sulfate, filtered and concentrated with a rotary evaporator to give the crude product as an oil. The product was purified by silica gel chromatography. The structure was supported by NMR, infrared spectroscopy, and elemental analysis.

Analysis calculated for: $C_{18}H_{26}S_2O_2$ (m.w.=338.52): Theory: C, 63.87; H, 7.74; S, 18.94. Found: C, 64.00; H, 8.02; S, 19.10.

EXAMPLE 12

[1,1'-biphenyl]-3-yl dimethylcarbamoate (12)

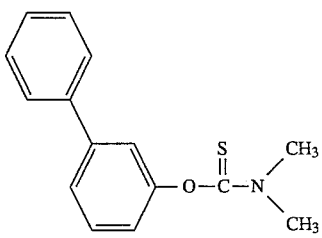

Using the method of Example 8, and substituting meta-phenyl phenol for meta-t-butyl phenol, the title compound was prepared. The structure was supported by NMR.

EXAMPLE 13

3-[1,1'-biphenyl]thiol (13)

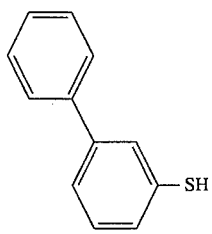

Starting with [1,1'-biphenyl]-3-yl dimethylcarbamoate, and using the procedure described in Example 2, the title compound was obtained.

EXAMPLE 14 trans-2-[([1,1'-biphenyl]-3-yl)thio]cyclohexanol (14)

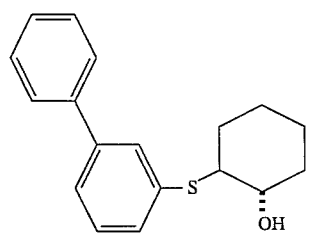

Starting with 3-[1,1'-biphenyl]thiol, and following the procedure described in Example 3, gave the title compound.

EXAMPLE 15 trans-[[2-[([1,1'-biphenyl]-3-yl)thio]cyclohexyl]thio]acetic acid (15)

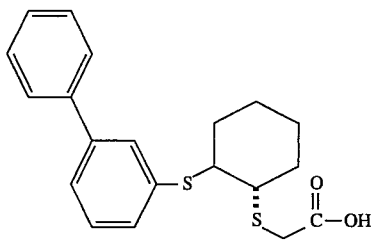

Starting with trans-2-[([1,1'-biphenyl]-3-yl)thio]cyclohexanol, and using the method described in Example 11, gave the title compound. The structure was supported by NMR, infrared spectroscopy and elemental analysis.

Analysis calculated for: $C_{20}H_{22}S_2O_2$ (m.w.=358.51): Theory: C, 67.00; H, 6.18; S, 17.89. Found: C, 66.94; H, 6.30; S, 18.07.

EXAMPLE 16 trans-2-[[2-[[3,5-bis(1,1-dimethylethyl)phenyl]thio]cyclohexyl]thio]-N-methyl-N-(2-pyridinylethyl)acetamide (16)

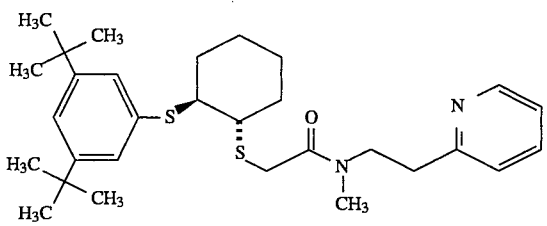

Oxalyl chloride (0.19 g, 0.0015 moles) was added by syringe to a cold (10° C.) solution of trans-[[2-[[3,5-bis(1,1-dimethylethyl)phenyl]thio]cyclohexyl]thio]acetic acid (Example 5) (0.55 g, 0.0014 moles) in benzene (50 ml). The cold bath was removed, and the reaction mixture was stirred at room temperature for 20 hours. The reaction mixture was concentrated to an oil using a rotary evaporator. The oil was dissolved in toluene (50 ml) and concentrated to an oil. The process was repeated using tetrahydrofuran (25 ml) instead of toluene. The residue was dissolved in tetrahydrofuran (50 ml). To this solution was added 2-(2-methylaminoethyl)pyridine (0.19 g, 0.0014 moles) and triethylamine (0.22 g), and the reaction mixture was stirred at room temperature for 48 hours. The white solid precipitate was removed by filtration and washed with ethyl acetate (25 ml). The filtrate was concentrated to give the crude product as an oil. The product was purified by silica gel chromatography and dried in vacuo at 100° C. for 1 hour to give the title compound. The structure assignment was supported by NMR, infrared spectroscopy and elemental analysis.

Analysis calculated for: $C_{30}H_{44}N_2O_2S_2$ (m.w.=512.83): Theory: C, 70.26; H, 8.65; S, 5.46. Found: C, 69.95; H, 8.76; S, 5.43.

EXAMPLE 17 trans-[[2-[[3,5-bis(1,1-dimethylethyl)phenyl]thio]cyclohexyl]oxy]acetic acid (17)

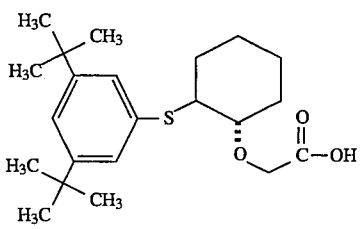

Sodium hydride (0.33 g, 0.0138 mole) was added to a solution of trans-2-[[3,5-bis(1,1-dimethylethyl)phenyl]thio]cyclohexanol (3.4 g, 0.0106 mole) in tetrahydrofuran (50 ml) at 0° C. After stirring the reaction mixture for 1.5 hours, the tetrahydrofuran was removed by rotary evaporation. Dimethyl sulfoxide (75 ml) was added followed by chloroacetic acid sodium salt (1.48 g, 0.0127 mole), and the reaction mixture was stirred at room temperature for 10 days. Water (100 ml) was added dropwise to the mixture followed by 10% hydrochloric acid (10 ml). The product was extracted twice with 200 ml of ethyl acetate. The combined ethyl acetate extracts were washed twice with 200 ml of water, dried over anhydrous sodium sulfate, filtered, and concentrated. The product was purified by chromatography on silica gel. The structure was supported by NMR and elemental analysis (378.6+¼ mole $H_2O$).

Analysis calculated for: $C_{22}H_{34}O_3S$+¼ mole $H_2O$: Theory: C, 68.98; H, 9.08; S, 8.37. Found: C, 69.12; H, 9.21; S, 8.27.

EXAMPLE 18

3,6-dioxabicyclo[3.1.0]hexane (18)

2,5-Dihydrofuran (DHF) (13.2 g, 0.188 mole) was added by syringe to a solution containing 3-chloroperoxybenzoic acid (29.1 g, 0.198, mole) and trifluoroacetic acid (0.5 ml) in methylene chloride (500 ml). After stirring at room temperature for 20 hours, the white solid was removed by filtration. The filtrate was washed with a solution of sodium carbonate (100 ml, saturated). The organic phase was stirred with solid sodium carbonate and sodium thiosulfate for 20 minutes and filtered. The product was purified by low pressure distillation (41° C./5 mmHg). The structure was supported by NMR.

EXAMPLE 19 trans-4-[[3,5-bis(1,1-dimethylethyl)phenyl]thio]tetrahydro-3-furanol (19)

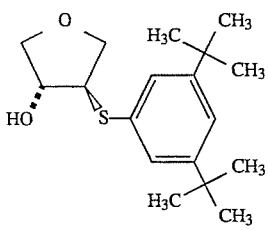

3,5-Bis(1,1-dimethylethyl)benzenethiol (0.0078 mole) and the title compound of Example 18 (0.0074 mole) are added to a degassed (Argon) solution of 50% sodium hydroxide (5 ml) and isopropyl alcohol (50 ml). The reaction is heated to reflux for 24 hours. The reaction is cooled to room temperature and poured into water (125 ml). The solution is made acidic with 1N hydrochloric acid and extracted 3 times with 100 ml of diethyl ether. The combined diethyl ether extracts are dried over anhydrous magnesium sulfate, filtered and concentrated with a rotary evaporator. The product is purified by silica gel chromatography.

EXAMPLE 20 trans-4-[[3,5-bis(1,1-dimethylethyl)phenyl]phenyl]thio]tetrahydro-3-furanol, acetate (20)

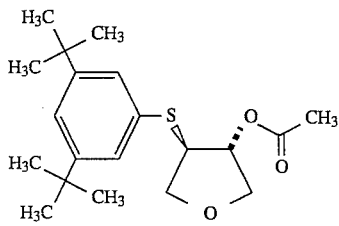

The title compound of Example 19 (0.0062 mole) is added to acetic anhydride (20 ml). Triethylamine (0.0062 mole) is added, and the reaction mixture is stirred for 3 hours. Additional triethylamine (0.3 ml) is added, and the reaction mixture is stirred for 2 hours. The reaction mixture is concentrated to an oil with a gentle flow of nitrogen gas. The residue is dissolved in diethyl ether (75 ml), washed twice with 50 ml of 0.25N hydrochloric acid and once with 25 ml of brine, dried over anhydrous magnesium sulfate, filtered and concentrated with a gentle flow of nitrogen gas. The product is purified by silica gel chromatography.

EXAMPLE 21 butanedionic acid, trans-mono[4-[[3,5-bis(1,1-dimethylethyl)4-hydroxyphenyl]thio]tetrahydro-3-furanyl]ester (21)

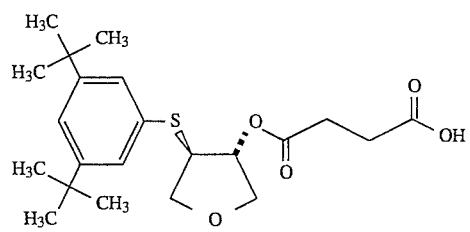

Succinic anhydride (0.0185 mole) and triethylamine (0.0185 mole) are added to a solution of tetrahydrofuran (THF) (50 ml) containing the compound of Example 19 (0.0092 mole). The reaction mixture is stirred for 3 days and then concentrated to an oil with a gentle flow of nitrogen gas. The residue is dissolved in diethyl ether. The solution is washed twice with 50 ml of water and once with 20 ml of 1N hydrochloric acid, dried over anhydrous magnesium sulfate, filtered and concentrated to an oil with a rotary evaporator. The product is purified by silica gel chromatography.

EXAMPLE 22 trans-2-[[2-[([1,1'-biphenyl]-3-yl)thio]cyclohexyl]thio]-N-(2,6,dimethylphenyl]acetamide (22)

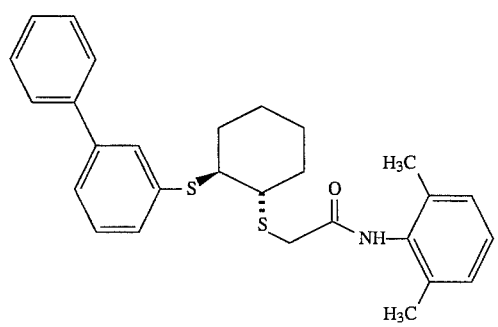

Oxalyl chloride (18 mg, 0.000142 mole) was added to a solution of trans-2-[([1,1'-biphenyl]-3-yl)thio]cyclohexanol(24 mg, 0.000071 mole) in toluene (25 ml) and stirred magnetically for 20 hours at room temperature. The solution was concentrated to an oil. The oil was dissolved in toluene (25 ml) and concentrated to an oil. The oil was dissolved in ethyl ether (50 ml) to which were added 2,6-dimethylaniline (8.6 mg, 0.000071 mole) and triethylamine (0.3 ml). The mixture was stirred at room temperature for three hours, filtered and concentrated to an oil. The product was purified by silica gel chromatography. The structure was supported by NMR.

Analysis calculated for $C_{28}H_{31}NOS_2$. 0.25M $H_2O$: Theory: C, 72.14; H, 6.81; N, 3.00. Found: C, 72.21; H, 7.00; N, 2.94.

EXAMPLE 23 trans-2-[[2-[[3,5-bis(1,1-dimethylethyl)phenyl]thio]cychexyl]thio]-N-[3-(dimethylamino)propyl]-N-methylacetamide (23)

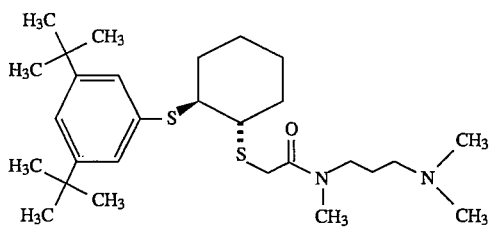

Oxalyl chloride (55 mg, 0.00043 mole) was added to a solution of trans-[[2-[[3,5-bis(1,1-dimethylethyl)phenyl]thio]cyclohexyl]thio]acetic acid (85 mg, 0.000215 mole) in toluene (50 ml) and was stirred at room temperature for 20 hours. The solution was concentrated to an oil. The oil was redissolved in toluene (50 ml) and concentrated to an oil. The oil was dissolved in ethyl ether (75 ml) to which were added N,N,N'-trimethyl-1,3-propane diamine (19.5 mg, 0.000215 mole) and triethylamine (0.5 ml). After stirring at room temperature for 3 hours the mixture was filtered and concentrated to an oil. The product was purified by silica gel chromatography. The structure was supported by NMR.

Analysis calculated for $C_{28}H_{48}N_2OS_2 \cdot 0.5M\ H_2O$: Theory: C, 67.02; H, 9.84; N, 5.58. Found: C, 67.08; H, 9.82; N, 5.57.

EXAMPLE 24 trans-2-[[2-[[3,5-bis(1,1-dimethylethyl)phenyl]thio]cyclohexyl]thio]-N-[4-(dimethylamino)butyl]acetamide (24)

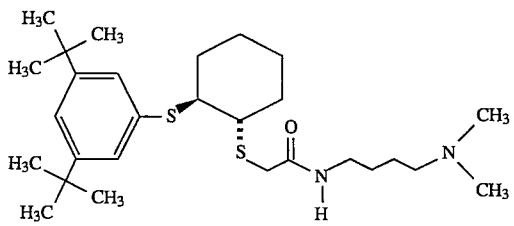

By following the method of Example 23 and substituting 4-dimethylaminobutylamine for N,N,N'-trimethyl-1,3-propanediamine, the title compound was prepared. The structure was supported by NMR.

Analysis calculated for $C_{28}H_{48}N_2OS_2$: Theory: C, 68.24; H, 9.82; N, 5.68. Found: C, 67.84; H, 9.91; N, 5.68.

EXAMPLE 25 trans-2-[[2-[[3,5-bis(1,1-dimethylethyl)phenyl]thio]cyclohexyl]thio]-N-(2-methoxyethyl)acetamide (25)

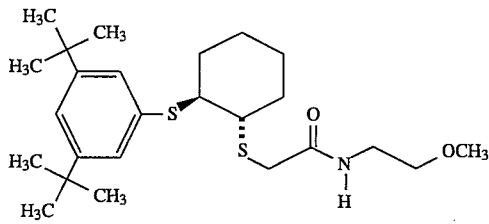

By following the method of Example 23 and substituting 2-methoxyethylamine for N,N,N'-trimethyl-1,3-propanediamine, the title compound was prepared. The structure was supported by NMR.

Analysis calculated for $C_{25}H_{41}NO_2S_2$: Theory: C, 66.47; H, 9.15; N, 3.10: Found: C, 66.12; H, 9.28; N, 3.04.

EXAMPLE 26

2-[[4-(1,1-dimethylethyl)phenyl]thio]cyclohexanone (26)

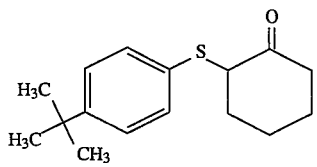

To a solution of 2-chlorocyclohexanone (6.1 g, 0.046 moles) in tetrahydrofuran (250 ml) cooled to +5° C. by an ice bath was added 4-t-butyl-thiophenol (6.6 g, 0.040 moles). After stirring for 15 minutes, triethylamine (13 ml) was added. The ice bath was removed and the mixture was stirred at room temperature for 60 hours. The mixture was filtered to remove a white solid. The filtrate was concentrated to an oil, and the product was purified by silica gel chromatography to give a white solid which was recrystallized from hexane (DSC 64.25° C.). The structure was supported by NMR and Ir.

Analysis calculated for $C_{16}H_{22}OS$ (262.42): Theory: C, 73.23; H, 8.45; S, 12.22. Found: C, 73.12; H, 8.76; S, 12.19.

EXAMPLE 27

2-[[3,5-bis(1,1-dimethylethyl)phenyl]thio]cyclohexanone (27)

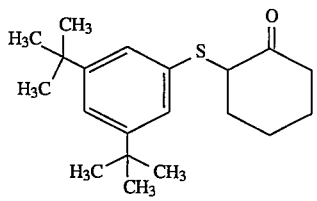

2-Chlorocyclohexanone (0.6 g, 0.0045 moles) was added to a cold (+5° C.) solution of 3,5-bis (1,1-dimethylethyl-)benzenethiol (Example 2)(1.0 g, 0.0045 moles) in tetrahydrofuran (50 ml). The solution was stirred for 15 minutes. Triethylamine (1.25 ml) was added, the cold bath was removed and the mixture was stirred at room temperature for 20 hours and then at 50° C. for 2 hours. The mixture was cooled to room temperature and filtered to remove a white solid. The filtrate was concentrated to an oil. The product was purified by silica gel chromatography to give a white solid which was recrystallized from hexane (DSC 81.49° C.). The structure was supported by NMR and Ir.

Analysis calculated for $C_{20}H_{30}OS$: Theory: C, 75.42; H, 9.49; S, 10.07. Found: C, 75.45; H, 9.72; S, 10.36.

EXAMPLE 28

2-[[4-(1,1-dimethylethyl)phenyl]thio]cyclopentanone (28)

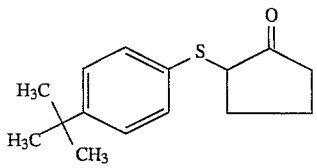

By following the method of Example 26 and substituting 2-chlorocyclopentanone for 2-chlorocyclohexanone, the title compound was obtained. The structure was supported by NMR and Ir.

EXAMPLE 29

2-(phenylthio)cyclohexanone (29)

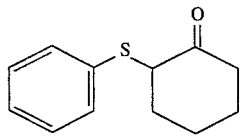

By following the method of Example 26 and substituting thiophenol for 4-t-butylthiophenol the title compound was obtained. The structure was supported by NMR and Ir.

EXAMPLE 30

Starting with 2-bromothiophenol and following the procedure of Example 3 gives trans-2-[(2-bromophenyl)thio] cyclohexanol.

Starting with this compound and following the procedures described in Examples 4, 5, 16, 22, 23, and 25 respectively gives:

(a) methyl trans-[[2-[(2-bromophenyl)thio]cyclohexyl]thio] acetate;
(b) trans-[[2-[(2-bromophenyl)thio]cyclohexyl]thio]acetic acid;
(c) trans-[[2-[(2-bromophenyl)thio]cyclohexyl]thio]-N-methyl-N-(2-pyridinylethyl)acetamide;
(d) trans-2-[[2-[(2-bromophenyl)thio]cyclohexyl]thio]-N-(2,6-dimethylphenyl)acetamide;
(e) trans-2-[[2-[[2-bromophenyl]thio]cyclohexyl]thio]-N-[3-(dimethylamino)propyl]-N-methylacetamide; and
(f) trans-2-[[2-[[2-bromophenyl]thio]cyclohexyl]thio]-N-(2-methoxyethyl)acetamide.

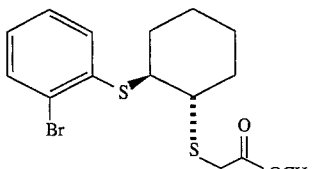

(a)

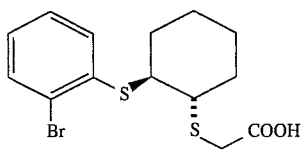

(b)

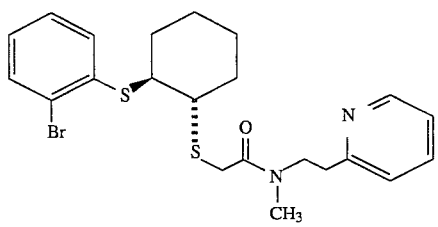

(c)

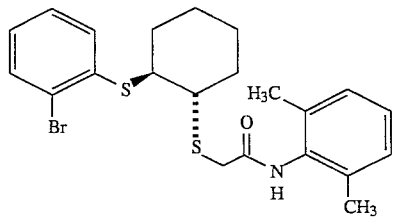

(d)

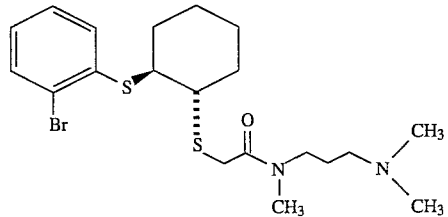

(e)

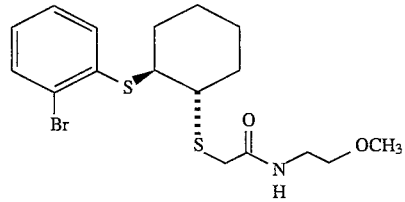

(f)

EXAMPLE 31

Starting with 3-bromothiophenol and following the procedure of Example 3 gives trans-2-[(3-bromophenyl)thio] cyclohexanol.

Starting with this compound and following the procedures described in Examples 4, 5, 16, 22, 23, and 25 respectively gives:

(a) methyl trans-[[2-[(3-bromophenyl)thio]cyclohexyl]thio] acetate;
(b) trans-[[2-[(3-bromophenyl)thio]cyclohexyl]thio]acetic acid;
(c) trans-[[2-[(3-bromophenyl)thio]cyclohexyl]thio]-N-methyl-N-(2-pyridinylethyl)acetamide;
(d) trans-2-[[2-[(3-bromophenyl)thio]cyclohexyl]thio]-N-(2,6-dimethylphenyl)acetamide;
(e) trans-2-[[2-[[3-bromophenyl]thio]cyclohexyl]thio]-N-[3-(dimethylamino)propyl]-N-methylacetamide; and
(f) trans-2-[[2-[[3-bromophenyl]thio]cyclohexyl]thio]-N-(2-methoxyethyl)acetamide.

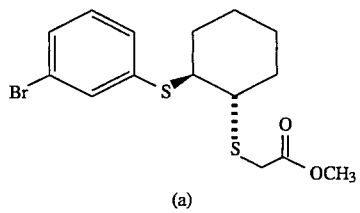
(a)

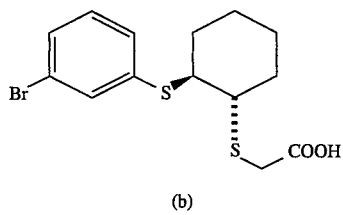
(b)

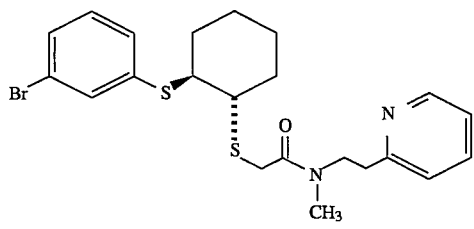
(c)

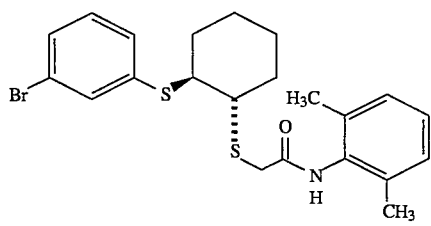
(d)

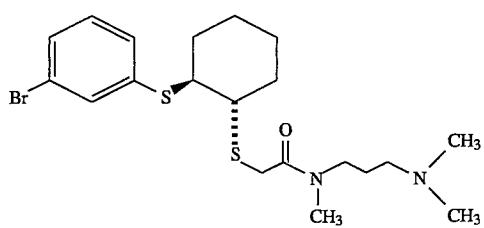
(e)

-continued

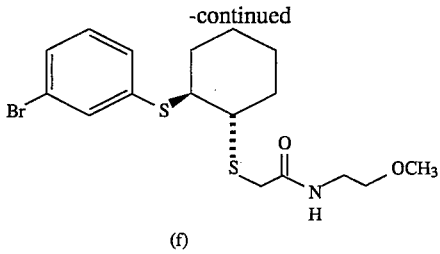
(f)

EXAMPLE 32

Starting with 4-bromothiophenol and following the procedure of Example 3 gives trans-2-[(4-bromophenyl)thio]cyclohexanol.

Starting with this compound and following the procedures described in Examples 4, 5, 16, 22, 23, and 25 respectively gives:

(a) methyl trans-[[2-[(4-bromophenyl)thio]cyclohexyl]thio] acetate;
(b) trans-[[2-[(4-bromophenyl)thio]cyclohexyl]thio]acetic acid;
(c) trans-2-[[2-[(4-bromophenyl)thio]cyclohexyl]thio]-N-methyl-N-( 2-pyridinylethyl)acetamide;
(d) trans-2-[[2-[(4-bromophenyl)thio]cyclohexyl]thio]-N-(2,6-dimethylphenyl)acetamide;
(e) trans-2-[[2-[[4-bromophenyl]thio]cyclohexyl]thio]-N-[3-(dimethylamino)propyl]-N-methylacetamide; and
(f)rans-2-[[2-[[4-bromophenyl]thio]cyclohexyl]thio]-N-(2-methoxyethyl)acetamide.

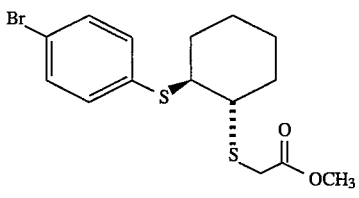
(a)

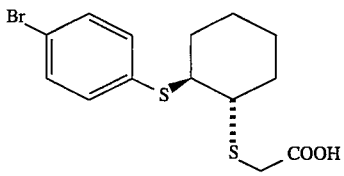
(b)

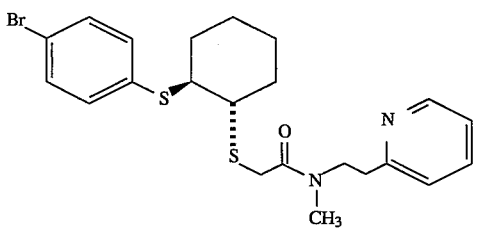
(c)

-continued

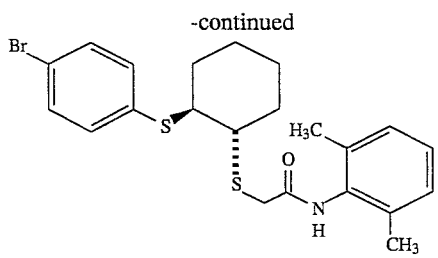
(d)

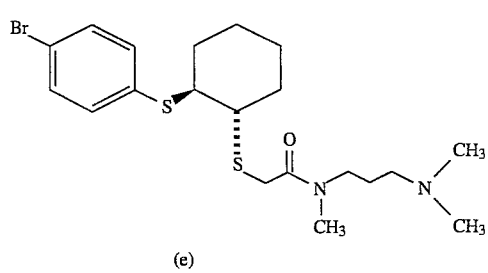
(e)

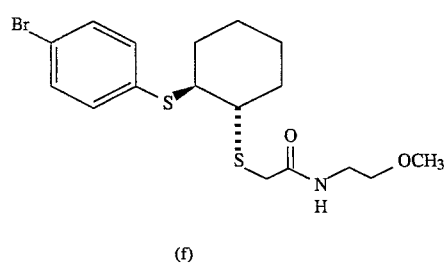
(f)

EXAMPLE 33

Starting with 2,5-dichlorobenzenethiol and following the procedure of Example 3 gives trans-2-[(2,5-dichlorophenyl)-thio]cyclohexanol.

Starting with this compound and following the procedures described in Examples 4, 5, 16, 22, 23, and 25 respectively gives:
(a) methyl trans-[[2-[(2,5-dichlorophenyl)thio]cyclohexyl] thio]acetate;
(b) trans-[[2-[(2,5-dicholorophenyl)thio]cyclohexyl]thio] acetic acid;
(c) trans-2-[[2-[(2,5-dichlorophenyl)thio]cyclohexyl]thio]-N-methyl-N-(2-pyridinylethyl)acetamide;
(d) trans-2-[[2-[(2,5-dichlorophenyl)thio]cyclohexyl] thio]-N-(2,6-dimethylphenyl)acetamide;
(e) trans-2-[[2-[[2,5-dichlorophenyl]thio]cyclohexyl]thio]-N-[3-(dimethylamino)propyl]-N-methylacetamide; and
(f) trans-2-[[2-[[2,5-dichlorophenyl]thio]cyclohexyl]thio]-N-(2-methoxyethyl)acetamide.

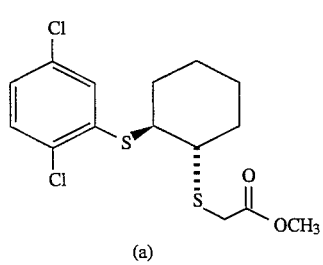
(a)

-continued

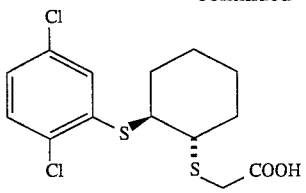
(b)

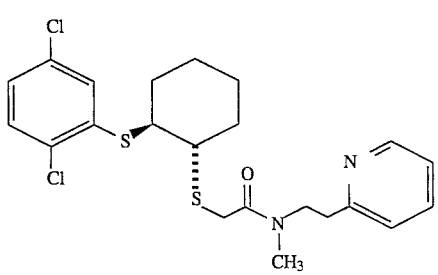
(c)

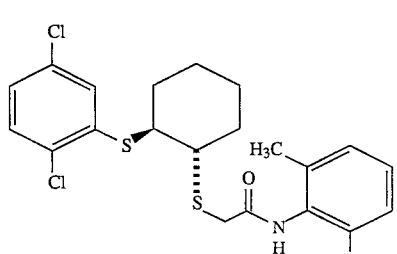
(d)

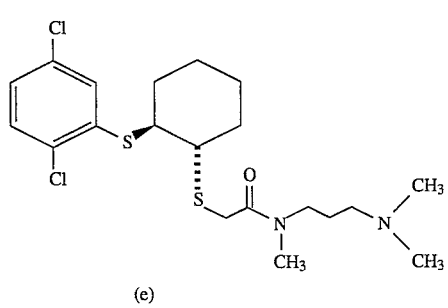
(e)

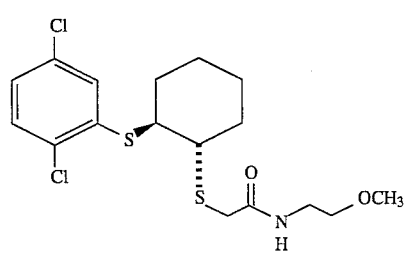
(f)

EXAMPLE 34

Starting with 2-chlorothiophenol and following the procedure of Example 3 gives trans-2-[(2-chlorophenyl)thio] cyclohexanol.

Starting with this compound and following the procedures described in Examples 4, 5, 16, 22, 23, and respectively gives:

(a) methyl trans-[[2-[(2-chlorophenyl)thio]cyclohexyl]thio]acetate;
(b) trans-[[2-[(2-chlorophenyl)thio]cyclohexyl]thio]acetic acid;
(c) trans-[[2-[(2-chlorophenyl)thio]cyclohexyl]thio]-N-(2-pyridinylethyl)acetamide;
(d) trans-2-[[2-[(2-chlorophenyl)thio]cyclohexyl]thio]-N-(2,6-dimethylphenyl)acetamide;
(e) trans-2-[[2-[(2-chlorophenyl]thio]cyclohexyl]thio]-N-[3-(dimethylamino)propyl]-N-methylacetamide; and
(f) trans-2-[[2-[(2-chlorophenyl]thio]cyclohexyl]thio]-N-(2-methoxyethyl)acetamide.

(b) trans-[[2-[(3-chlorophenyl)thio]cyclohexyl]thio]acetic acid;
(c) trans-[[2-[(3-chlorophenyl)thio]cyclohexyl]thio]N-methyl-N-(2-pyridinylethyl)acetamide;
(d) trans-2-[[2-[(3-chlorophenyl)thio]cyclohexyl]thio]-N-(2,6-dimethylphenyl)acetamide;
(e) trans-2-[[2-[(3-chlorophenyl]thio]cyclohexyl]thio]-N-[3-(dimethylamino)propyl]-N-methylacetamide; and
(f) trans-2-[[2-[(3-chlorophenyl]thio]cyclohexyl]thio]-N-(2-methoxyethyl)acetamide.

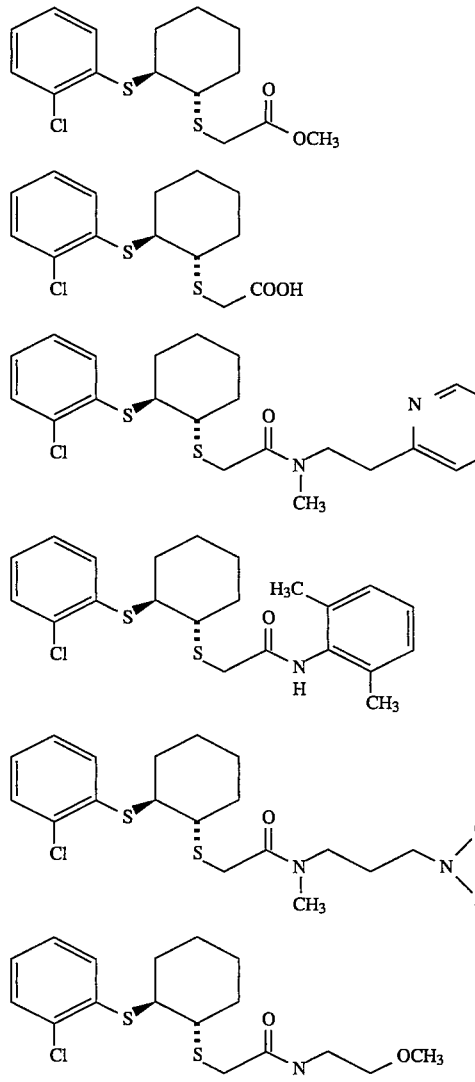

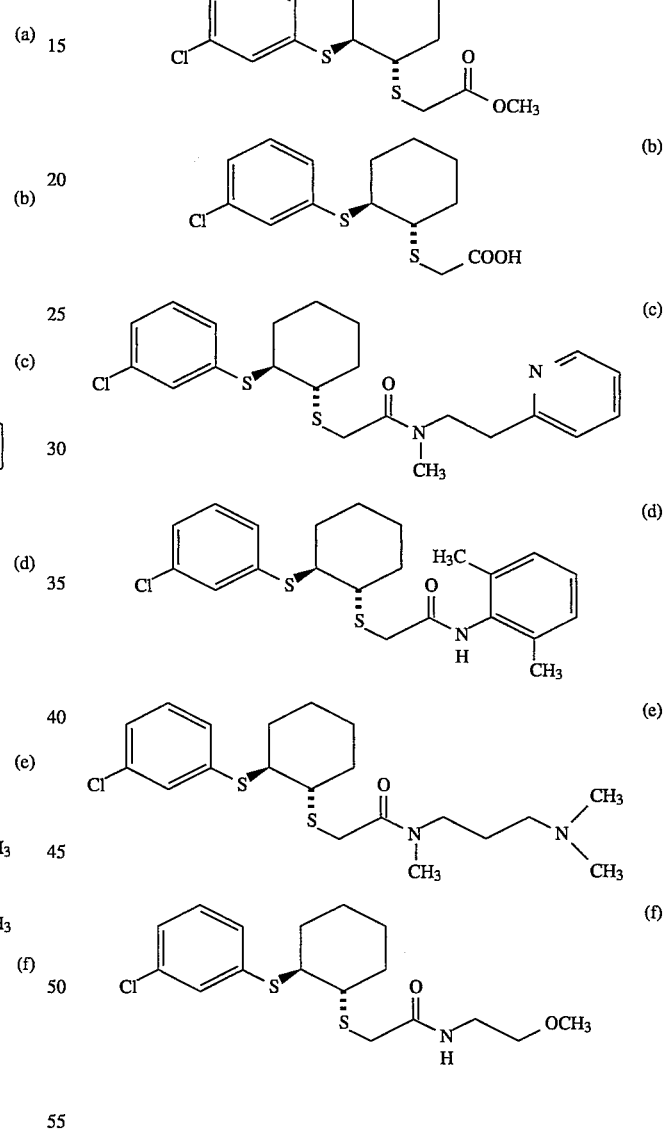

EXAMPLE 35

Starting with 3-chlorothiophenol and following the procedure of Example 3 gives trans-2-[(3-chlorophenyl)thio]cyclohexanol.

Starting with this compound and following the procedures described in Examples 4, 5, 16, 22, 23, and respectively gives:

(a) methyl trans-[[2-[(3-chlorophenyl)thio]cyclohexyl]thio]acetate;

EXAMPLE 36

Starting with 4-chlorothiophenol and following the procedure of Example 3 gives trans-2-[(4-chlorophenyl)thio]cyclohexanol.

Starting with this compound and following the procedures described in Examples 4, 5, 16, 22, 23, and 25 respectively gives:

(a) methyl trans-[[2-[(4-chlorophenyl)thio]cyclohexyl]thio]acetate;
(b) trans-[[2-[(4-chlorophenyl)thio]cyclohexyl]thio]acetic acid;

(c) trans-2-[[2-[(4-chlorophenyl)thio]cyclohexyl]thio]-N-methyl-N-(2-pyridinylethyl)acetamide;
(d) trans-2-[[2 -[(4-chlorophenyl)thio]cyclohexyl]thio]-N-(2,6-dimethylphenyl)acetamide;
(e) trans-2-[[2-[[4-chlorophenyl]thio]cyclohexyl] thio]-N-[3-(dimethylamino)propyl]-N-methylacetamide; and
(f) trans-2-[[2-[[4-chlorophenyl]thio]cyclohexyl thio]-N-(2-methoxyethyl)acetamide.

(d) trans-2-[[2-[(2,6-dichlorophenyl)thio]cyclohexyl]thio]-N-(2,6-dimethylphenyl)acetamide;
(e) trans-2-[[2-[[2,6-dichlorophenyl]thio]cyclohexyl]thio]-N-[3-(dimethylamino)propyl]-N-methylacetamide; and
(f) trans-2-[[2-[[2,6-dichlorophenyl]thio]cyclohexyl]thio]-N-(2-methoxyethyl)acetamide.

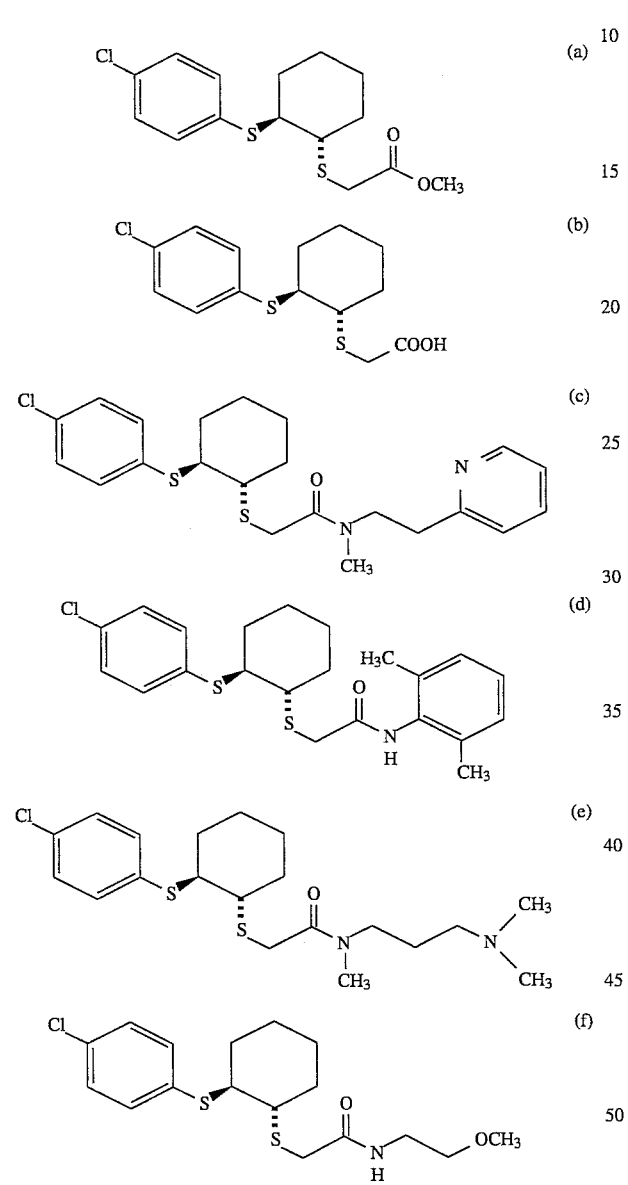

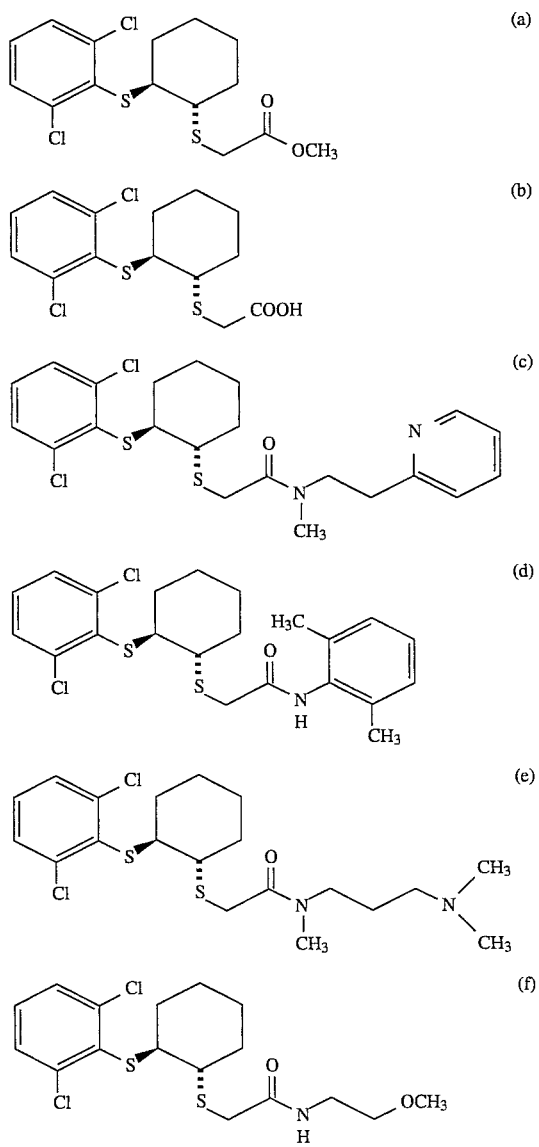

EXAMPLE 37

Starting with 2,6-dichlorobenzenethiol and following the procedure of Example 3 gives trans-2-[(2,6-dichlorophenyl)thio]cyclohexanol.

Starting with this compound and following the procedures described in Examples 4, 5, 16, 22, 23, and 25 respectively gives:
(a) methyl trans-[[2-[(2,6-dichlorophenyl)thio]cyclohexyl]thio]acetate;
(b) trans-[[2-[(2,6-dichlorophenyl)thio]cyclohexyl]thio]acetic acid;
(c) trans-2-[[2-[(2,6-dichlorophenyl)thio]cyclohexyl]-thio]-N-methyl-N-(2-pyridinylethyl)acetamide;

EXAMPLE 38

Starting with 3,4-dichlorobenzenethiol and following the procedure of Example 3 gives trans-2-[(3,4-dichlorophenyl)-thio]cyclohexanol.

Starting with this compound and following the procedures described in Examples 4, 5, 16, 22, 23, and 25 respectively gives:
(a) methyl trans-[[2-[(3,4-dichlorophenyl)thio]cyclohexyl] thio]acetate;
(b) trans-[[2-[(3,4-dichlorophenyl)thio]cyclohexyl]thio]acetic acid;
(c) trans-2-[[2-[(3,4-dichlorophenyl)thio]cyclohexyl]-thio]-N-methyl-N-(2-pyridinylethyl) acetamide;
(d) trans-2-[[2-[(3,4-dichlorophenyl)thio]cyclohexyl]thio]-N-(2,6-dimethylphenyl)acetamide;

(e) trans-2-[[2-[[3,4-dichlorophenyl]thio]cyclohexyl]thio]-N-[3-(dimethylamino)propyl]-N-methylacetamide; and
(f) trans-2-[[2-[3,4-dichlorophenyl]thio]cyclohexyl]thio]-N-(2-methoxyethyl)acetamide.

(f) trans-2-[[2-[[2,4-dimethylphenyl]thio]cyclohexyl]thio]-N-(2-methoxyethyl)acetamide.

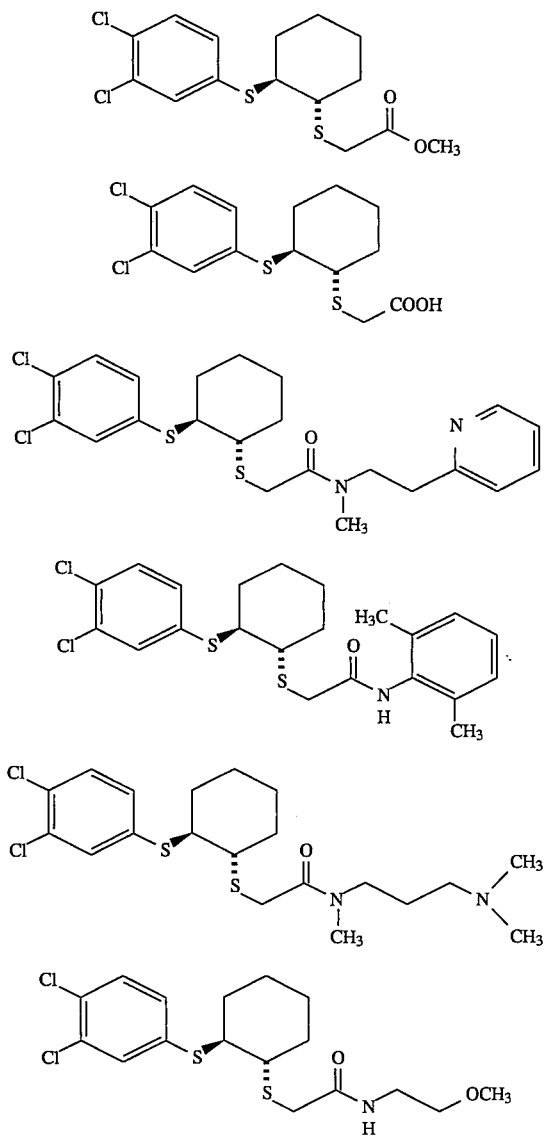

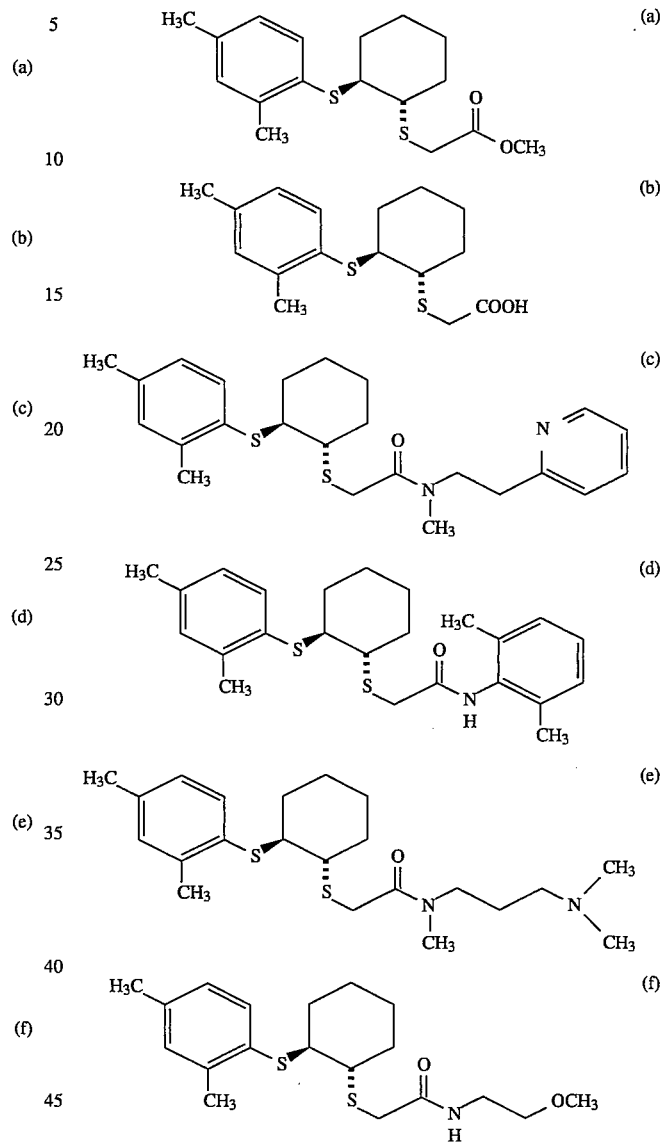

EXAMPLE 39

Starting with 2,4-dimethylthiophenol and following the procedure of Example 3 gives trans-2-[(2,4-dimethylphenyl)-thio]cyclohexanol.

Starting with this compound and following the procedures described in Examples 4, 5, 16, 22, 23, and 25 respectively gives:
(a) methyl trans-[[2-[(2,4-dimethylphenyl)thio]cyclohexyl]thio]acetate;
(b) trans-[[2-[(2,4-dimethylphenyl)thio]cyclohexyl]thio]acetic acid;
(c) trans-2-[[2-[(2,4-dimethylphenyl)thio]cyclohexyl]-thio]-N-methyl-(2-pyridinylethyl) acetamide;
(d) trans-2-[[2-[(2,4-dimethylphenyl)thio]cyclohexyl]thio]-N-(2,6-dimethylphenyl)acetamide;
(e) trans-2-[[2-[[2,4-dimethylphenyl]thio]cyclohexyl]thio]-N-[3-(dimethylamino)propyl]-N-methylacetamide; and

EXAMPLE 40

Starting with 2,5-dimethylthiophenol and following the procedure of Example 3 gives trans-2-[(2,5-dimethylphenyl)-thio]cyclohexanol.

Starting with this compound and following the procedures described in Examples 4, 5, 16, 22, 23, and 25 respectively gives:
(a) methyl trans-[[2-[(2,5-dimethylphenyl)thio]cyclohexyl]thio]acetate;
(b) trans-[[2-[(2,5-dimethylphenyl)thio]cyclohexyl]thio]acetic acid;
(c) trans-2-[[2-[(2,5-dimethylphenyl)thio]cyclohexyl]thio]-N-methyl-N-(2-pyridinylethyl)acetamide;
(d) trans-2-[[2-[(2,5-dimethylphenyl)thio]cyclohexyl]thio]-N-(2,6-dimethylphenyl)acetamide;
(e) trans-2-[[2-[[2,5-dimethylphenyl]thio]cyclohexyl]thio]-N-[3-(dimethylamino)propyl]-N-methylacetamide; and (f) trans-2-[[2-[[2,5-dimethylphenyl]thio]cyclohexyl]thio]-N-(2-methoxyethyl)acetamide.

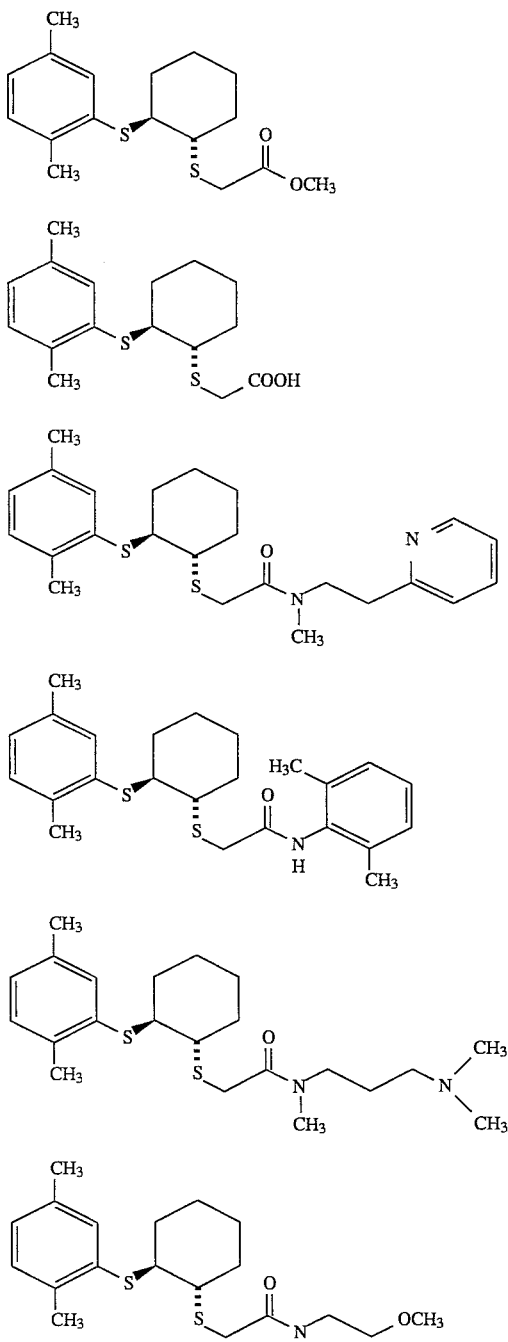

EXAMPLE 41

Starting with 3,4-dimethylthiophenol and following the procedure of Example 3 gives trans-2-[(3,4-dimethylphenyl)-thio]cyclohexanol.

Starting with this compound and following the procedures described in Examples 4, 5, 16, 22, 23, and 25 respectively gives:
(a) methyl trans-[[2-[(3,4-dimethylphenyl)thio]cyclohexyl]thio]acetate;
(b) trans-[[2-[(3,4-dimethylphenyl)thio]cyclohexyl]thio]acetic acid;
(c) trans-2-[[2-[(3,4-dimethylphenyl)thio]cyclohexyl]thio]-N-methyl-N-(2-pyridinylethyl)acetamide;
(d) trans-2-[[2-[(3,4-dimethylphenyl)thio]cyclohexyl]thio]-N-(2,6-dimethylphenyl)acetamide;
(e) trans-2-[[2-[(3,4-dimethylphenyl)thio]cyclohexyl]thio]-N-[3-(dimethylamino)propyl]-N-methylacetamide; and
(f) trans-2-[[2-[(3,4-dimethylphenyl)thio]cyclohexyl]thio]-N-(2-methoxyethyl)acetamide.

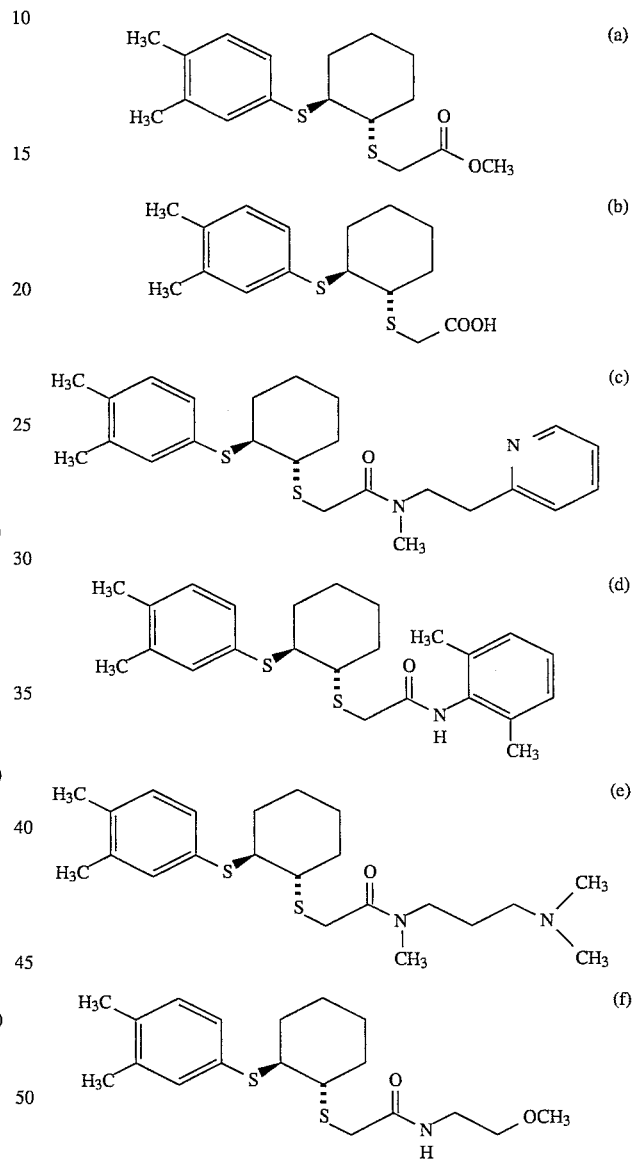

EXAMPLE 42

Starting with 4-fluorothiophenol and following the procedure of Example 3 gives trans-2-[(4-fluorophenyl)thio]cyclohexanol.

Starting with this compound and following the procedures described in Examples 4, 5, 16, 22, 23, and 25 respectively gives:
(a) methyl trans-[[2-[(4-fluorophenyl)thio]cyclohexyl]thio]acetate;
(b) trans-[[2-[(4-fluorophenyl)thio]cyclohexyl]thio]acetic acid;
(c) trans-[[2-[(4-fluorophenyl)thio]cyclohexyl]thio]-N-methyl-N-(2-pyridinylethyl) acetamide;

(d) trans-2-[[2-[(4-fluorophenyl)thio]cyclohexyl]thio]-N-(2,6-dimethylphenyl)acetamide;
(e) trans-2-[[2-[(4-fluorophenyl)thio]cyclohexyl]thio]-N-[3-(dimethylamino)propyl]-N-methylacetamide; and
(f) trans-2-[[2-[(4-fluorophenyl)thio]cyclohexyl]thio]-N-(2-methoxyethyl)acetamide.

(e) trans-2-[[2-[[4-hydroxyphenyl]thio]cyclohexyl]thio]-N-[3-(dimethylamino)propyl]-N-methylacetamide; and
(f) trans-2-[[2-[[4-hydroxyphenyl]thio]cyclohexyl]thio]-N-(2-methoxyethyl)acetamide.

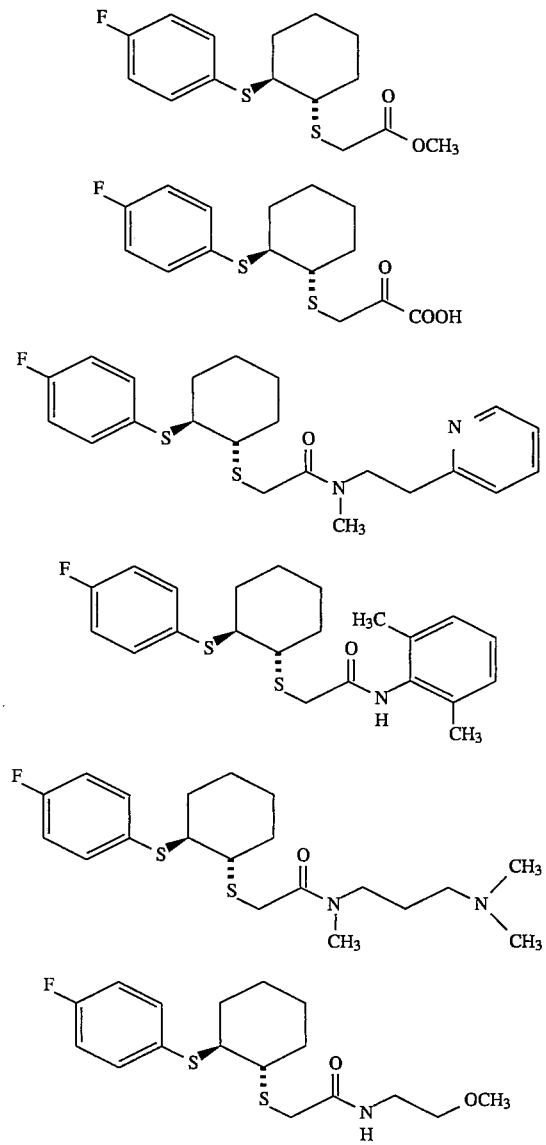

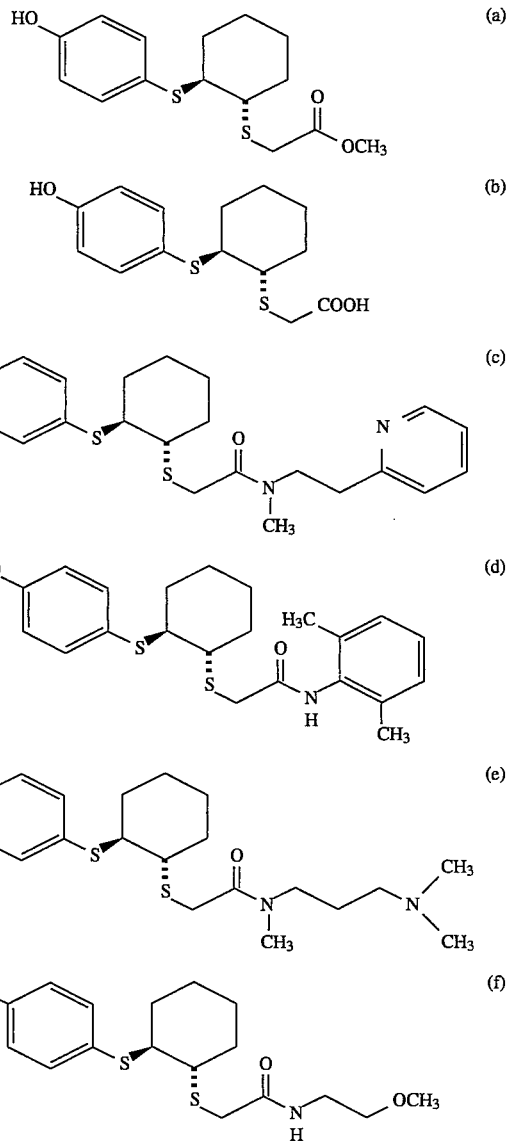

EXAMPLE 43

Starting with 4-hydroxythiophenol and following the procedure of Example 3 gives trans-2-[(4-hydroxyphenyl)thio]cyclohexanol.

Starting with this compound and following the procedures described in Examples 4, 5, 16, 22, 23, and 25 respectively gives:
(a) methyl trans-[[2-[(4-hydroxyphenyl)thio]cyclohexyl]thio]acetate;
(b) trans-[[2-[(4-hydroxyphenyl)thio]cyclohexyl]thio]acetic acid;
(c) trans-[[2-[(4-hydroxyphenyl)thio]cyclohexyl]thio]-N-methyl-N-(2-pyridinylethyl)acetamide;
(d) trans-2-[[2-[(4-hydroxyphenyl)thio]cyclohexyl]thio]-N-(2,6-dimethylphenyl)acetamide;

EXAMPLE 44

Starting with 2-isopropylthiophenol and following the procedure of Example 3 gives trans-2-[(2-isopropylphenyl)thio]cyclohexanol.

Starting with this compound and following the procedures described in Examples 4, 5, 16, 22, 23, and 25 respectively gives:
(a) methyl trans-[[2-[(2-isopropylphenyl)thio]cyclohexyl]thio]acetate;
(b) trans-[[2-[(2-isopropylphenyl)thio]cyclohexyl]thio]acetic acid;
(c) trans-2-[[2-[(2-isopropylphenyl)thio]cyclohexyl]thio]-N-methyl-N-(2-pyridinylethyl)acetamide;
(d) trans-2-[[2-[(2-isopropylphenyl)thio]cyclohexyl]thio]-N-(2,6-dimethylphenyl)acetamide;
(e) trans-2-[[2-[(2-isopropylphenyl)thio]cyclohexyl]thio]-N-[3-(dimethylamino)propyl]-N-methylacetamide; and (f) trans-2-[[2-[[2-isopropylphenyl]thio]cyclohexyl]thio]-N-(2-methoxyethyl)acetamide.

(f) trans-2-[[2-[[2-methoxyphenyl]thio]cyclohexyl]thio]-N-(2-methoxyethyl)acetamide.

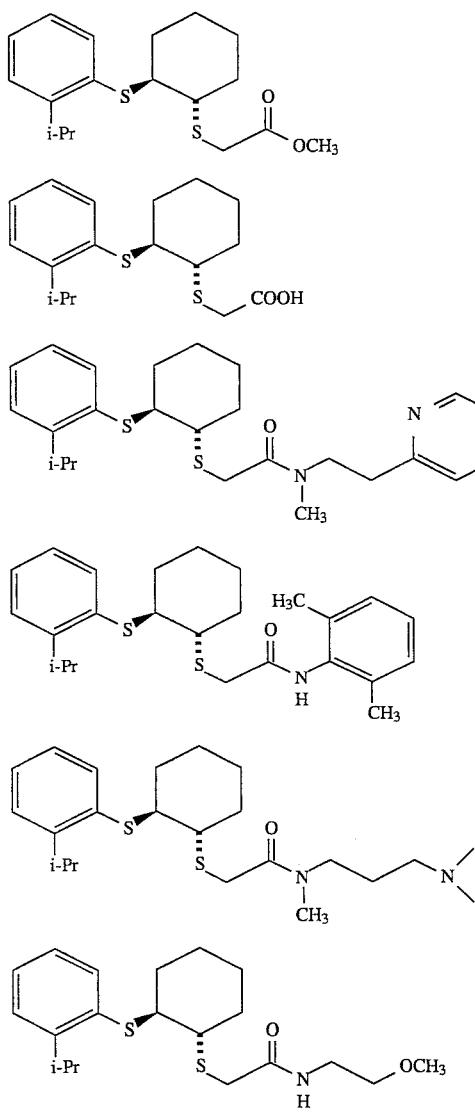

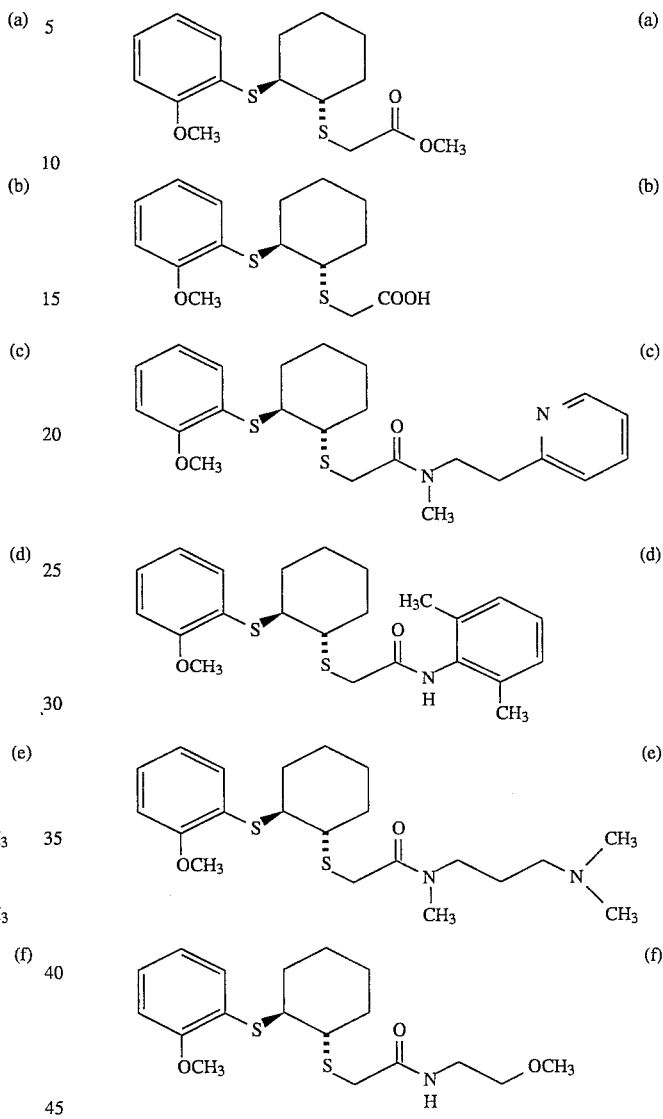

EXAMPLE 45

Starting with 2-methoxybenzenethiol and following the procedure of Example 3 gives trans-2-[(2-methoxyphenyl)thio]cyclohexanol.

Starting with this compound and following the procedures described in Examples 4, 5, 16, 22, 23, and 25 respectively gives:
(a) methyl trans-[[2-[(2-methoxyphenyl)thio]cyclohexyl]thio]acetate;
(b) trans-[[2-[(2-methoxyphenyl)thio]cyclohexyl]thio]acetic acid;
(c) trans-2-[[2-[(2-methoxyphenyl)thio]cyclohexyl]thio]-N-methyl-N-(2-pyridinylethyl)acetamide;
(d) trans-2-[[2-[(2-methoxyphenyl)thio]cyclohexyl]thio]-N-(2,6-dimethylphenyl)acetamide;
(e) trans-2-[[2-[[2-methoxyphenyl]thio]cyclohexyl]thio]-N-[3-(dimethylamino)propyl]-N-methylacetamide; and

EXAMPLE 46

Starting with 3-methoxybenzenethiol and following the procedure of Example 3 gives trans-2-[(3-methoxyphenyl)thio]cyclohexanol.

Starting with this compound and following the procedures described in Examples 4, 5, 16, 22, 23, and 25 respectively gives:
(a) methyl trans-[[2-[(3-methoxyphenyl)thio]cyclohexyl]thio]acetate;
(b) trans-[[2-[(3-methoxyphenyl)thio]cyclohexyl]thio]acetic acid;
(c) trans-[[2-[(3-methoxyphenyl)thio]cyclohexyl]thio]-N-methyl-N-(2pyridinylethyl)acetamide;
(d) trans-2-[[2-[(3-methoxyphenyl)thio]cyclohexyl]thio]-N-(2,6-dimethylphenyl)acetamide;
(e) trans-2-[[2-[[3-methoxyphenyl]thio]cyclohexyl]thio]-N-[3-(dimethylamino)propyl]-N-methylacetamide; and (f) trans-2-[[2-[[3-methoxyphenyl]thio]cyclohexyl]thio]-N-(2-methoxyethyl)acetamide.

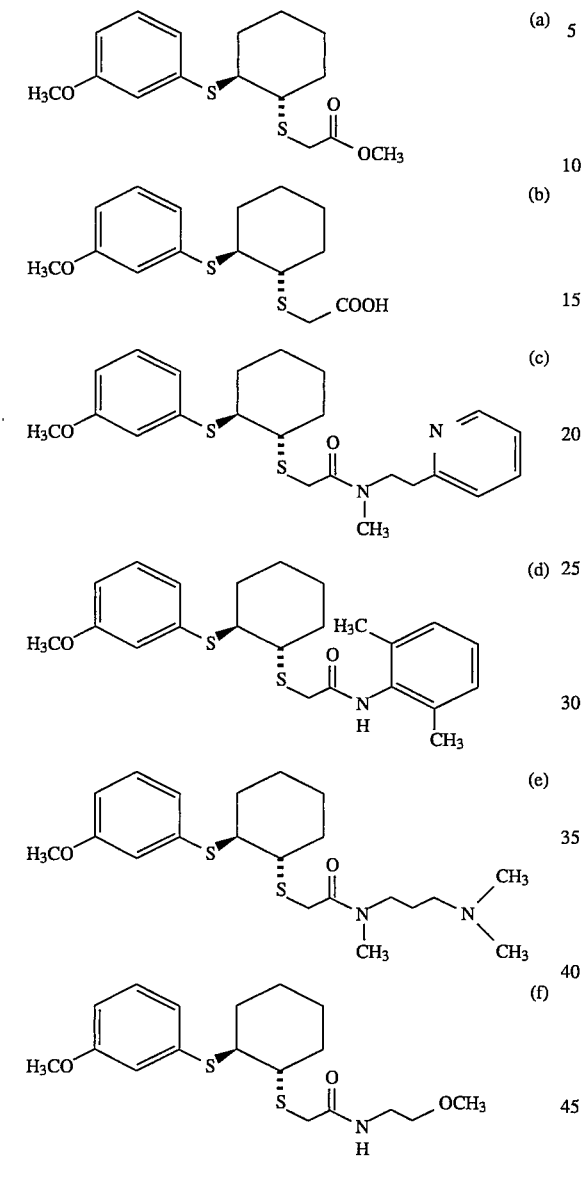

EXAMPLE 47

Starting with 4-methoxybenzenethiol and following the procedure of Example 3 gives trans-2-[(4-methoxyphenyl)thio]cyclohexanol.

Starting with this compound and following the procedures described in Examples 4, 5, 16, 22, 23, and 25 respectively gives:
(a) methyl trans-[[2-[(4-methoxyphenyl)thio]cyclohexyl]thio]acetate;
(b) trans-[[2-[(4-methoxyphenyl)thio]cyclohexyl]thio]acetic acid;
(c) trans-[[2-[(4-methoxyphenyl)thio]cyclohexyl]thio]-N-methyl-N-(2-pyridinylethyl)acetamide;
(d) trans-2-[[2-[(4-methoxyphenyl)thio]cyclohexyl]thio]-N-(2,6-dimethylphenyl)acetamide;
(e) trans-2-[[2-[[4-methoxyphenyl]thio]cyclohexyl]thio]-N-[3-(dimethylamino)propyl]-N-methylacetamide; and (f) trans-2-[[2-[[4-methoxyphenyl]thio]cyclohexyl]thio]-N-(2-methoxyethyl)acetamide.

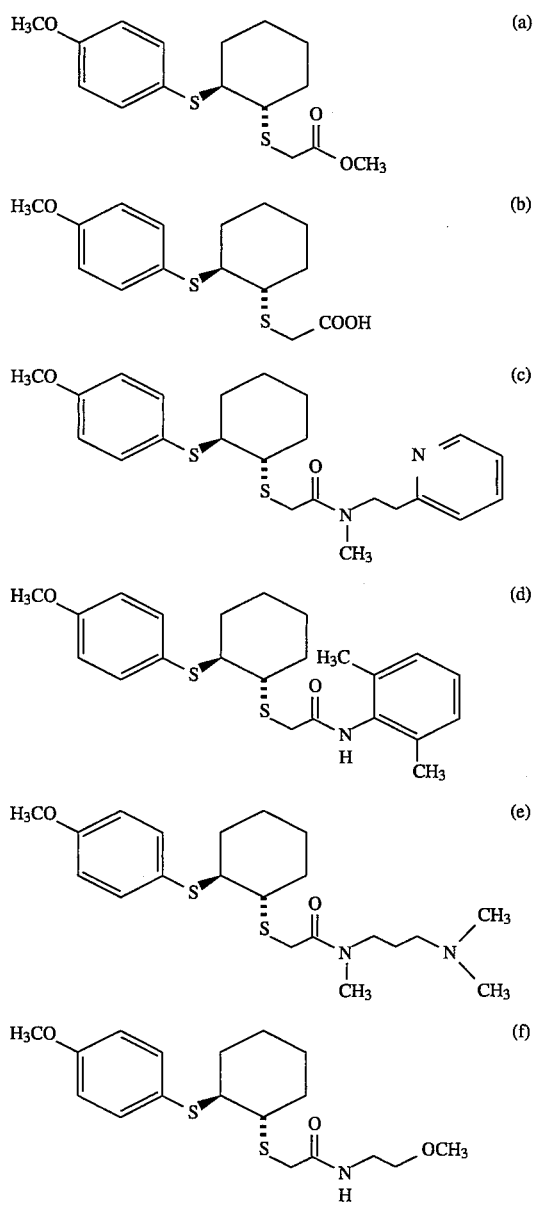

EXAMPLE 48

Starting with o-thiocresol and following the procedure of Example 3 gives trans-2-[(2-methylphenyl)thio]cyclohexanol.

Starting with this compound and following the procedures described in Examples 4, 5, 16, 22, 23, and 25 respectively gives:
(a) methyl trans-[[2-[(2-methylphenyl)thio]cyclohexyl]thio]acetate;
(b) trans-[[2-[(2-methylphenyl)thio]cyclohexyl]thio]acetic acid;
(c) trans-2-[[2-[(2-methylphenyl)thio]cyclohexyl]thio]-N-methyl-N-(2-pyridinylethyl)acetamide;
(d) trans-2-[[2-[(2-methylphenyl)thio]cyclohexyl]thio]-N-(2,6-dimethylphenyl)acetamide;
(e) trans-2-[[2-[[2-methylphenyl]thio]cyclohexyl]thio]-N-[3-(dimethylamino)propyl]-N-methylacetamide; and (f) trans-2-[[2-[[2-methylphenyl]thio]cyclohexyl]thio]-N-(2-methoxyethyl)acetamide.

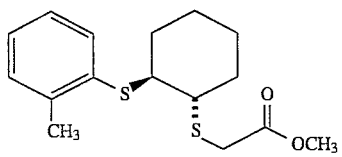
(a)

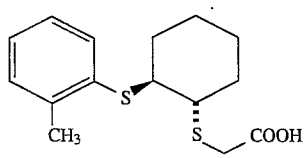
(b)

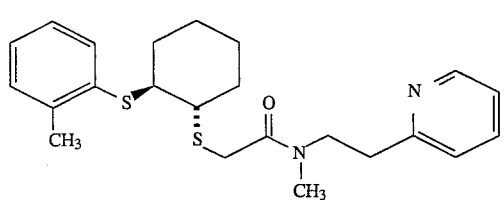
(c)

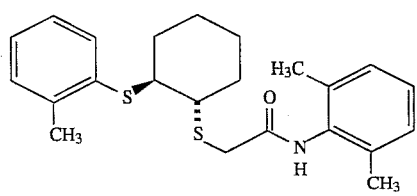
(d)

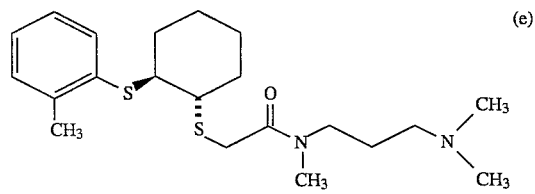
(e)

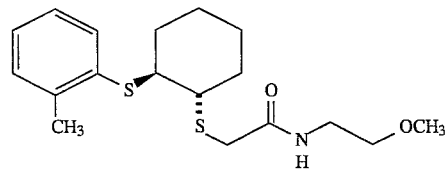
(f)

(f) trans-2-[[2-[[4-methylphenyl]thio]cyclohexyl]thio]-N-(2-methoxyethyl)acetamide.

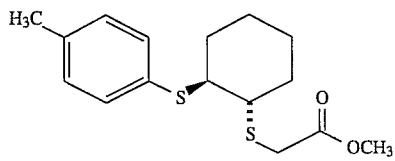
(a)

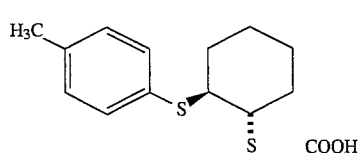
(b)

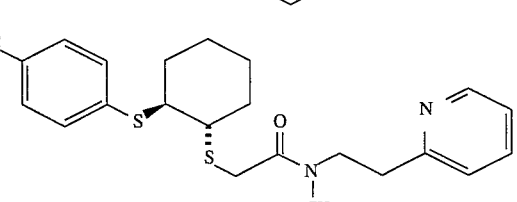
(c)

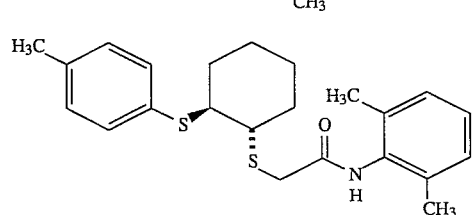
(d)

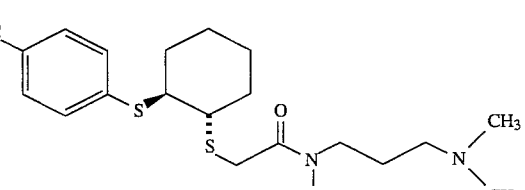
(e)

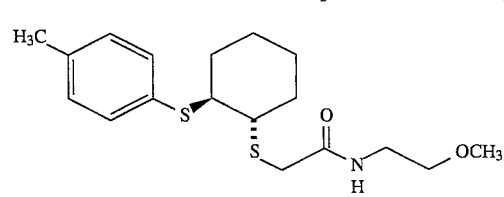
(f)

EXAMPLE 49

Starting with p-thiocresol and following the procedure of Example 3 gives trans-2-[(4-methylphenyl)thio]cyclohexanol.

Starting with this compound and following the procedures described in Examples 4, 5, 16, 22, 23, and 25 respectively gives:
(a) methyl trans-[[2-[(4-methylphenyl)thio]cyclohexyl]thio]acetate;
(b) trans-[[2-[(4-methylphenyl)thio]cyclohexyl]thio]acetic acid;
(c) trans-2-[[2-[(4-methylphenyl)thio]cyclohexyl]thio]-N-methyl-N-(2-pyridinylethyl)acetamide;
(d) trans-2-[[2-[(4-methylphenyl)thio]cyclohexyl]thio]-N-(2,6-dimethylphenyl)acetamide;
(e) trans-2-[[2-[(4-methylphenyl)thio]cyclohexyl]thio]-N-[3-(dimethylamino)propyl]-N-methylacetamide; and

EXAMPLE 50

Starting with 2-chlorobenzyl mercaptan and following the procedure of Example 3 gives trans-2-[[2-chlorophenyl)methyl]thio]cyclohexanol.

Starting with this compound and following the procedures described in Examples 4, 5, 16, 22, 23, and 25 respectively gives:
(a) methyl trans-[[2-[[(2-chlorophenyl)methyl]thio]cyclohexyl]thio]acetate;
(b) trans-[[2-[[(2-chlorophenyl)methyl]thio]cyclohexyl]thio]acetic acid;
(c) trans-[[2-[[(2-chlorophenyl)methyl]thio]cyclohexyl]thio]-N-methyl-N-(2-pyridinylethyl)acetamide;
(d) trans-2-[[2-[[(2-chlorophenyl)methyl]thio]cyclohexyl]thio]-N-(2,6-dimethylphenyl)acetamide;
(e) trans-2-[[2-[[(2-chlorophenyl)methyl]thio]cyclohexyl]thio]-N-[3-(dimethylamino)propyl]-N-methylacetamide; and (f) trans-2-[[2-[[(2-chlorophenyl)methyl]thio]cyclohexyl]thio]-N-(2-methoxyethyl)acetamide.

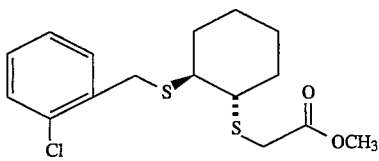
(a)

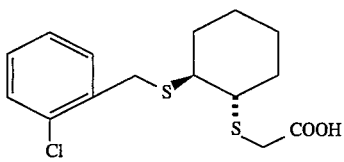
(b)

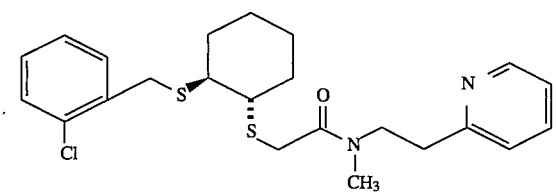
(c)

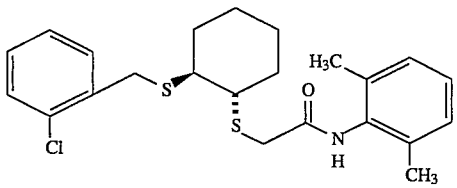
(d)

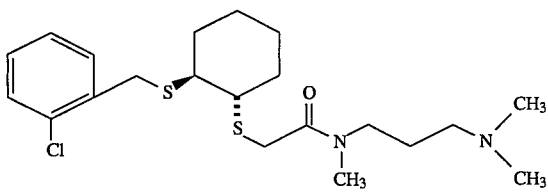
(e)

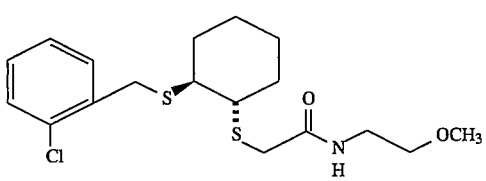
(f)

EXAMPLE 51

Starting with 4-chlorobenzyl mercaptan and following the procedure of Example 3 gives trans-2-[[(4-chlorophenyl)methyl]thio]cyclohexanol.

Starting with this compound and following the procedures described in Examples 4, 5, 16, 22, 23, and 25 respectively gives:

(a) methyl trans-[[2-[[(4-chlorophenyl)methyl]thio]cyclohexyl]thio]acetate;

(b) trans-[[2-[[(4-chlorophenyl)methyl]thio]cyclohexyl]thio]acetic acid;

(c) trans-[[2-[[(4-chlorophenyl)methyl]thio]cyclohexyl]thio]-N-methyl-N-(2-pyridinylethyl)acetamide;

(d) trans-2-[[2-[[(4-chlorophenyl)methyl]thio]cyclohexyl]thio]-N-(2,6-dimethylphenyl)acetamide;

(e) trans-2-[[2-[[(4-chlorophenyl)methyl]thio]cyclohexyl]thio]-N-[3-(dimethylamino)propyl]-N-methylacetamide; and (f) trans-2-[[2-[[(4-chlorophenyl)methyl]thio]cyclohexyl]thio]-N-(2-methoxyethyl)acetamide.

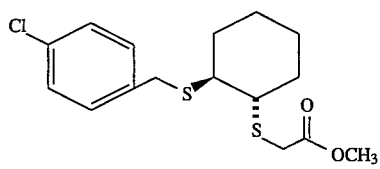
(a)

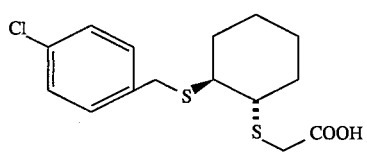
(b)

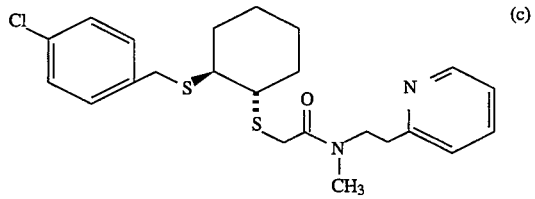
(c)

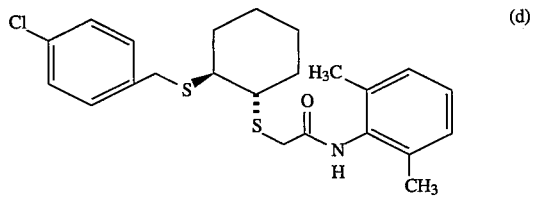
(d)

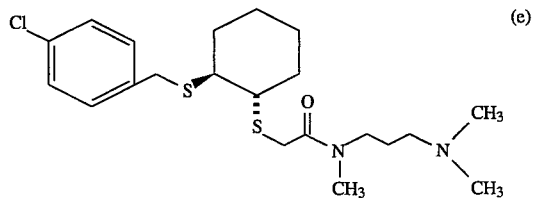
(e)

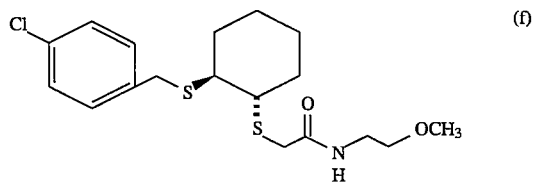
(f)

EXAMPLE 52

(1R-trans)-2-[[3,5-bis(1,1-dimethylethyl)phenyl]thio]cyclohexanol (Compound A) (52)

(1R-cis)-2-[[3,5-bis(1,1-dimethylethyl)phenyl]thio]cyclohexanol (Compound B) (52)

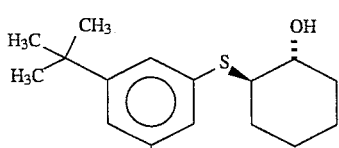
Compound A
trans

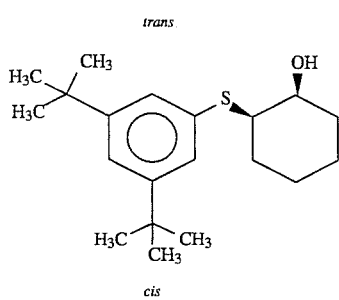
Compound B
cis

Sodium borohydride (0.40 g, 0.0105 mole) was added to a cold (3° C.) solution of 2-[[3,5-bis(1,1-dimethylethyl)phenyl]thio]cyclohexanone (3.18 g, 0.0100 mole) in methanol (150 mL). After 1 hour, 10% hydrochloric acid (5 mL) and water (50 mL) were added. The methanol was removed by rotary evaporator and the title products were extracted into ethyl acetate. The combined extracts were dried over sodium sulfate, filtered and concentrated to an oil. Silica gel chromatography separated the two title products. The major product (first off) was identified as the "cis" product by NMR.

Analysis calculated for $C_{20}H_{32}OS$: Theory: C, 74.94; H, 10.06; S, 10.00. Found: C, 74.78; H, 10.18; S, 10.04.

The minor product was shown by NMR to be identical to the compound shown in Example 3.

EXAMPLE 53

(a) 2-[[4-(1,1-dimethylethyl phenyl]thio]cycloheptanone (53) (a)

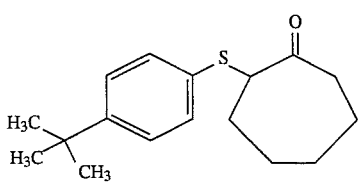

Following the method of Example 26 and substituting 2-chlorocycloheptanone for 2-chlorocyclohexanone gives the title compound.

(b) 2-[[3,5-bis(1,1-dimethylethyl)phenyl]thio]cyclooctanone (53) (b)

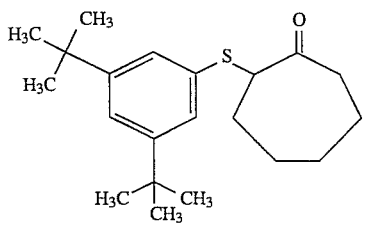

Following the method of Example 27 and substituting 2-chlorocyclooctanone for 2-chlorocyclohexanone gives the title compound.

EXAMPLE 54

(a) trans-2-[[4-(1,1-dimethylethyl)phenyl]thio]cycloheptanol (54) (a)

(b) cis-2-[[4-(1,1-dimethylethyl)phenyl]thio]cycloheptanol (54) (b)

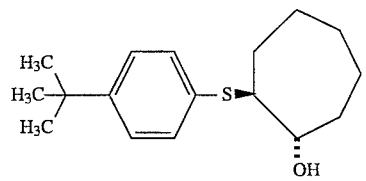
Compound A

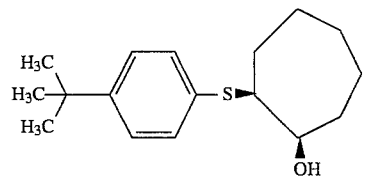
Compound B

Starting with 2-[[4-(1,1(dimethylethyl)phenyl]thio]cycloheptanone and following the procedure described in Example 52 gives the title compounds.

EXAMPLE 55

(a) Methyl trans-[[2-[[4-(1,1-dimethylethyl)phenyl]thio]cycloheptyl]thio]acetate (Compound A) (55)

(b) trans-[[2-[[4-(1,1-dimethylethyl)phenyl]thio]cycloheptyl]thio]acetic acid (Compound B) (55)

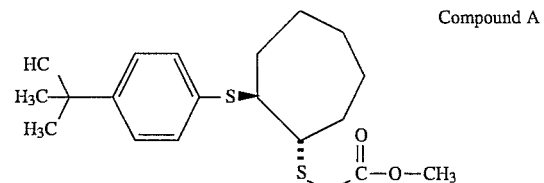
Compound A

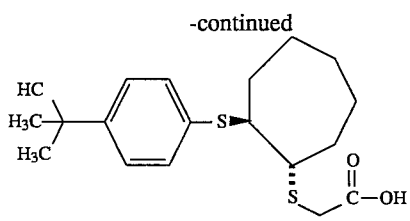
Compound B

Starting with trans-2-[[4-(1,1-dimethylethyl)phenyl]thio]cycloheptanol and following the procedures described in Examples 4 and 5 gives the title compounds.

EXAMPLE 56 trans-2-[[-2-[1,1'-biphenyl]-3-ylthiocyclohexyl]thio]-N-(2,6-dimethylphenyl)N-ethyl acetamide (56)

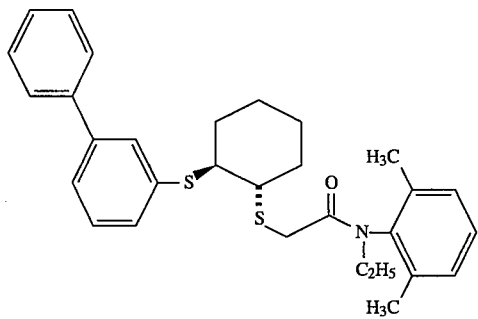

Following the procedure of Example 22 and substituting 2,6-dimethyl-N-ethylaniline for 2,6-dimethylaniline gives the title compound.

EXAMPLE 57

(a) trans-2-[[3,5-bis(1,1-dimethylethyl)phenyl]thio]cyclooctanol (Compound A) (57)

(b) cis-2-[[3,5-bis(1,1-dimethylethyl)phenyl]thio]cyclooctanol (Compound B) (57)

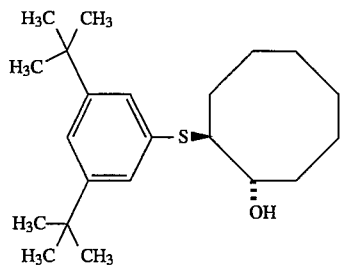
Compound A

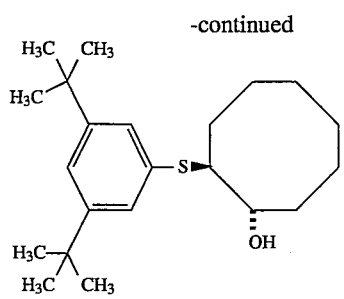
Compound B

Starting with 2-[[3,5-bis(1,1(dimethylethyl)phenyl]thio]cyclooctanone and following the procedure described in Example 52 gives the title compounds.

EXAMPLE 58

(a) Methyl trans-[[2-[[3,5-bis(1,1-dimethylethyl)phenyl]thio]cyclooctyl]thio]acetate (Compound A) (58)

(b) trans-[[2 -[[3,5-bis(1,1-dimethylethyl)phenyl]thio]cyclooctyl]thio]acetic acid (Compound B) (58)

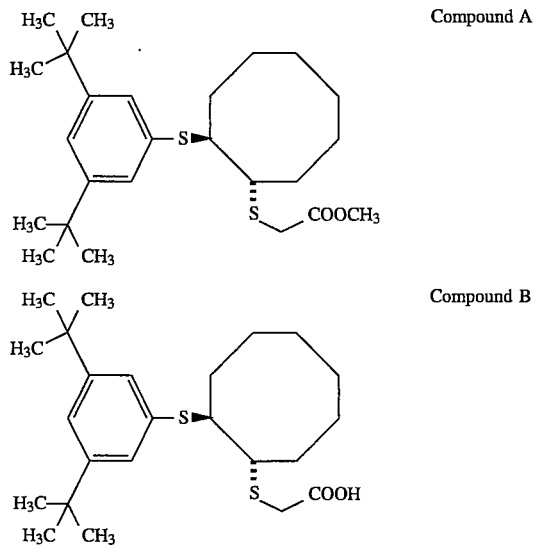

Starting with trans-2-[[3,5-bis(1,1-dimethylethyl)phenyl]thio]cyclooctanol and following the procedures described in Examples 4 and 5 gives the title compounds.

EXAMPLE 59

Substituting the compound listed in column A of Table 3 below for 3,5-bis(1,1-dimethylethyl)benzenethiol, and following the procedure of Example 19, and then substituting the resulting furanol for the cyclohexanol used in Example 17, and following the procedure of Example 17, gives the compound of the Formula XXX in which W is the moiety listed in the second column of Table 3 below.

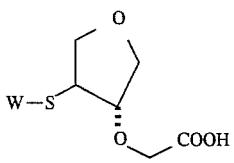

XXX

TABLE 3

| A | W |
|---|---|
| (a) 2-bromothiophenol | 2-bromophenyl |
| (b) 3-bromothiophenol | 3-bromophenyl |
| (c) 4-bromothiophenol | 4-bromophenyl |
| (d) 2,5-dichlorobenzenethiol | 2,5-dichlorophenyl |
| (e) 2-chlorothiophenol | 2-chlorophenyl |
| (f) 3-chlorothiophenol | 3-chlorophenyl |
| (g) 4-chlorothiophenol | 4-chlorophenyl |
| (h) 2,6-dichlorobenzenethiol | 2,6-dichlorophenyl |
| (i) 3,4-dichlorobenzenethiol | 3,4-dichlorophenyl |
| (j) 2,4-dimethylthiophenol | 2,4-dimethylphenyl |
| (k) 2,5-dimethylthiophenol | 2,5-dimethylphenyl |
| (l) 3,4-dimethylthiophenol | 3,4-dimethylphenyl |
| (m) 2-chlorobenzyl mercaptan | 2-chlorobenzyl |
| (n) 4-chlorobenzyl mercaptan | 4-chlorobenzyl |
| (o) 4-fluorothiophenol | 4-fluorophenyl |
| (p) 4-hydroxythiophenol | 4-hydroxyphenyl |
| (q) 2-isopropylthiophenol | 2-isopropylphenyl |
| (r) 2-methoxybenzenethiol | 2-methoxyphenyl |
| (s) 3-methoxybenzenethiol | 3-methoxyphenyl |
| (t) 4-methoxybenzenethiol | 4-methoxyphenyl |
| (u) o-thiocresol | 2-methylphenyl |
| (v) p-thiocresol | 4-methylphenyl |

EXAMPLE 60

Following the procedure of Example 22, and substituting the aniline listed in column B of Table 4 below for 2,6-dimethylaniline, gives the compound of Formula XXXI in which Z is the moiety listed in the second column (Z) of Table 4 below.

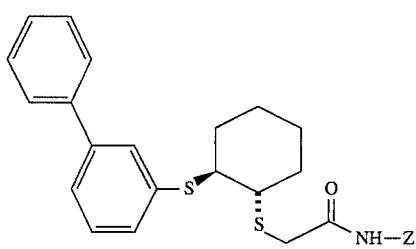

XXXI

TABLE 4

| B | Z |
|---|---|
| (a) 2-bromo-4-methylaniline | 2-bromo-4-methylphenyl |
| (b) 4-bromo-2-methylaniline | 4-bromo-2-methylphenyl |
| (c) 4-t-butylaniline | 4-t-butylphenyl |
| (d) 2-chloro-6-methylaniline | 2-chloro-6-methylphenyl |
| (e) 2,6-dibromo-4-methylaniline | 2,6-dibromo-4-methylphenyl |
| (f) 2,6-diethylaniline | 2,6-diethylphenyl |
| (g) 2,6-difluoroaniline | 2,6-difluorophenyl |
| (h) 2,6-diisopropylaniline | 2,6-diisopropylphenyl |
| (i) 2,5-dimethoxyaniline | 2,5-dimethoxyphenyl |
| (j) 2,5-dimethylaniline | 2,5-dimethylphenyl |
| (k) 3,5-dimethylaniline | 3,5-dimethylphenyl |
| (l) 4,6-dimethyl-2-nitroaniline | 4,6-dimethyl-2-nitrophenyl |

TABLE 4-continued

| B | Z |
|---|---|
| (m) 6-ethyl-o-toluidine | 6-ethyl-o-phenyl |
| (n) 4-hexylaniline | 4-hexylphenyl |
| (o) 4-hexyloxyaniline | 4-hexyloxyphenyl |
| (p) 4-iodoaniline | 4-iodophenyl |
| (q) 5-methoxy-2-methyl-4-nitroaniline | 5-methoxy-2-methyl-4-nitrophenyl |
| (r) 3-(methylmercapto)aniline | 3-(methylmercapto)-phenyl |
| (s) 4-octylaniline | 4-octylphenyl |
| (t) 2-propylaniline | 2-propylphenyl |
| (u) 3,5-bis(trifluoromethyl)-aniline | 3,5-bis(trifluoromethyl)phenyl |
| (v) 2,4,6-trimethylaniline | 2,4,6-trimethylphenyl |

EXAMPLE 61

Substituting the compound listed in column A of Table 3 above for 3,5-bis(1,1-dimethylethyl)benzenethiol, and following the procedure of Example 19, and then substituting the resulting furanol for the trans-2-[([1,1'-biphenyl]-3-yl)thio]cyclohexanol used in Example 22, and also substituting the aniline listed in column B of Table 4 above for the 2,6-dimethylaniline used in Example 22, and following the procedure described in Example 22, gives the compound of formula XXXI(a) in which W is the moiety listed in the second column (w) of Table 3 above and Z is the moiety listed in the second column (Z) of Table 4 above.

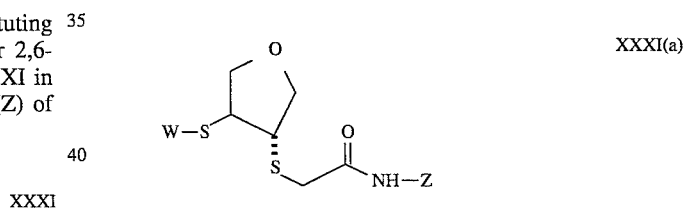

XXXI(a)

EXAMPLE 62 trans[[-2-[[3,5-bis(1,1-dimethylethyl)phenyl]thio]cyclohexyl]thio]-N-(2,6-dimethylphenyl)acetamide (62)

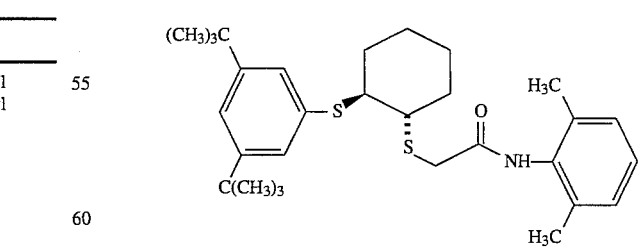

Following the procedure of Example 22 and substituting trans-2-[[3,5-bis(1,1-dimethylethyl)phenyl]thio]-cyclohexanol for trans-2-([1,1'-biphenyl]-3-yl)]thio]cyclohexanol gives the title compound.

EXAMPLE 63

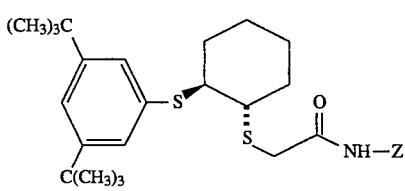

XXXII

Following the procedure of Example 22 and substituting trans-2-[[3,5-bis(1,1-dimethylethyl)phenyl]thio]cyclohexanol for trans-2-[([1,1'-biphenyl]-3-yl)]thio]cyclohexanol used therein, and also substituting the aniline listed in column B of Table 4 above for 2,6-dimethylaniline, gives the compound of Formula XXXII in which Z is the moiety listed in the second column of Table 4 above.

EXAMPLE 64

(a) Substituting the compound listed in column A of Table 3 above for 3,5-bis(1,1-dimethylethyl)benzenethiol, and following the procedure of Example 3, and then substituting the resulting cyclohexanol for the trans-2-[[3,5-bis(1,1-dimethylethyl)phenyl]thio]cyclohexanol used in Example 17, and following the procedure of Example 17, gives the compound of the Formula XXXIII(a) in which W is the moiety listed in the second column (W) of Table 3 above.

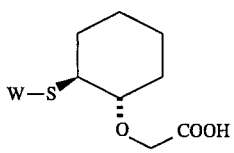

XXXIII(a)

(b) Substituting the compound listed in column A of Table 3 above for 3,5-bis(1,1-dimethylethyl)benzenethiol, and following the procedure of Example 3, and then substituting the resulting cyclohexanol for the trans-2-[[(1,1'-biphenyl)-3-yl] thio]cyclohexanol used in Example 22, and also substituting the aniline listed in column B of Table 4 above for the 2,6-dimethylaniline used in Example 22, and following the procedure described in Example 22, gives the compound of Formula XXXIII(b) in which W is the moiety listed in the second column (W) of Table 3 above and Z is the moiety listed in the second column (Z) of Table 4.

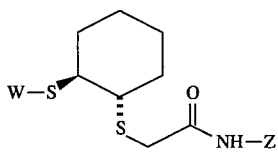

XXXIII(b)

EXAMPLE 65

Substituting the compound listed in column A of Table 3 above for 3,5-bis(1,1-dimethylethyl) benzenethiol in Example 3, and also substituting cyclopentene oxide for cyclohexene oxide in Example 3, and then following Examples 3, 4 and 5, respectively, gives the compounds of (a) Formula XXXIV, (b) Formula XXXV, and (c) Formula XXXVI below in which W is the moiety listed in the second column of Table 3 above.

Ex. 65(a)

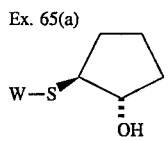

XXXIV

Ex. 65(b)

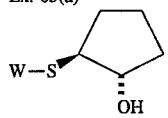

XXXV

Ex. 65(c)

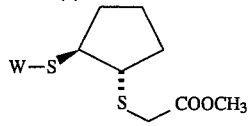

XXXVI

EXAMPLE 66

Following the procedure of Example 23, and substituting the amine listed in column C of Table 5 below for N,N,N'-trimethyl-1,3-propane diamine, gives the compound of Formula XXXVII below in which Y is the moiety listed in the second column (Y) of Table 5 below.

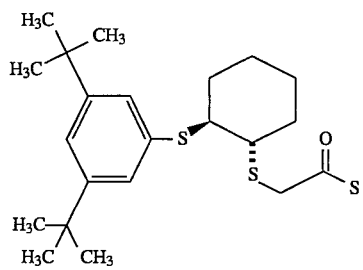

XXXVII

TABLE 5

| C | Y |
|---|---|
| (a) dimethylamine | —N(CH₃)₂ |
| (b) diethylamine | —N(C₂H₅)₂ |
| (c) diisopropylamine | —N[CH(CH₃)₂]₂ |
| (d) dibutylamine | —N[(CH₂)₃CH₃]₂ |
| (e) dihexylamine | —N[(CH₂)₅CH₃]₂ |
| (f) diisobutylamine | —N[CH₂CH(CH₃)₂]₂ |
| (g) hexylamine | —NH(CH₂)₅CH₃ |
| (h) butylamine | —NH(CH₂)₃CH₃ |
| (i) octylamine | —NH(CH₂)₇CH₃ |
| (j) t-butylamine | —NHC(CH₃)₃ |
| (k) 3,3-dimethylbutylamine | —NHCH₂CH₂C(CH₃)₃ |
| (l) dipentylamine | —N[(CH₂)₄CH₃]₂ |
| (m) 1-ethylpropylamine | —NHCH(C₂H₅)₂ |
| (n) 1-cyclohexylethylamine | —NH[CH(CH₃)C₆H₁₁] |
| (o) methylphenylamine | —NH[(CH₃)C₆H₅] |

EXAMPLE 67

(a) Substituting N,N-diethyl-1,4-pentane diamine for the N,N,N'-trimethyl-1, 3-propane diamine of Example 23, and following the procedure described therein, gives trans-2-[ [2-[[3,5-bis(1,1-dimethylethyl)phenyl]thio]cyclohexyl]thio] -N-[4diethylamino)pentyl]acetamide.

(b) Substituting 4-(2-aminoethyl)morpholine for the N,N, N'-trimethyl-1,3-propane diamine of Example 23, and following the procedure described therein, gives trans-2-[[2-[ [3,5-bis(1,1-dimethylethyl)phenyl]thio]cyclohexyl]thio]-N-(4-morpholinylethyl)acetamide.

(c) Substituting 1-(2-aminoethyl)piperidine for the N,N,N'-trimethyl-1,3-propane diamine of Example 23, and following the procedure described therein, gives trans-2-[[2-[[3,5-bis(1,1-dimethylethyl)phenyl]thio]cyclohexyl]thio]-N-(1-piperidinylethyl)acetamide.

(d) Substituting 1-(2-aminoethyl)pyrrolidine for the N,N,N'-trimethyl-1,3-propane diamine of Example 23, and following the procedure described therein, gives trans-2-[[2-[[3,5-bis(1,1-dimethylethyl)phenyl]thio]cyclohexyl]thio]-N-(1-pyrrolidinylethyl)acetamide.

(e) Substituting 1-(3-aminopropyl)-2-methylpiperidine for the N,N,N'-trimethyl-1,3-propane diamine of Example 23, and following the procedure described therein, gives trans-2-[[2-[[3,5-bis(1,1-dimethylethyl)phenyl]thio]cyclohexyl]thio]-N-[(2-methylpiperidin-1-yl)propyl]acetamide.

(f) Substituting N,N-diethyl-1,3-propane diamine for the N,N,N'-trimethyl-1,3-propane diamine of Example 23, and following the procedure described therein, gives trans-2-[[2-[[3,5-bis(1,1-dimethylethyl)-phenyl]thio]cyclohexyl]thio]-N-[3-(diethylamino)-propyl]acetamide.

(g) Substituting 4-diisopropylaminobutylamine for the N,N,N'-trimethyl-1,3-propane diamine of Example 23 and following the procedure described therein, gives trans-2-[[2-[[3,5-bis(1,1-dimethylethyl)phenyl]thio]cyclohexyl]thio]-N-[4-(diisopropylamino)butyl]acetamide.

(h) Substituting N,N-diethyl-N'methyl-1,3-diaminopropane for the N,N,N'-trimethyl-1,3-propane diamine of Example 23, and following the procedure described therein, gives trans-2-[[2-[[3,5-bis(1,1-dimethylethyl)phenyl]thio]cyclohexyl]thio]-N-[3-(diethylamino)propyl]-N-methylacetamide.

(i) Substituting N,N-diethyl-N'-methylethylenediamine for the N,N,N'-trimethyl-1,3-propane diamine of Example 23, and following the procedure described therein, gives trans-2-[[2-[[3,5-bis(1,1-dimethylethyl)phenyl]thio]cyclohexyl]thio]-N-[(diethylamino)ethyl]-N-methylacetamide.

(j) Substituting N,N,N'-trimethylethylenediamine for the N,N,N'-trimethyl-1,3-propane diamine of Example 23, and following the procedure described therein, gives trans-2-[[2-[[3,5-bis(1,1-dimethylethyl)phenyl]thio]cyclohexyl]thio]-N-[(dimethylamino)ethyl]-N-methylacetamide.

a)

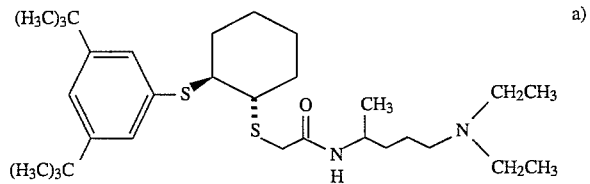

b)

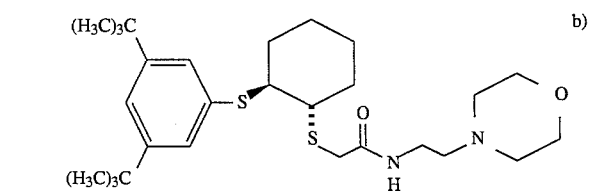

c)

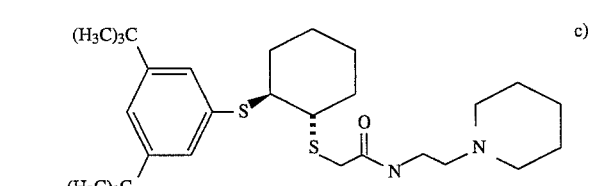

-continued d)

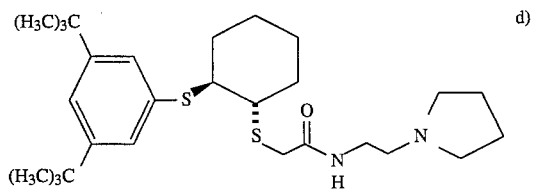

e)

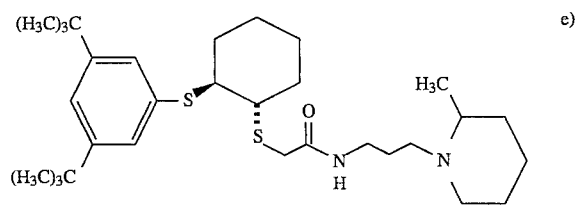

f)

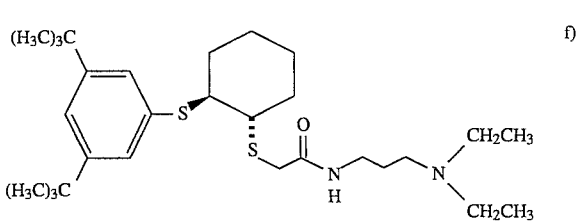

g)

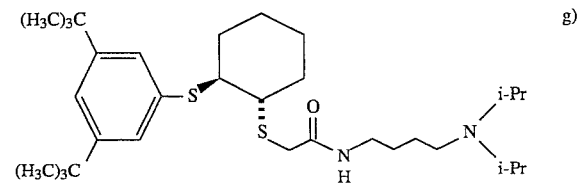

h)

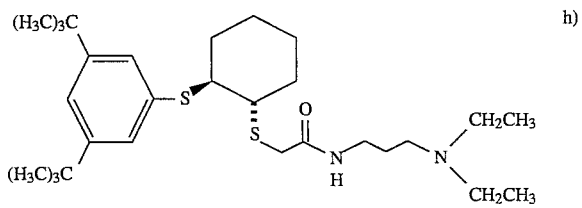

i)

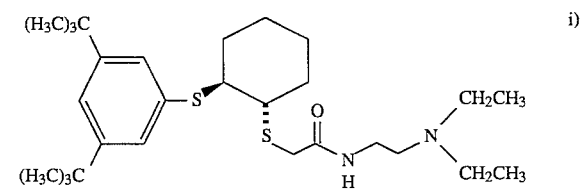

j)

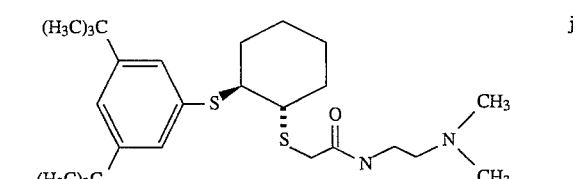

EXAMPLE 68

(a) Substituting 4-(ethylaminomethyl)pyridine for the 2-(2-methylaminoethyl)pyridine of Example 16, and following the procedure described therein, gives trans-2-[[2-[[3,5-bis(1,1-dimethylethyl)phenyl]thio]cyclohexyl]thio]-N-ethyl-N-(4-pyridinylmethyl)acetamide.

(b) Substituting 2-(2-aminoethylamino)-5-nitropyridine for the 2-(2-methylaminoethyl)pyridine of Example 16, and following the procedure described therein, gives trans-2-[[2-[[3,5-bis(1,1-dimethylethyl)phenyl]thio]cyclohexyl]thio]-N-[[(5-nitropyridin-2-yl)amino]ethyl]acetamide.

(c) Substituting 2-(2-aminoethyl)-1-methylpyrrolidine for the 2-(2-methylaminoethyl)pyridine of Example 16, and following the procedure described therein, gives trans-2-[[2-[[3,5-bis(1,1-dimethylethyl)phenyl]thio]cyclohexyl]thio]-N-[(1-methylpyrrolidin-2-yl)ethyl]acetamide.

(d) Substituting 2-(2-aminoethyl)pyridine for the 2-(2-methylaminoethyl)pyridine of Example 16, and following the procedure described therein, gives trans-2-[[2-[[3,5-bis(1,1-dimethylethyl)phenyl]thio]cyclohexyl]thio]-N-(2-pyridinylethyl)acetamide.

(e) Substituting 2-(aminomethyl)pyridine for the 2-(2-methylaminoethyl)pyridine of Example 16, and following the procedure described therein, gives trans-2-[[2-[[3,5-bis(1,1-dimethylethyl)phenyl]thio]cyclohexyl]thio]-N-(2-pyridinylmethyl)-acetamide.

(f) Substituting 3-(aminomethyl)pyridine for the 2-(2-methylaminoethyl)pyridine of Example 16, and following the procedure described therein, gives trans-2-[[2-[[3,5-bis(1,1-dimethylethyl)phenyl]thio]cyclohexyl]thio]-N-(3-pyridinylmethyl)-acetamide.

(g) Substituting 4-(aminomethyl)pyridine for the 2-(2-methylaminoethyl)pyridine of Example 16, and following the procedure described therein, gives trans-2-[[2-[3,5-bis(1,1-dimethylethyl)phenyl]thio] cyclohexyl]thio]-N-(4-pyridinylmethyl)-acetamide.

(h) Substituting 2-aminomethyl-6-methylpyridine for the 2-(2-methylaminoethyl)pyridine of Example 16, and following the procedure described therein, gives trans-2-[[2-[[3,5-bis(1,1-dimethylethyl)phenyl]thio]cyclohexyl]thio]-N-[(6-methylpyridine-2-yl)methyl]acetamide.

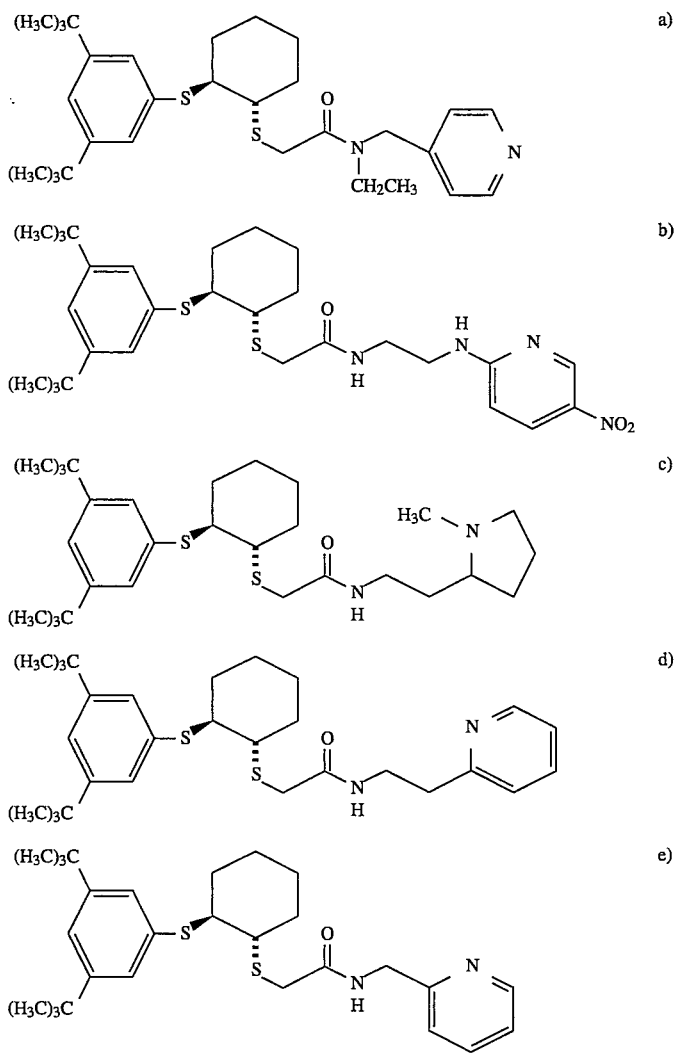

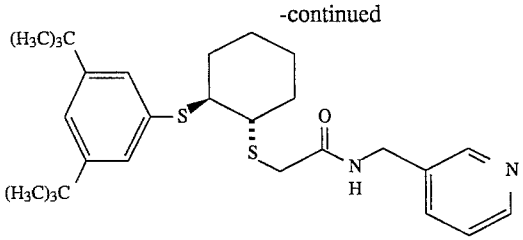

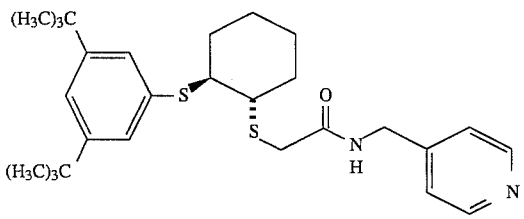

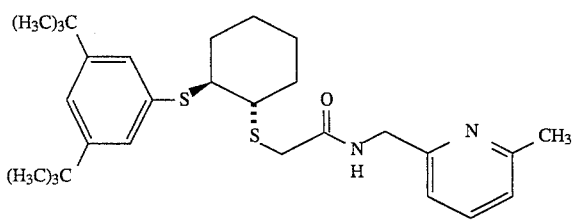

EXAMPLE 69

(a) Substituting 3-methoxypropylamine for the 2-methoxyethylamine in Example 25, and following the procedure described therein, gives trans-2-[[2-[[3,5-bis(1,1-dimethylethyl)phenyl]thio]cyclohexyl]thio]-N-(3-methoxypropyl)acetamide.

(b) Substituting 3-isopropoxypropylamine for the 2-methoxyethylamine in Example 25, and following the procedure described therein, gives trans-2-[[2-[[3,5-bis(1,1-dimethylethyl)phenyl]thio]cyclohexyl]thio]-N-(3-isopropoxypropyl)acetamide.

(c) Substituting 3-ethoxypropylamine for the 2-methoxyethylamine in Example 25, and following the procedure described therein, gives trans-2-[[2-[[3,5-bis(1,1-dimethylethyl)phenyl]thio]cyclohexyl]thio]-N-(3-ethoxypropyl)acetamide.

(d) Substituting 3-butoxypropylamine for the 2-methoxyethylamine in Example 25, and following the procedure described therein, gives trans-2-[[2-[[3,5-bis(1,1-dimethylethyl)phenyl]thio]cyclohexyl]thio]-N-(3-butoxypropyl)acetamide.

(e) Substituting 2-methylaminomethyl-1,3-dioxolane for the 2-methoxyethylamine in Example 25, and following the procedure described therein, gives trans-2-[[2-[[3,5-bis(1,1-dimethylethyl)phenyl]thio]cyclohexyl]thio]-N-methyl-N-(2-methyl-1,3-dioxolane) acetamide.

(f) Substituting furfurylamine for the 2-methoxyethylamine in Example 25, and following the procedure described therein, gives trans-2-[[2-[[3,5-bis(1,1-dimethylethyl)phenyl]thio]cyclohexyl]thio]-N-(furfuryl)acetamide.

(g) Substituting 2-thiophenemethylamine for the 2-methoxyethylamine in Example 25, and following the procedure described therein, gives trans-2-[[2-[[3,5-bis(1,1-dimethylethyl)phenyl]thio]cyclohexyl]thio]-N-(2-thiophenemethyl)acetamide. (h) Substituting tetrahydrofurfuralamine for the 2-methoxyethylamine in Example 25, and following the procedure described therein, gives trans-2-[[2-[[3,5-bis(1,1-dimethylethyl)phenyl]thio]cyclohexyl]thio]-N-(tetrahydrofurfuryl)acetamide.

a)

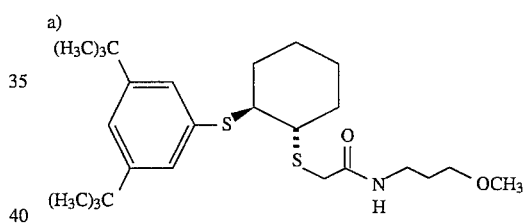

b)

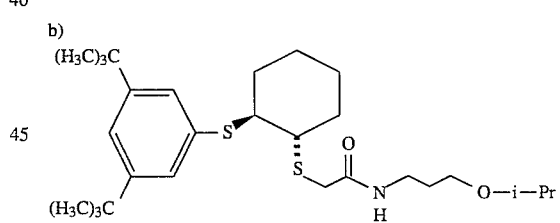

c)

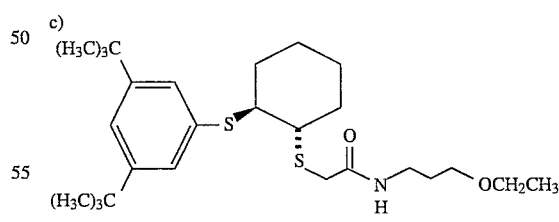

d)

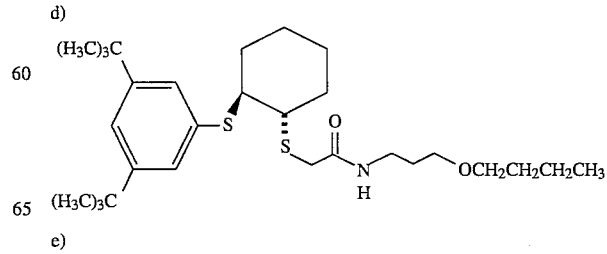

e)

-continued

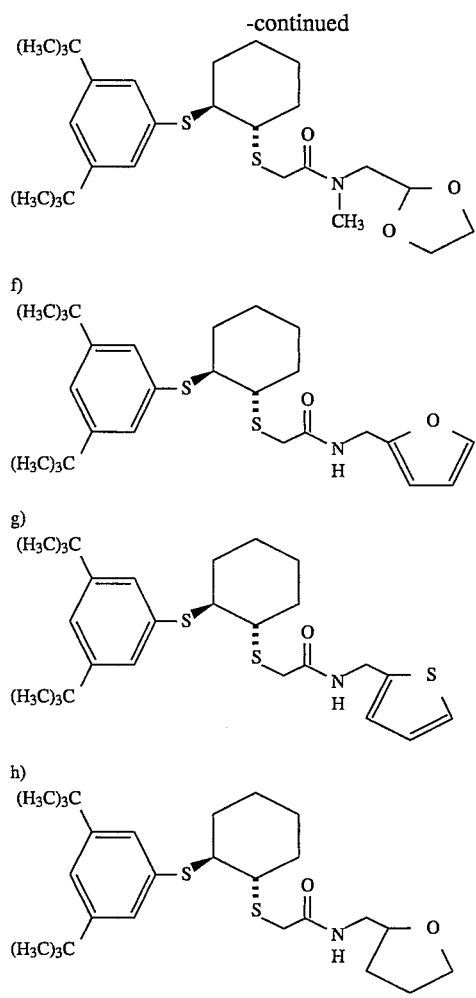

f)

g)

h)

EXAMPLE 70

(a) Substituting 2-trifluoromethylphenol for the meta-t-butyl phenol in Example 8, and following the procedures described in Examples 8, 9, 10, and 11, respectively, gives trans-[[2-[(2-trifluoromethylphenyl)thio]cyclohexyl]thio]acetic acid.

(b) Substituting 3-trifluoromethylphenol for the meta-t-butyl phenol in Example 8, and following the procedures described in Examples 8, 9, 10, and 11, respectively, gives trans-[[2-[(3-trifluoromethylphenyl)thio]cyclohexyl]thio]acetic acid.

(c) Substituting 4-trifluoromethylphenol for the meta-t-butyl phenol in Example 8, and following the procedures described in Examples 8, 9, 10, and 11, respectively, gives trans-[[2-[(4-trifluoromethylphenyl)thio]cyclohexyl]thio]acetic acid.

(d) Substituting 3,5-bis-(trifluoromethyl)phenol for the meta-t-butyl phenol in Example 8, and following the procedures described in Examples 8, 9, 10, and 11, respectively, gives trans-[[2-[[3,5-bis(trifluoromethyl)phenyl]thio]cyclohexyl]thio]acetic acid.

a)

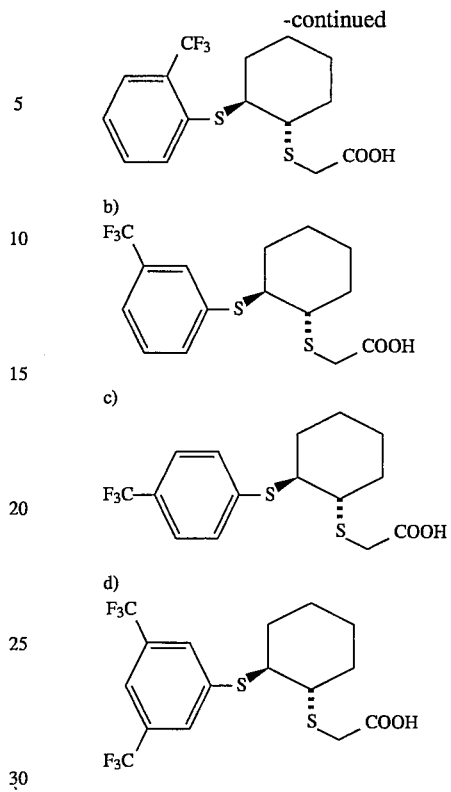

EXAMPLE 71

By substituting the products of:
(a) Example 54(a);
(b) Example 54(b);
(c) Example 57(a); and
(d) Example 57(b) respectively
for trans-2-[[3,5-bis(1,1-dimethylethyl)phenyl]thio]cyclohexanol in Example 17, and following the procedure described therein, the following products are obtained:

a)

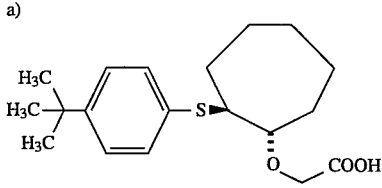

trans-2-[[2-[[4-(1,1-dimethylethyl)phenyl]thio]cycloheptyl]oxy]acetic acid b)

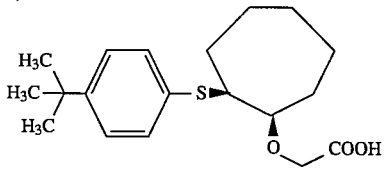

cis-2-[[2-[[4-(1,1-dimethylethyl)phenyl]thio]cycloheptyl]oxy]acetic acid c)

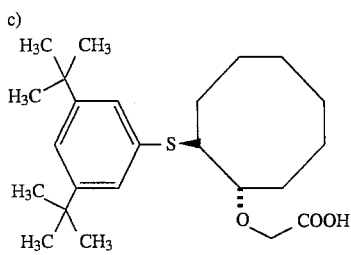

trans-2-[[2-[[3,5-bis(1,1-dimethylethyl)phenyl]thio]cyclooctyl]oxy]acetic acid d)

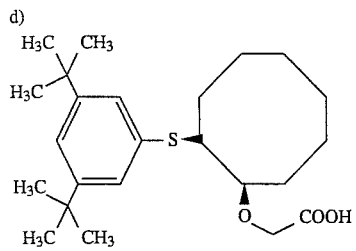

cis-2-[[2-[[3,5-bis(1,1-dimethylethyl)phenyl]thio]cyclooctyl]oxy]acetic acid

EXAMPLE 72

(±)cis-2-[[2-[[3,5-bis(1,1-dimethylethyl)phenyl]thio]cyclohexyl]oxy]acetic acid (72)

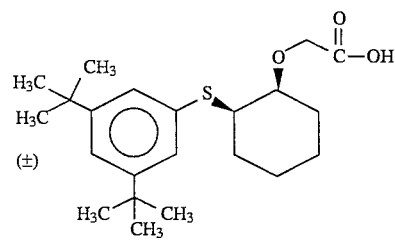

The title compound was prepared by following the method described in Example 17, except that the title product of Example 52, Compound B, was substituted for the title product of Example 3. The structure was supported by NMR, Ir and elemental analysis.

Analysis calculated for $C_{22}H_{34}O_3S$: Theory: C, 69.80; H, 9.05; S, 8.47. Found: C, 69.62; H, 9.24; S, 8.61.

EXAMPLE 73

2-[[3,5-bis(1,1-dimethylethyl)phenyl]thio]cyclopentanone (73)

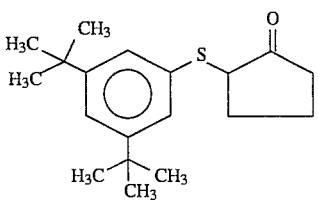

The title compound was prepared by following the method described in Example 27, except that 2-chlorocyclopentanone was substituted for 2-chlorocyclohexanone. The structure was supported by NMR, Ir and elemental analysis.

Analysis calculated for $C_{19}H_{28}OS$: Theory: C, 74.95; H, 9.27; S, 10.53. Found: C, 74.67; H, 9.59; S, 10.68.

EXAMPLE 74

(±)trans-2-[[3,5-bis(1,1-dimethylethyl)phenyl]thio]cyclopentanol (74)

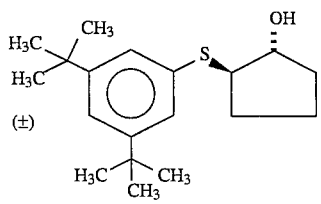

The title compound was prepared by the method described in Example 3, except that cyclopentene oxide was substituted for cyclohexene oxide. The structure was supported by NMR, Ir and elemental analysis.

Analysis calculated for $C_{19}H_{30}OS$: Theory: C, 74.45; H, 9.87; S, 10.46. Found: C, 74.12; H, 9.71; S, 10.68.

EXAMPLE 75

(±)cis-2-[[3,5-bis(1,1-dimethylethyl)phenyl]thio]cyclopentanol (75)
(Compound A)

(±)trans-2-[[3,5-bis(1,1-dimethylethyl)phenyl]thio]cyclopentanol (75)
(Compound B)

Compound A

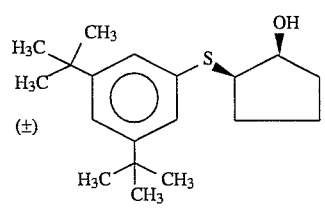

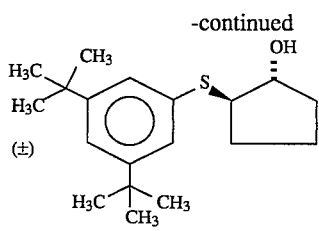

Compound B

The title compounds were prepared by the method described in Example 52 by substituting the title product of Example 73 for the title product of Example 27.

Compound A (major)—The structure was supported by NMR, Ir and elemental analysis.

Analysis calculated for $C_{19}H_{30}OS$: Theory: C, 74.45; H, 9.87; S, 10.46. Found: C, 74.58; H, 9.65; S, 10.71.

Compound B (major)—The NMR was identical to that for the title product of Example 74.

EXAMPLE 76

(±)trans-2-[[2-[[3,5-bis(1,1-dimethylethyl)phenyl]thio]cyclopentyl]oxy]acetic acid (76)

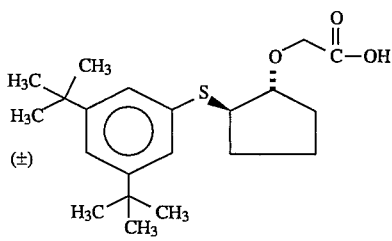

The title compound was prepared by the method described in Example 17, except that the title product of Example 74 was substituted for the title product of Example 3. The structure was supported by NMR, Ir and elemental analysis.

Analysis calculated for $C_{21}H_{32}OS$: Theory: C, 69.19; H, 8.85; S, 8.80. Found: C, 69.41; H, 8.71; S, 8.98.

EXAMPLE 77

(±)cis-2-[[2-[[3,5-bis(1,1-dimethylethyl)phenyl]phenyl]thio]cyclopentyl]oxy]acetic acid (77)

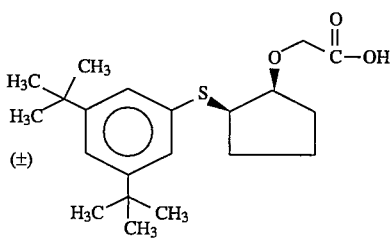

The title compound was prepared by the method described in Example 17, except that the title product of Example 75, Compound A, was substituted for the title product of Example 3. The structure was supported by NMR, Ir and elemental analysis.

Analysis calculated for $C_{21}H_{32}O_3S$: Theory: C, 69.19; H, 8.85; S, 8.80. Found: C, 69.00; H, 8.89; S, 8.93.

EXAMPLE 78

2-[[3,5-(1,1-dimethylethyl)phenyl]thio]cyclopentanone (78)

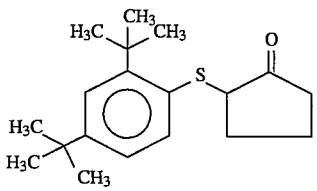

The title compound was prepared by the method described in Example 73, except that 2,4-bis(1,1-dimethylethyl)benzenethiol was substituted for 3,5bis-(1,1-dimethylethyl)benzenethiol. The structure was supported by NMR, Ir and elemental analysis.

DSC 59.32° C.

Analysis calculated for $C_{19}H_{28}OS$: Theory: C, 74.95; H, 9.27; S, 10.53. Found: C, 74.84; H, 9.33; S, 10.65.

EXAMPLE 79

(±)cis-2-[[2,4-bis(1,1-dimethylethyl)phenyl]thio]cyclopentanol (79)
(Compound A)

(±)trans-2-[[2,4-bis(1,1-dimethylethyl)phenyl]thio]cyclopentanol (79)
(Compound B)

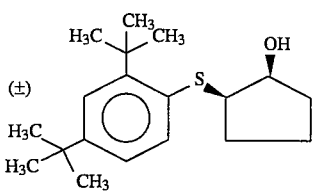

Compound A

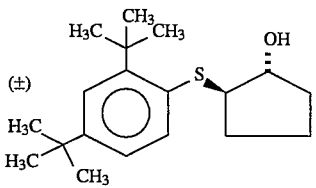

Compound B

The title compounds were prepared by the method described in Example 75, except that the title product of Example 78 was substituted for the title product of Example 73.

The structures were supported by NMR, Ir and elemental analysis (cis only).

Analysis calculated for $C_{19}H_{30}OS$: Theory: C, 74.45; H, 9.87; S, 10.46. Found: C, 74.58; H, 9.65; S, 10.71.

EXAMPLE 80

(±)cis-2-[[2-[[2,4-bis(1,1-dimethylethyl)phenyl]thio]cyclopentyl]oxy]acetic acid (80)

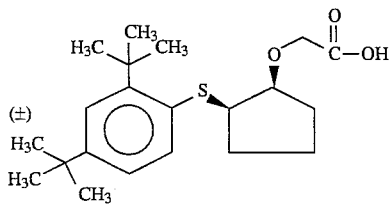

The title compound was prepared by the method described in Example 77, except that cis-2-[[2,4-bis(1,1-dimethylethyl)phenyl]thio]cyclopentanol was substituted for cis-2-[[3,5-bis(1,1-dimethylethyl)phenyl]thio]cyclopentanol.

The structure was supported by NMR, Ir and elemental analysis.

DSC 102° C.

Analysis calculated for $C_{21}H_{32}O_3S$: Theory: C, 69.19; H, 8.85; S, 8.80. Found: C, 69.51; H, 9.04; S, 8.55.

EXAMPLE 81

(±)trans-2-[[2-[[2,4-bis(1,1-dimethylethyl)phenyl]thio]cyclopentyl]oxy]acetic acid (81)

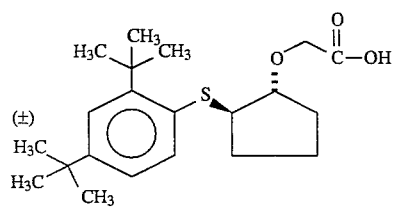

The title compound was prepared by the method described in Example 76, except that trans-2-[[2,4-bis(1,1-dimethylethyl)phenyl]thio]cyclopentanol was substituted for trans-2-[[3,5-bis(1,1-dimethylethyl)phenyl]thio]cyclopentanol. The structure was supported by NMR, Ir and elemental analysis.

Analysis calculated for $C_{21}H_{32}O_3S$: Theory: C, 69.19; H, 8.85; S, 8.80. Found: C, 69.41; H, 9.18; S, 8.58.

EXAMPLE 82

(+)cis-2-[[3,5-bis(1,1-dimethylethyl)phenyl]thio]cyclopentanol (82) (Compound A)

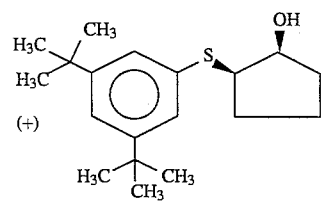

EXAMPLE 82 (cont.)

(−)cis-2-[[3,5-bis(1,1-dimethylethyl)phenyl]thio]cyclopentanol, acetate (82) (Compound B)

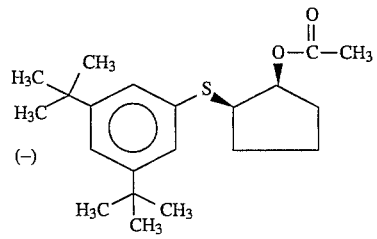

(±)-Cis-2-[[3,5-bis(1,1-dimethylethyl)phenyl]thio]cyclopentanol (4.85 g, 0.0158 mole) and AMANO Lipase PS30 (5.0 g) were stirred in 100 mL vinyl acetate at room temperature for 24 hours. The reaction mixture was filtered and the filtrate was concentrated to an oil. The title products were separated by silica gel chromatography to give first the acetate product (2.54 g) as a solid. The structure was supported by NMR. Optical rotation (CHCl₃) 589 nm −28.2°±3.34°, 365 nm −99.9°±9.08°.

The recovered starting material (2.20 g) was shown to be the (+) enantiomer. The structure was supported by NMR, Ir, optical rotation (CHCl₃, 25° C.; 589 nm +59.7° ±3.48°; 365 nm +194.6°±6.76°), chiral HPLC (chiralpak-AD, 0.5% ethanol-99.5% hexane, 0° C.) major 99.18%, minor 0.26% (same as product of Example 83), and elemental analysis.

Analysis calculated for $C_{19}H_{30}OS$: Theory: C, 74.45; H, 9.87; S, 10.46. Found: C, 74.71; H, 9.95; S, 10.57.

EXAMPLE 83

(−)cis-2-[[3,5-bis(1,1-dimethylethyl)phenyl]thio]cyclopentanol (83)

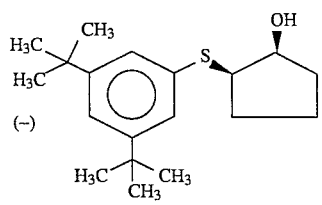

(−)-Cis-2-[[3,5-bis(1,1-dimethylethyl)phenyl]thio]cyclopentanol, acetate (2.44 g, 0.007 mole) and lithium hydroxide (0.218 g, 0.00912 mole) was stirred in methanol (100 mL) containing 20 mL of water. After 1 hour, an additional 10 mL of water was added. After 2 hours, the reaction mixture was cooled to +5° C. with an ice bath and 10% hydrochloric acid (10 mL) was added. The solution was concentrated and water (50 mL) was added to the residue. The title product was extracted into ethyl acetate (2×50 mL). The combined ethyl acetate was washed with water, dried over sodium sulfate, filtered and concentrated to an oil. The structure was purified by silica gel chromatography to give 1.97 g of a solid. The structure was supported by NMR, Ir, optical rotation (CHCl₃, 25° C. 589 nm −62 1°±3.48°; 365 nm −196.2±6.76°), chiral HPLC (chiralpak-AD, 0.5% ethanol-99.5% hexane, 0° C.) 99.46% major, 0.41% minor (same as product of Example 82, Compound A) and elemental analysis.

Analysis calculated for $C_{19}H_{30}OS$: Theory: C, 74.45; H, 9.87; S, 10.46. Found: C, 74.66; H, 9.90; S, 10.66.

EXAMPLE 84

(+)cis-2-[[2-[[3,5-bis(1,1-dimethylethyl)phenyl]thio]cyclopentyl]oxy]acetic acid (84)

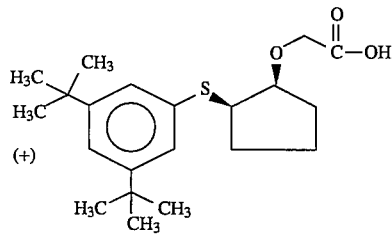

The title compound was prepared by the method described in Example 77, except that the title product of Example 82, Compound A, was substituted for the title product of Example 75, Compound A. The structure was supported by NMR, optical rotation ($CHCl_3$, 25° C.; 589 nm +66.7°±2.80°; 365 nm +212.4°) and elemental analysis.

Analysis calculated for $C_{21}H_{32}O_3S$: Theory: C, 69.19; H, 8.85; S, 8.80. Found: C, 69.03; H, 8.89; S, 8.99.

EXAMPLE 85

(−)cis-2-[[2-[[3,5-bis(1,1-dimethylethyl)phenyl]thio]cyclopentyl]oxy]acetic acid (85)

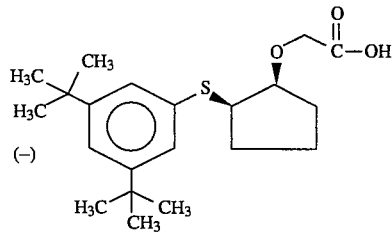

The title compound was prepared by the method described in Example 77, except that the title product of Example 83 was substituted for the title product of Example 75, Compound A. The structure was supported by NMR, optical rotation ($CHCl_3$, 25° C.; 589 nm −64.0°±2.80°; 365 nm −208.1°±6.04) and elemental analysis.

Analysis calculated for $C_{21}H_{32}O_3S$: Theory: C, 69.19; H, 8.85; S, 8.80. Found: C, 69.28; H, 9.18; S, 8.79.

EXAMPLE 86

(+)trans-2-[[3,5-bis(1,1-dimethylethyl)phenyl]thio]cyclohexanol (86) (Compound A)

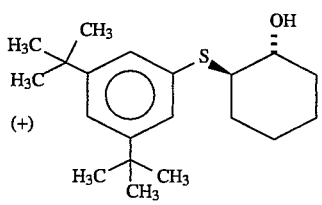

(+)trans-2-[[3,5-bis(1,1-dimethylethyl)phenyl]thio]cyclohexanol, acetate (86) (Compound B)

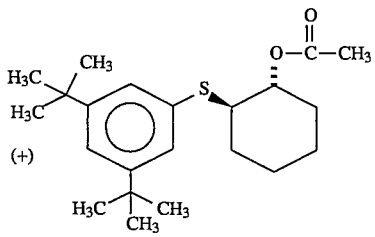

The title compounds were prepared by the method described in Example 82, except that the title product of Example 52, Compound A, was substituted for the title product of Example 75, Compound A.

Compound A—The structure was supported by NMR, Ir, optical rotation ($CHCl_3$, 25%; 589 nm +55.4°±2.80°, 365 nm +190.1°±6.04), chiral HPLC (chiralpak-AD) major 98.84%, minor 1.16% (same as product of Example 87) and elemental analysis. DSC 104.82° C.

Analysis calculated for $C_{20}H_{32}OS$: Theory: C, 74.94; H, 10.06; S, 10.00. Found: C, 75.08; H, 10.07; S, 10.16.

Compound B—The structure was supported by NMR, Ir, optical rotation ($CHCl_3$, 25° C.; 589 nm +5.8°±2.69°; 365 nm +46.3°±18.1°) and elemental analysis.

Analysis calculated for $C_{22}H_{34}O_2S$: Theory: C, 72.88; H, 9.45; S, 8.84. Found: C, 72.95; H, 9.27; S, 9.12.

EXAMPLE 87

(−)trans-2-[[3,5-bis(1,1-dimethylethyl)phenyl]thio]cyclohexanol (87)

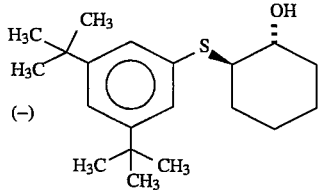

The title compound was prepared by the method described in Example 83, except that the title product of Example 86, Compound B, was substituted for the title product of Example 82, Compound B. The structure was supported by NMR, Ir, optical rotation (CHCl₃, 25° C.; 589 nm −46.8°±2.80°; 365 nm −188.9°), chiral HPLC (chiralpak-AD) major 99.50%; minor 0.26% (same as product of Example 86, Compound A) and elemental analysis.

DSC 105.05° C.

Analysis calculated for $C_{20}H_{32}OS$: Theory: C, 74.94; H, 10.06; S, 10.00. Found: C, 74.96; H, 10.08; S, 10.12.

EXAMPLE 88

(+)trans-2-[[2-[[3,5-bis(1,1-dimethylethyl)phenyl]thio]cyclohexyl]oxy]acetic acid (88)

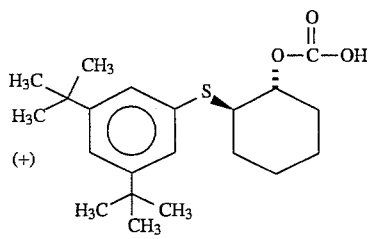

The title compound was prepared by the method described in Example 77, except that the title product of Example 86, Compound A, was substituted for the title product of Example 75, Compound A. The structure was supported by NMR, Ir, optical rotation (CHCl₃, 25° C.; 589 nm +44.6°±2.80°; 365 nm +137.0°) and elemental analysis.

Analysis calculated for $C_{22}H_{34}O_3S$: Theory: C, 69.80; H, 9.05; S, 8.47. Found: C, 70.15; H, 9.07; S, 8.33.

EXAMPLE 89

(−)trans-2-[[2-[[3,5-bis(1,1-dimethylethyl)phenyl]thio]cyclohexyl]oxy]acetic acid (89)

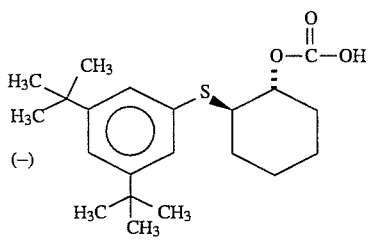

The title compound was prepared by the method described in Example 77, except that the title product of Example 87 was substituted for the title product of Example 75, Compound A. The structure was supported by NMR, Ir optical rotation (CHCl₃, 25° C.; 589 nm −42.5°±2.69°; 365 nm 138.4°±18.1°) and elemental analysis.

Analysis calculated for $C_{22}H_{34}O_3S$: Theory: C, 69.80; H, 9.05; S, 8.47. Found: C, 69.98; H, 9.10; S, 8.64.

EXAMPLE 90

(+)trans-2-[[2,4-bis(1,1-dimethylethyl)phenyl]thio]cyclopentanol (90) (Compound A)

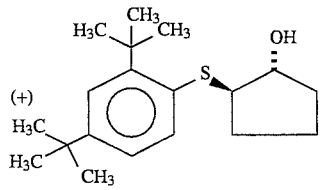

(+)trans-2-[[2,4-bis(1,1-dimethylethyl)phenyl]thio]cyclopentanol acetate (90) (Compound A)

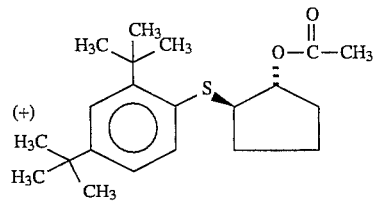

The title compounds were prepared by the method described in Example 82, except that the title product of Example 79, Compound B, was substituted for the title product of Example 75, Compound A.

Compound A—The structure was supported by NMR, Ir, optical rotation (CHCl₃, 25° C.; 589 nm +10.3°; 365 nm +77.6°), chiral HPLC (chiralpak-AD) major 99.51% minor 0.24% (same as product of Example 91) and elemental analysis.

Analysis calculated for $C_{19}H_{30}OS$: Theory: C, 74.45; H, 9.87.

Compound B—The structure was supported by NMR, Ir, optical rotation (CHCl₃, 25° C.; 589 nm +17.3±2.69°; 365 nm +76.7°±18.1°) and elemental analysis.

Analysis calculated for $C_{21}H_{32}O_2S$: Theory: C, 72.37; H, 9.25. Found: C, 72.41; H, 9.21.

EXAMPLE 91

(−)trans-2-[[2,4-bis(1,1-dimethylethyl)phenyl]thio]cyclopentanol (91)

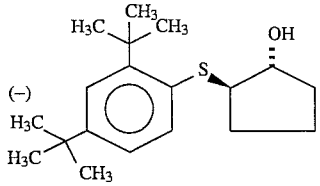

The title compound was prepared by the method described in Example 83, except that the title product of Example 90, Compound B, was substituted for the title product of Example 82, Compound B. The structure was supported by NMR, Ir, optical rotation (CHCl₃, 25° C.; 589 nm −10.5°±2.69°; 365 nm −63.4°±18.1°), chiral HPLC (chiralpak-AD) major 98.84%, minor 0.68% (product of Example 90, Compound A) and elemental analysis.

Analysis calculated for $C_{19}H_{30}OS$: Theory: C, 74.45; H, 9.87. Found: C, 74.10; H, 9.95.

EXAMPLE 92

(+)trans-2-[[2-[[2,4-bis(1,1-dimethylethyl)phenyl]thio]cyclopentyl]oxy]acetic acid (92)

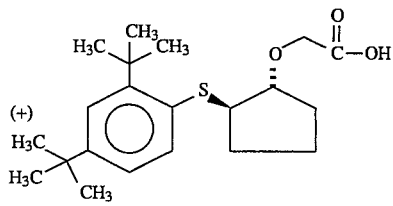

The title compound was prepared by the method described in Example 77, except that the title product of Example 90, Compound A, was substituted for the title product of Example 75, Compound A. The structure was supported by NMR, Ir, optical rotation ($CHCl_3$, 25° C.; 589 nm +1.1°±2.80; 365 nm +33.7°±6.04°), and elemental analysis.

DSC 84.10° C.

Analysis calculated for $C_{21}H_{32}O_3S$: Theory: C, 69.19; H, 8.85; S, 8.80. Found: C, 69.29; H, 9.16; S, 8.71.

EXAMPLE 93

(−)trans-2-[[2-[[2,4-bis(1,1-dimethylethyl)phenyl]thio]cyclopentyl]oxy]acetic acid (93)

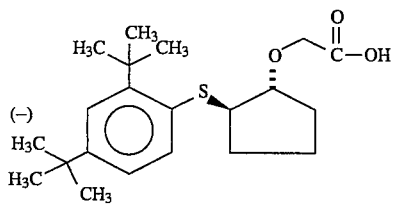

The title compound was prepared by the method described in Example 77, except that the title product of Example 91 was substituted for the title product of Example 75, Compound A. The structure was supported by NMR, Ir, optical rotation ($CHCl_3$, 25° C.; 589 nm +1.91°±2.69°; 365 nm −28.2°±18.1°) and elemental analysis.

DSC 84.44° C.

Analysis calculated for $C_{21}H_{32}O_3S$: Theory: C, 69.19; H, 8.85; S, 8.80. Found: C, 69.41; H, 9.12; S, 8.68.

EXAMPLE 94

(+)cis-2-[[2,4-bis(1,1-dimethylethyl)phenyl]thio]cyclopentanol (94) (Compound A)

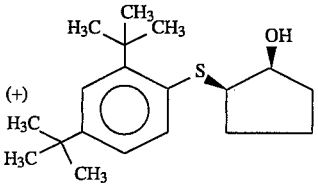

(−)cis-2-[[2,4-bis(1,1-dimethylethyl)phenyl]thio]cyclopentyl, acetate (94) (Compound A)

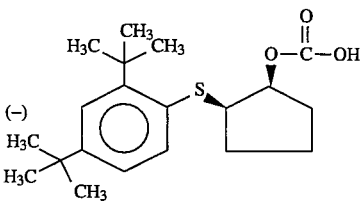

The title compounds were prepared by the method described in Example 82, except that the title product of Example 79, Compound A, was substituted for the title product of Example 75, Compound A.

Compound A—The structure was supported by NMR, Ir, optical rotation ($CHCl_3$, 25° C.; 589 nm +74.1°±2.69°; 365 nm +303.7°±18.1°) and elemental analysis.

DSC 59.44° C.

Analysis calculated for $C_{19}H_{30}OS$: Theory: C, 74.45; H, 9.87. Found: C, 74.67; H, 9.84.

Compound B—The structure was supported by NMR, Ir, optical rotation ($CHCl_3$, 25° C.; 589 nm −71.7°; 365 nm −272.4°) and elemental analysis.

Analysis calculated for $C_{21}H_{32}O_2S$: Theory: C, 72.37; H, 9.25. Found: C, 72.31; H, 9.12.

EXAMPLE 95

(−)cis-2-[[2,4-bis(1,1-dimethylethyl)phenyl]thio]cyclopentanol (95)

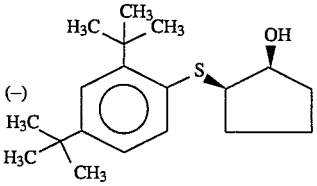

The title compound was prepared by the method described in Example 83, except that the title product of Example 94, Compound B, was substituted for the title product of Example 82, Compound B. The structure was supported by NMR, Ir, optical rotation ($CHCl_3$, 25° C.; 589 nm −77.9°±2.80°; 365 nm −316.0) and elemental analysis.

DSC 58.12° C.

Analysis calculated for $C_{19}H_{30}OS$: Theory: C, 74.45; H, 9.87. Found: C, 74.05; H, 10.34.

EXAMPLE 96

(+)cis-2-[[2-[[2,4-bis(1,1-dimethylethyl)phenyl]thio]cyclopentyl]oxy]acetic acid (96)

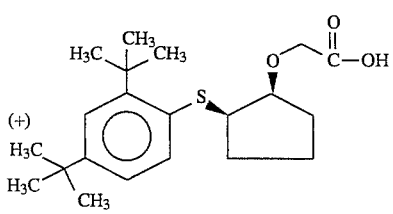

The title compound was prepared by the method described in Example 77, except that the title product of Example 94, Compound A, was substituted for the title product of Example 75, Compound A. The structure was supported by NMR, Ir, optical rotation (CHCl$_3$, 25° C.; 589 nm +44.8°±2.80°; 365 nm +194.9) and elemental analysis.

Analysis calculated for $C_{21}H_{32}O_3S$: Theory: C, 69.19; H, 8.85. Found: C, 68.95; H, 9.04.

EXAMPLE 97

(−)cis-2-[[2-[[2,4-bis(1,1-dimethylethyl)phenyl]thio]cyclopentyl]oxy]acetic acid (97)

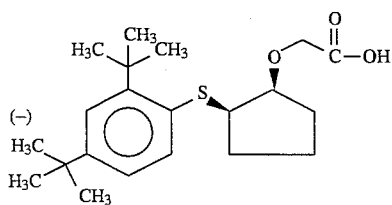

The title compound was prepared by the method described in Example 77, except that the title product of Example 95 was substituted for the title product of Example 75, Compound A. The structure was supported by NMR, Ir, optical rotation (CHCl$_3$, 25° C.; 589 nm −47.0°±2.80°; 365 nm −194.1°) and elemental analysis.

Analysis calculated for $C_{21}H_{32}O_3S$: Theory: C, 69.19; H, 8.85. Found: C, 68.91; H, 9.08.

EXAMPLE 98

Methyl (±)trans-2-[[2-[[2,4-bis(1,1-dimethylethyl)phenyl]thio]cyclopentyl]thio]acetate (98)

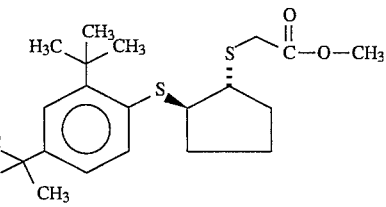

The title compound was prepared by the method described in Example 4, except that trans-2-[[2,4-bis(1,1-dimethylethyl)phenyl]thio]cyclopentanol was substituted for trans-2-[[3,5-bis(1,1-dimethylethyl)phenyl]thio]cyclohexanol. The structure was supported by NMR, Ir and elemental analysis.

Analysis calculated for $C_{22}H_{34}O_2S_2$: Theory: C, 66.96; H, 8.68. Found: C, 66.72; H, 8.77.

EXAMPLE 99 trans-2-[[2-[[3,5-bis(1,1-dimethylethyl)phenyl]thio]cyclopentyl]thio]acetic acid (99)

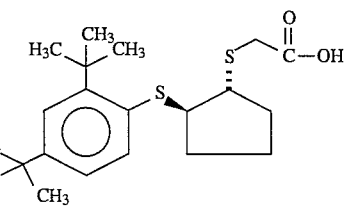

The title compound was prepared by the method described in Example 5, except that the title product of Example 98 was substituted for the title product of Example 4. The structure was supported by NMR and elemental analysis.

Analysis calculated for $C_{21}H_{32}O_2S_2$: Theory: C, 66.27; H, 8.47. Found: C, 66.35; H, 8.62.

EXAMPLE 100 trans-2-[2,4-bis(1,1-dimethylethyl)phenoxy]cyclopentanol (100)

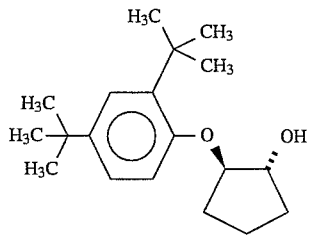

To a solution of sodium ethoxide in ethanol (prepared by dissolving 230 mg of sodium in 25 ml of ethanol) was added 2.06 g (10.0 mmoles) of 2,4-di-t-butylphenol. The mixture was stirred for 5 minutes, and then 841 mg (10.0 mmoles) of cyclopentene oxide was added. After refluxing overnight, the mixture was cooled and evaporated, the residue partitioned between diethyl ether and dilute aqueous hydrochloric acid, the aqueous layer further extracted with ether, the combined organic extracts washed with brine, dried over sodium sulfate, filtered, and evaporated. Chromatography of the residue over silica gel using 10% ethyl acetate-hexane as eluent gave the title compound, 1.25 g, as a white crystalline solid, m.p. 111.5°–112° C.

Analysis calculated for $C_{19}H_{30}O_2$ (MW 290.45): Theory: C, 78.57; H, 10.41. Found: C, 78.41; H, 10.48.

EXAMPLE 101 trans-2-[[2-[2,4-bis(1,1-dimethylethyl)phenoxy]cyclopentyl]oxy]acetic acid (101)

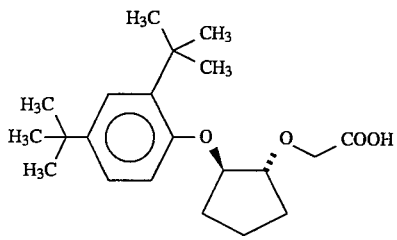

To 103 mg of 60% sodium hydride, prewashed with hexane, in 10 ml of dimethyl sulfoxide was added 500 mg of the title product of Example 100. The mixture was stirred at 40° C. until gas evolution ceased, and then 290 mg of sodium chloroacetate was added, the resulting mixture stirred at room temperature overnight and then at 80° C. for 1 hour. After cooling, the mixture was partitioned between diethyl ether and dilute aqueous hydrochloric acid, the aqueous layer further extracted with ether, the combined organic extracts washed with several portions of water and then brine, dried over sodium sulfate, filtered, and evaporated. Chromatography of the residue over silica gel using 30% ethyl acetate-2% acetic acid-68% hexane gave the title compound (155 mg) as a pure white crystalline solid, DSC 96.5° C.

Analysis calculated for $C_{21}H_{32}O_4$ (MW 348.48): Theory: C, 72.38; H, 9.26. Found: C, 72.30; H, 9.35.

The foregoing examples are provided to enable one of ordinary skill in the art to practice the present invention. These examples are merely illustrative, however, and should not be read as limiting the scope of the invention as it is claimed in the appended claims.

While the present invention has been described herein with some specificity, and with reference to certain preferred embodiments thereof, those of ordinary skill in the art will recognize numerous variations, modifications and substitutions of that which has been described which can be made, and which are within the spirit and scope of the invention. For example, effective dosages other than the preferred ranges set forth hereinabove may be applicable as a consequence of variations in the responsiveness of the animal being treated, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed. Such expected variations and/or differences in the results are contemplated in accordance with the objects and practices of the present invention. It is intended therefore that all of these modifications and variations be within the scope of the present invention as described and claimed herein, and that the invention be limited only by the scope of the claims which follow, and that such claims be interpreted as broadly as is reasonable.

What is claimed is:

1. A compound of the formula:

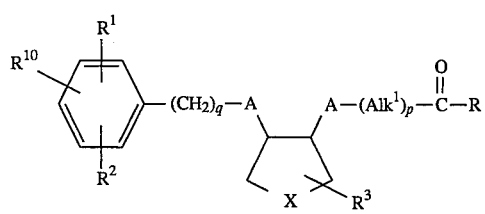

or a pharmaceutically acceptable salt thereof, wherein $R^1$, $R^2$ and $R^{10}$ are the same or different and independently represent alkyl, alkoxy, hydroxy, phenyl, halogen, trifluoromethyl, cyano, nitro or alkylthio, or hydrogen, with the proviso that when each of $R^1$ and $R^2$ is either tert-alkyl or phenyl, $R^{10}$ is not 4-hydroxy; q is 0 or 1; $R^3$ is hydrogen, alkyl, alkoxy, or hydroxy; X is O, S or $(CH_2)_m$ wherein m is an integer from 0 to 4; A is O or S(O)n wherein n is 0, 1, or 2, with the two As being the same or different; $Alk^1$ is straight or branched chain alkyl having 1 to 6 carbon atoms; p is an integer of from 0 to 2, but cannot be O when R is OH; and R is:

(a) alkyl, with the proviso that, when A is oxygen, p is 0, q is 0, and $R^1$, $R^2$ and $R^{10}$ are all hydrogen, or are 2,4,6-trimethyl, or $R^1$ and $R^2$ are 2,4-dinitro and $R^{10}$ is hydrogen, or $R^1$ and $R^2$ are H and $R^{10}$ is 4-chloro or 4-nitro or 4-methyl, then R is not methyl;

(b) OH;

(c) $OR^4$ wherein $R^4$ is alkyl of 1 to 6 carbon atoms;

(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or $Alk-NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted; or (e) $(CH_2)_tCOOR^7$ wherein t is an integer from 1 to 4 and $R^7$ is hydrogen or alkyl of 1 to 4 carbon atoms.

2. A compound of the formula:

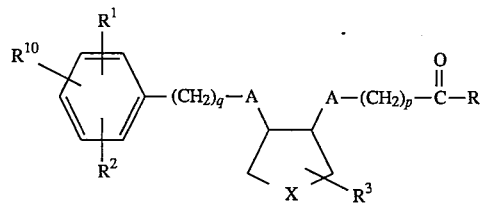

or a pharmaceutically acceptable salt thereof, wherein $R^1$, $R^2$ and $R^{10}$ are the same or different and independently represent alkyl, alkoxy, phenyl, halogen, trifluoromethyl, cyano, or hydrogen; q is 0 or 1; $R^3$ is hydrogen, alkyl, alkoxy, or hydroxy; X is O, S or $(CH_2)_m$ wherein m is an integer from 0 to 4; A is O or $S(O)_n$ wherein n is 0, 1, or 2, with the two As being the same or different; p is an integer of from 0 to 2, but cannot be O when R is OH; and R is:

(a) alkyl, with the proviso that, when A is oxygen, p is 0, q is 0, and $R^1$, $R^2$ and $R^{10}$ are all hydrogen, or are 2,4,6-trimethyl, or $R^1$ and $R^2$ are 2,4-dinitro and $R^{10}$ is hydrogen, or $R^1$ and $R^2$ are H and $R^{10}$ is 4-chloro or 4-nitro or 4-methyl, then R is not methyl;

(b) OH;

(c) $OR^4$ wherein $R^4$ is alkyl of 1 to 6 carbon atoms;

(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or Alk-$NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted; or (e) $(CH_2)_tCOOR^7$ wherein t is an integer from 1 to 4 and $R^7$ is hydrogen or alkyl of 1 to 4 carbon atoms.

3. A compound of the formula:

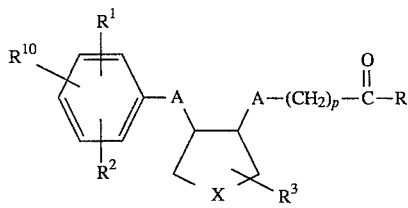

or a pharmaceutically acceptable salt thereof, wherein $R^1$, $R^2$ and $R^{10}$ are the same or different and independently represent tert-alkyl of 4 to 10 carbon atoms, phenyl, halogen, or hydrogen; $R^3$ is hydrogen or alkyl of 1 to 4 carbon atoms; X is O, S or $(CH_2)_m$ wherein m is 1 or 2; A is O or $S(O)_n$ wherein n is 0, 1, or 2, with the two As being the same or different; p is an integer of from 0 to 4, but cannot be O when R is OH; and R is:

(a) alkyl of 1 to 4 carbon atoms, with the proviso that when A is oxygen, p is 0, and $R^1$, $R^2$ and $R^{10}$ are all hydrogen, then R is not methyl;

(b) OH;

(c) $OR^4$ wherein $R^4$ is alkyl of 1 to 4 carbon atoms;

(d) $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or Alk-$NR^8R^9$ wherein Alk is straight or branched chain alkyl of 1 to 6 carbon atoms and $R^8$ and $R^9$ each independently are hydrogen or alkyl of 1 to 4 carbon atoms; or $NR^5R^6$ together form a heterocyclic ring which may optionally be substituted; or (e) $(CH_2)_tCOOR^7$ wherein t is an integer from 1 to 4 and $R^7$ is hydrogen or alkyl of 1 to 4 carbon atoms.

4. A compound of claim 1 of the formula:

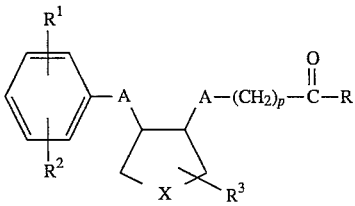

wherein $R^1$ and $R^2$ are the same or different and independently represent tert-butyl, phenyl, halogen, or hydrogen; $R^3$ is hydrogen or alkyl of 1 to 4 carbon atoms; X is O or $(CH_2)_m$ wherein m is 1 or 2; A is O or S, with the two As being the same or different; and R is:

(a) OH;

(b) $OR^4$ wherein $R^4$ is alkyl of 1 to 4 carbon atoms; or (c) $NR^5R^6$ wherein $R^5$ is hydrogen or alkyl of 1 to 4 carbon atoms and $R^6$ is hydrogen, alkyl of 1 to 4 carbon atoms or heterocyclealkyl wherein the alkyl moiety has 1 to 4 carbon atoms, hydroxyalkyl, alkoxyalkyl, substituted phenyl, or Alk-$NR^8R^9$ wherein Alk is straight or branched chain alkyl of 1 to 6 carbon atoms and $R^8$ and $R^9$ are each independently hydrogen or alkyl of 1 to 4 carbon atoms; or $NR^5R^6$ together form a heterocyclic ring which may optionally be substituted;

or a pharmaceutically acceptable salt thereof.

5. A compound of claim 4 wherein R is:

(a) OH;

(b) $OR^4$ wherein $R^4$ is alkyl of 1 to 4 carbon atoms; or (c) $NR^5R^6$ wherein $R^5$ is hydrogen or alkyl of 1 to 4 carbon atoms and $R^6$ is hydrogen, alkyl of 1 to 4 carbon atoms, substituted phenyl, hydroxyalkyl, alkoxyalkyl wherein the alkyl moieties each have 1 to 6 carbon atoms, heterocyclealkyl wherein the alkyl moiety has 1 to 4 carbon atoms, or Alk-$NR^8R^9$ wherein Alk is straight or branched chain alkyl of 1 to 6 carbon atoms and $R^8$ and $R^9$ are each independently hydrogen or alkyl of 1 to 4 carbon atoms; or $NR^5R^6$ together form a heterocyclic ring which may optionally be substituted.

6. A compound of claim 5 of the formula:

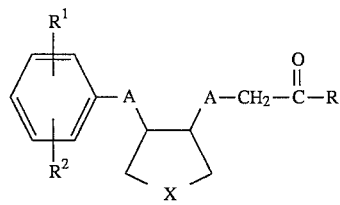

(IV)

wherein $R^1$ and $R^2$ are the same or different and independently represent tert-butyl, phenyl or hydrogen; X is $(CH_2)_m$ wherein m is 1 or 2; and R is:

(a) OH;

(b) $OR^4$ wherein $R^4$ is alkyl of 1 to 4 carbon atoms; or (c) $NR^5R^6$ wherein $R^5$ is hydrogen or alkyl of 1 to 4 carbon atoms and $R^6$ is hydroxyalkyl, alkoxyalkyl wherein the alkyl moieties each have 1 to 4 carbon atoms; heterocyclealkyl wherein the alkyl moiety has 1 to 4 carbon atoms; substituted phenyl having one or more substituents selected from the group consisting of alkyl, hydroxy, alkoxy, halogen, alkylamino, dialkylamino, phenyl, and alkyl carbonyl; or Alk-$NR^8R^9$ wherein Alk is straight or branched chain alkyl of 1 to 4 carbon atoms and $R^8$ and $R^9$ are each independently hydrogen or alkyl of 1 to 4 carbon atoms;

or a pharmaceutically acceptable salt thereof.

7. A compound of claim 6 wherein $R^1$ and $R^2$ are tertbutyl or phenyl; and R is:

(a) OH;

(b) $OR^4$ wherein $R^4$ is alkyl of 1 to 4 carbon atoms; or (c) $NR^5R^6$ wherein $R^5$ is alkyl of 1 to 4 carbon atoms and $R^6$ is substituted phenyl, hydroxyalkyl, alkoxyalkyl wherein the alkyl moieties have 1 to 4 carbon atoms; pyridinylalkyl wherein the alkyl moiety has 1 to 4 carbon atoms; or $Alk-NR^8R^9$ wherein Alk is alkyl of 1 to 4 carbon atoms and $R^8$ and $R^9$ are hydrogen or alkyl of 1 to 4 carbon atoms;

or a pharmaceutically acceptable salt thereof.

8. A compound of claim 1 which is selected from the group consisting of:

methyl trans-[[2-[[3,5-bis(1,1-dimethylethyl)phenyl]thio]cyclohexyl]thio]acetate (4);

trans-[[2-[[3,5-bis(1,1-dimethylethyl)phenyl]thio]cyclohexyl]thio]acetic acid (5);

trans-[[2-(phenylthio)cyclohexyl]thio]acetic acid (7);

trans-[[2-[[3-(1,1-dimethylethyl)phenyl]thio]cyclohexyl]thio]acetic acid (11);

trans-[[2-[([1,1'-biphenyl]-3-yl)thio]cyclohexyl]thio]acetic acid (15);

trans-2-[[2-[[3,5-bis(1,1-dimethylethyl)phenyl]thio]cyclohexyl]thio]-N-methyl-N-(2-pyridinylethyl)acetamide (16);

trans-[[2-[[3,5-bis(1,1-dimethylethyl)phenyl]thio]cyclohexyl]oxy]acetic acid (17);

trans-2-[[2-[[1,1'-biphenyl]-3-ylthio]cyclohexyl]thio]-N-(2,6-dimethylphenyl)acetamide (22);

trans-2-[[2-[[3,5-bis(1,1-dimethylethyl)phenyl]thio]-cyclohexyl]thio]-N-[3-(dimethylamino)propyl]-N-methylacetamide (23);

trans-2-[[2-[[3,5-bis(1,1-dimethylethyl)phenyl]thio]cyclohexyl]thio]-N-[4-(dimethylamino)butyl]acetamide (24);

trans-2-[[2-[[3,5-bis(1,1-dimethylethyl)phenyl]thio]cyclohexyl]thio]-N-(2-methoxyethyl)acetamide (25);

cis-2-[[2-[[3,5-bis(1,1-dimethylethyl)phenyl]thio]cyclohexyl]oxy]acetic acid (72);

(+)trans-2-[[2-[[3,5-bis(1,1-dimethylethyl)phenyl]thio]cyclopentyl]oxy]acetic acid (76);

(+)cis-2-[[2-[[3,5-bis(1,1-dimethylethyl)phenyl]thio]cyclopentyl]oxy]acetic acid (77);

(+)cis-2-[[2-[[2,4-bis(1,1-dimethylethyl)phenyl]thio]cyclopentyl]oxy]acetic acid (80);

(+)trans-2-[[2-[[2,4-bis(1,1-dimethylethyl)phenyl]-thio]cyclopentyl]-oxy]acetic acid (81);

(+)cis-2-[[2-[[3,5-bis(1,1-dimethylethyl)phenyl]thio]cyclopentyl]oxy]acetic acid (84);

(−)cis-2-[[2-[[3,5-bis(1,1-dimethylethyl)phenyl]thio]cyclopentyl]oxy]acetic acid (85);

(+)trans-2-[[2-[[3,5-bis(1,1-dimethylethyl)phenyl]thio]cyclohexyl]oxy]acetic acid (88);

(−)trans-2-[[2-[[3,5-bis(1,1-dimethylethyl)phenyl]thio]cyclohexyl]oxy]acetic acid (89);

(+)trans-2-[[2-[[2,4-bis(1,1-dimethylethyl)phenyl]thio]cyclopentyl]oxy]acetic acid (92);

(−)trans-2-[[2-[[2,4-bis(1,1-dimethylethyl)phenyl]thio]cyclopentyl]oxy]acetic acid (93);

(+)cis-2-[[2-[[2,4-bis(1,1-dimethylethyl)phenyl]thio]cyclopentyl]oxy]acetic acid (96);

(−)cis-2-[[2-[[2,4-bis(1,1-dimethylethyl)phenyl]thio]cyclopentyl]oxy]acetic acid (97);

trans-2-[[2-[[3,5-bis(1,1-dimethylethyl)-phenyl]thio]cyclopentyl]thio]acetic acid (99); and trans-2-[[2-[2,4-bis(1,1-dimethylethyl)phenoxy]cyclopentyl]oxy]acetic acid (101).

9. A compound having the structure:

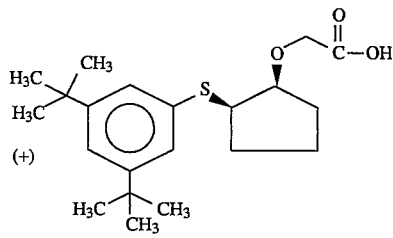

10. A pharmaceutical composition comprising a pharmaceutically-acceptable carrier and a pharmaceutically-effective amount of a compound of claim 1.

11. The pharmaceutical composition of claim 10 wherein the compound is:

cis-2-[[2-[[3,5-bis(1,1-dimethylethyl)phenyl]thio]cyclohexyl]oxy]acetic acid (72);

(+)trans-2-[[2-[[3,5-bis(1,1-dimethylethyl)phenyl]thio]cyclopentyl]oxy]acetic acid (76);

(+)cis-2-[[2-[[3,5-bis(1,1-dimethylethyl)phenyl]thio]cyclopentyl]oxy]acetic acid (77);

(+)cis-2-[[2-[[2,4-bis(1,1-dimethylethyl)phenyl]thio]cyclopentyl]oxy]acetic acid (80);

(+)trans-2-[[2-[[2,4-bis(1,1-dimethylethyl)phenyl]-thio]cyclopentyl]-oxy]acetic acid (81);

(+)cis-2-[[2-[[3,5-bis(1,1-dimethylethyl)phenyl]thio]cyclopentyl]oxy]acetic acid (84);

(−)cis-2-[[2-[[3,5-bis(1,1-dimethylethyl)phenyl]thio]cyclopentyl]oxy ]acetic acid (85);

(+)trans-2-[[2-[[3,5-bis(1,1-dimethylethyl)phenyl]thio]cyclohexyl]oxy]acetic acid (88);

(−)trans-2-[[2-[[3,5-bis(1,1-dimethylethyl)phenyl]thio]cyclohexyl]oxy]acetic acid (89);

(+)trans-2-[[2-[[2,4-bis(1,1-dimethylethyl)phenyl]thio]cyclopentyl]oxy]acetic acid (92);

(−)trans-2-[[2-[[2,4-bis(1,1-dimethylethyl)phenyl]thio]cyclopentyl]oxy]acetic acid (93);

(+)cis-2-[[2-[[2,4-bis(1,1-dimethylethyl)phenyl]thio]cyclopentyl]oxy ]acetic acid (96);

(−)cis-2-[[2-[[2,4-bis(1,1-dimethylethyl)phenyl]thio]cyclopentyl]oxy]acetic acid (97);

trans-2-[[2-[[3,5-bis(1,1-dimethylethyl)-phenyl]thio]cyclopentyl]thio]acetic acid (99); and trans-2-[[2-[2,4-bis(1,1-dimethylethyl)phenoxy]cyclopentyl]oxy]acetic acid (101).

12. A pharmaceutical composition for use in inhibiting superoxide generation in an animal which comprises an amount of a compound of the formula:

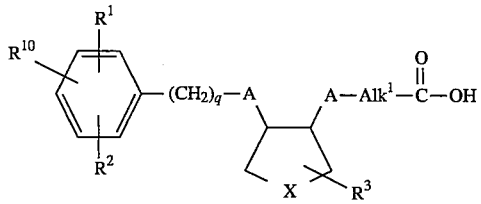

or a pharmaceutically acceptable salt thereof wherein $R^1$, $R^2$ and $R^{10}$ are the same or different and independently represent alkyl, alkoxy, hydroxy, phenyl, halogen, trifluoromethyl, cyano, or hydrogen, with the proviso that when each of $R^1$ and $R^2$ is either tert-alkyl or phenyl, $R^{10}$ is not 4-hydroxy; q is 0 or 1; $R^3$ is hydrogen, alkyl, alkoxy, or hydroxy; X is O, S or $(CH_2)_m$ wherein m is an integer from 0 to 4; A is O or $S(O)_n$ wherein n is 0, 1, or 2, with the two As being the same or different; and $Alk^1$ is straight or branched chain alkyl having 1 to 6 carbon atoms, which is effective to inhibit superoxide generation; and a pharmaceutically acceptable carrier.

13. A pharmaceutical composition for use in inhibiting superoxide generation in a mammal which comprises an amount of a compound of the formula:

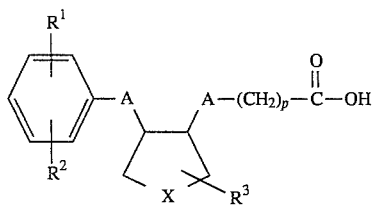

wherein $R^1$ and $R^2$ are the same or different and independently represent tert-alkyl, phenyl, halogen or hydrogen; $R^3$ is hydrogen or alkyl of 1 to 4 carbon atoms; X is O, S or $(CH_2)_m$ wherein m is 1 or 2; A is O or $S(O)_n$ wherein n is 0, 1, or 2, with the two As being the same or different; and p is an integer of from 1 to 4; or a pharmaceutically acceptable salt thereof, which is effective to inhibit superoxide generation; and a pharmaceutically acceptable carrier.

14. A pharmaceutical composition of claim 13 wherein said compound is selected from the group consisting of:
trans-[[2-[[3,5-bis(1,1-dimethylethyl)phenyl]thio]cyclohexyl]thio]acetic acid (5);
trans-[[2-(phenylthio)cyclohexyl]thio]acetic acid (7);
trans-[[2-[[3-(1,1-dimethylethyl)phenyl]thio]cyclohexyl] thio]acetic acid (11);
trans-[[2-[([1,1'-biphenyl]-3-yl)thio]cyclohexyl]thio]acetic acid (15); and
trans-[[2-[[3,5-bis(1,1-dimethylethyl)phenyl]thio]cyclohexyl]oxy]acetic acid (17).

15. A pharmaceutical composition for use in stimulating superoxide generation in an animal which comprises a compound of the formula:

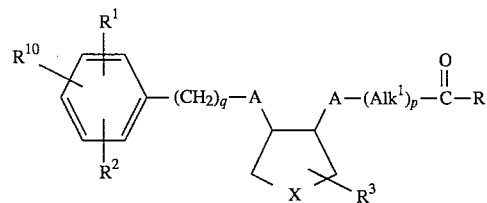

or a pharmaceutically acceptable salt thereof wherein $R^1$, $R^2$ and $R^{10}$ are the same or different and independently represent alkyl, alkoxy, hydroxy, phenyl, halogen, trifluoromethyl, cyano, or hydrogen, with the proviso that when each of $R^1$ and $R^2$ is either tert-alkyl or phenyl, $R^{10}$ is not 4-hydroxy; q is 0 or 1; $R^3$ is hydrogen, alkyl, alkoxy, or hydroxy; X is O, S or $(CH_2)_m$ wherein m is an integer from 0 to 4; A is O or $S(O)_n$ wherein n is 0, 1, or 2, with the two As being the same or different; $Alk^1$ is straight or branched chain alkyl having 1 to 6 carbon atoms; p is 0 or 1; and R is $OR^4$ wherein $R^4$ is alkyl of 1 to 6 carbon atoms; or $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, or substituted phenylalkyl, or $Alk-NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted which is effective to stimulate superoxide generation and a pharmaceutically acceptable carrier.

16. A pharmaceutical composition for use in stimulating superoxide generation in an animal which comprises an amount of a compound of the formula:

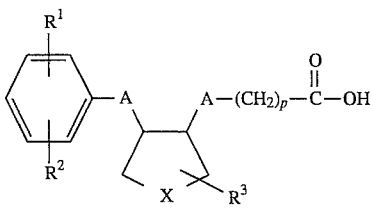

wherein $R^1$ and $R^2$ are the same or different and independently represent tert-alkyl, phenyl, or hydrogen; $R^3$ is hydrogen or alkyl of 1 to 4 carbon atoms; X is O, S or $(CH_2)_m$ wherein m is 1 or 2; A is O or $S(O)_n$ wherein n is 0, 1, or 2, with the two As being the same or different; p is an integer from 1 to 4; and R is $OR^4$ wherein $R^4$ is alkyl of 1 to 4 carbon atoms; or $NR^5R^6$ wherein $R^5$ is hydrogen or alkyl, and $R^6$ is hydrogen, alkyl, alkoxyalkyl, heterocyclealkyl, substituted heterocyclealkyl, cycloalkyl, substituted cycloalkyl, phenyl, substituted phenyl, phenylalkyl, substituted phenylalkyl or $Alk-NR^8R^9$ wherein Alk is alkyl of 1 to 6 carbon atoms and $R^8$ and $R^9$ each independently are hydrogen or alkyl of 1 to 4 carbon atoms; or $NR^5R^6$ together form a heterocyclic ring which may optionally be substituted; or a pharmaceutically acceptable salt thereof, which is effective to stimulate superoxide generation and a pharmaceutically acceptable carrier.

17. A pharmaceutical composition of claim 16 wherein the compound is selected from the group consisting of:
methyl trans-[[2-[[3,5-bis(1,1-dimethylethyl)phenyl]thio] cyclohexyl]thio]acetate (4);
trans-2-[[2-[[3,5-bis(1,1-dimethylethyl)phenyl]thio]cyclohexyl]thio]-N-methyl-N-(2-pyridinylethyl)acetamide (16);
trans-2-[[2-[[1,1'-biphenyl]-3-ylthio]cyclohexyl]thio]-N-(2,6-dimethylphenyl)acetamide (22);
trans-2-[[2-[[3,5-bis(1,1-dimethylethyl)phenyl]thio]-cyclohexyl]thio]-N-[3-(dimethylamino)propyl]-N-methyacetamide (23);
trans-2-[[2-[[3,5-bis(1,1-dimethylethyl)phenyl]thio]cyclohexyl] thio]-N-[4-(dimethylamino)butyl]acetamide (24); and
trans-2-[[2-[[3,5-bis(1,1-dimethylethyl)phenyl]thio]cyclohexyl]thio]-N-(2-methoxyethyl)acetamide (25).

18. A method of inhibiting superoxide generation in an animal which comprises administering to an animal in need of such treatment an amount of a compound of the formula:

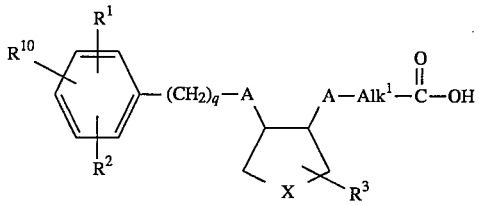

or a pharmaceutically acceptable salt thereof wherein $R^1$, $R^2$ and $R^{10}$ are the same or different and independently represent alkyl, alkoxy, hydroxy, phenyl, halogen, trifluoromethyl, cyano, or hydrogen, with the proviso that when each of $R^1$ and $R^2$ is either tert-alkyl or phenyl, $R^{10}$ is not 4-hydroxy; t is 0 or 1; $R^3$ is hydrogen, alkyl, alkoxy, or hydroxy; X is O, S or $(CH_2)_m$ wherein m is an integer from 0 to 4; A is O or $S(O)_n$ wherein n is 0, 1, or 2, with the two As being the same or different; and $Alk^1$ is straight or branched chain alkyl having 1 to 6 carbon atoms, which is effective to inhibit superoxide generation.

19. A method of inhibiting superoxide generation in an animal which comprises administering to an animal in need of such treatment an amount of a compound of the formula:

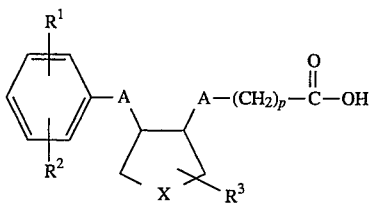

wherein $R^1$ and $R^2$ are the same or different and independently represent tert-alkyl, phenyl, or hydrogen; $R^3$ is hydrogen or alkyl of 1 to 4 carbon atoms; X is O, S or $(CH_2)_m$ wherein m is 1 or 2; A is O or $S(O)_n$ wherein n is 0, 1, or 2, with the two As being the same or different; and p is an integer from 1 to 4; or a pharmaceutically acceptable salt thereof, which is effective to inhibit superoxide generation.

20. A method according to claim 19 wherein said compound is selected from the group consisting of:

trans-[[2-[[3,5-bis(1,1-dimethylethyl)phenyl]thio]cyclohexyl]thio]acetic acid (5);

trans-[[2-(phenylthio)cyclohexyl]thio]acetic acid (7);

trans-[[2-[[3-(1,1-dimethylethyl)phenyl]thio]cyclohexyl]thio]acetic acid (11);

trans-[[2-[([1,1'-biphenyl]-3-yl)thio]cyclohexyl]thio]acetic acid (15); and trans-[[2-[[3,5-bis(1,1-dimethylethyl)phenyl]thio]cyclohexyl]oxy]acetic acid (17).

21. A method of stimulating superoxide generation in an animal which comprises administering to an animal in need of such treatment an amount of a compound of the formula:

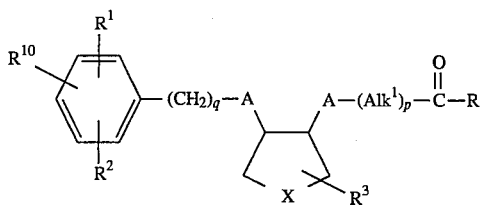

or a pharmaceutically acceptable salt thereof, wherein $R^1$, $R^2$ and $R^{10}$ are the same or different and independently represent alkyl, alkoxy, hydroxy, phenyl, halogen, trifluoromethyl, cyano, or hydrogen, with the proviso that when each of $R^1$ and $R^2$ is either tert-alkyl or phenyl, $R^{10}$ is not 4-hydroxy; t is 0 or 1; $R^3$ is hydrogen, alkyl, alkoxy, or hydroxy; X is O, S or $(CH_2)_m$ wherein m is an integer from 0 to 4; A is O or $S(O)_n$, wherein n is 0, 1, or 2, with the two As being the same or different; $Alk^1$ is straight or branched chain alkyl having 1 to 6 carbon atoms; p is 0 or 1; and R is $OR^4$ wherein $R^4$ is alkyl of 1 to 6 carbon atoms or $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, or substituted phenylalkyl, or $Alk-NR^8R^9$ wherein Alk is alkyl of 1 to 10 carbon atoms and $R^8$ and $R^9$ each independently are hydrogen or alkyl; or $NR^5R^6$ together form a heterocyclic ring which may optionally be substituted, which is effective to stimulate superoxide generation.

22. A method of stimulating superoxide generation in an animal which comprises administering to an animal in need of such treatment an amount of a compound of the formula:

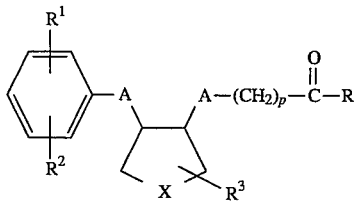

wherein $R^1$ and $R^2$ are the same or different and independently represent tert-alkyl, phenyl, or hydrogen; $R^3$ is hydrogen or alkyl of 1 to 4 carbon atoms; X is O, S or $(CH_2)_m$ wherein m is 1 or 2; A is O or $S(O)_n$ wherein n is 0, 1, or 2, with the two As being the same or different; p is an integer from 0 to 4; and R is $OR^4$ wherein $R^4$ is alkyl of 1 to 4 carbon atoms; $NR^5R^6$ wherein $R^5$ is hydrogen or alkyl, and $R^6$ is hydrogen, alkyl, hydroxyalkyl, alkoxyalkyl, heterocyclealkyl, substituted heterocyclealkyl, cycloalkyl, substituted cycloalkyl, phenyl, substituted phenyl, phenylalkyl, substituted phenylalkyl, or $Alk-NR^8R^9$ wherein Alk is alkyl of 1 to 6 carbon atoms and $R^8$ and $R^9$ each independently are hydrogen or alkyl of 1 to 4 carbon atoms; or $NR^5R^6$ together form a heterocyclic ring which may optionally be substituted; or a pharmaceutically acceptable salt thereof, which is effective to stimulate superoxide generation.

23. A method according to claim 22 wherein said compound is selected from the group consisting of methyl trans-[[2-[[3,5-bis(1,1-dimethylethyl)phenyl]thio]cyclohexyl]thio]acetate (4);

trans-2-[[2-[[3,5-bis(1,1-dimethylethyl)phenyl]thio]cyclohexyl]thio]-N-methyl-N-(2pyridinylethyl)acetamide (16);

trans-2-[[2-[[1,1'-biphenyl]-3-ylthio]cyclohexyl]thio]-N-(2,6-dimethylphenyl)acetamide (22);

trans-2-[[2-[[3,5-bis(1,1-dimethylethyl)phenyl]thio]-cyclohexyl]thio]-N-[3-(dimethylamino)propyl]-N-methylacetamide (23);

trans-2-[[2-[[3,5-bis(1,1-dimethylethyl)phenyl]thio]cyclohexyl]thio]-N-[4-(dimethylamino)butyl]acetamide (24); and trans-2-[[2-[[3,5-bis(1,1-dimethylethyl)phenyl]thio]cyclohexyl]thio]-N-(2-methoxyethyl)acetamide (25).

\* \* \* \* \*